United States Patent
Stanley et al.

(10) Patent No.: US 10,745,717 B2
(45) Date of Patent: Aug. 18, 2020

(54) VECTORS AND METHODS FOR TARGETED INTEGRATION IN LOCI COMPRISING CONSTITUTIVELY EXPRESSED GENES

(71) Applicant: MURDOCH CHILDRENS RESEARCH INSTITUTE, Victoria (AU)

(72) Inventors: Ed Stanley, Victoria (AU); Andrew Elefanty, Victoria (AU); David Elliott, Victoria (AU); Tatiana Labonne, Victoria (AU)

(73) Assignee: Murdoch Children's Research Institute, Victoria (AU)

( * ) Notice: Subject to any disclaimer, the term of this patent is extended or adjusted under 35 U.S.C. 154(b) by 0 days.

(21) Appl. No.: 15/525,380

(22) PCT Filed: Nov. 10, 2015

(86) PCT No.: PCT/AU2015/000682
§ 371 (c)(1),
(2) Date: May 9, 2017

(87) PCT Pub. No.: WO2016/074016
PCT Pub. Date: May 19, 2016

(65) Prior Publication Data
US 2018/0057842 A1  Mar. 1, 2018

(30) Foreign Application Priority Data
Nov. 10, 2014 (AU) .................. 2014904499

(51) Int. Cl.
*C12N 15/00* (2006.01)
*C12N 15/90* (2006.01)
*C12N 5/10* (2006.01)
*C12N 15/85* (2006.01)

(52) U.S. Cl.
CPC ............ *C12N 15/907* (2013.01); *C12N 5/10* (2013.01); *C12N 15/85* (2013.01); *A01K 2217/072* (2013.01); *A01K 2217/203* (2013.01); *A01K 2267/0393* (2013.01); *C12N 2800/24* (2013.01); *C12N 2830/002* (2013.01); *C12N 2840/107* (2013.01); *C12N 2840/203* (2013.01)

(58) Field of Classification Search
None
See application file for complete search history.

(56) References Cited

U.S. PATENT DOCUMENTS

2002/0142468 A1* 10/2002 Sundstrom ............ C07K 14/40
  435/484
2003/0211495 A1* 11/2003 Hopkins ................ C12Q 1/025
  435/6.16
2013/0203078 A1* 8/2013 Paz-Rojas .......... G01N 33/5044
  435/7.21
2013/0280222 A1* 10/2013 Kay ....................... C12N 15/85
  424/93.21
2013/0344604 A1* 12/2013 Aebischer-Gumy ........................
  C12N 15/85
  435/455

FOREIGN PATENT DOCUMENTS

CA          2599784 A1     9/2006

OTHER PUBLICATIONS

Hu et al., "Generation of a stable mammalian cell line for simultaneous expression of multiple genes by using 2A peptide-based lentiviral vector," (Biotechnol Lett, 2009, pp. 353-359, vol. 31.) (Year: 2009).*
Score result to Leuscher (SEQ 2) (Year: 2013).*
Score result to Paz Rojas et al (SEQ 4) (Year: 2013).*
Score result to Leuscher et al (SEQ 3) (Year: 2013).*
Papapetrou et al. in "Genomic safe Harbors permit high beta-globin transgene expression in thalassemia induced pluripotent stem cells" (Nature Biotechnology, vol. 29, No. 1, 2011, pp. 73-78; (Year: 2011).*
International Search Report and Written Opinion corresponding to PCT/AU2015/000682 dated Dec. 24, 2015 (9 pages).
Papapetrou, Eirini P. et al., "Genomic Safe Harbors Permit High beta-Globin Transgene Expression in Thalassemia Induced Pluripotent Stem Cells," Nature Biotechnology (Jan. 2011; published online Dec. 12, 2010); 29(1): 73-78.
Chambers, S.M. et al. (Mar. 2009, e-published Mar. 1, 2009). "Highly efficient neural conversion of human ES and iPS cells by dual inhibition of SMAD signaling," *Nat Biotechnol* 27(3):275-280.
Elliott, D.A. et al. (Oct. 23, 2011). "NKX2-5(eGFP/w) hESCs for isolation of human cardiac progenitors and cardiomyocytes," *Nat Methods* 8(12):1037-1040.
European Search Report dated May 8, 2018, for EP Application No. 15858620.6, filed Nov. 10, 2015, 7 pages.
Kao, T. et al. (Sep. 13, 2016, e-published Sep. 1, 2016). "GAPTrap: A Simple Expression System for Pluripotent Stem Cells and Their Derivatives," *Stem Cells Reports* 7(3):518-526.
Sadelain, M. et al. (Jan. 2012). "Safe harbours for the integration of new DNA in the human genome," *Nature Reviews Cancer* 12:51-58.

* cited by examiner

*Primary Examiner* — Catherine S Hibbert
(74) *Attorney, Agent, or Firm* — Mintz Levin Cohn Ferris Glovsky and Popeo, P.C.

(57) ABSTRACT

The invention relates to a vector comprising: a 5' nucleic acid that is homologous to a genomic sequence 5' of a stop codon of a constitutively expressed gene; an exogenous nucleic acid; a 3' nucleic acid that is homologous to a genomic sequence 3' of the stop codon of the constitutively expressed gene; a translation interruption-reinitiation signal operably linked to the 5' nucleic acid and the exogenous nucleic acid, wherein the translation interruption-reinitiation signal is capable of replacing the stop codon of the constitutively expressed gene.

18 Claims, 32 Drawing Sheets

Specification includes a Sequence Listing.

| Suspension EB | | | | | | | | | Adherent EB | | | | |
|---|---|---|---|---|---|---|---|---|---|---|---|---|---|
| BMP4 | VEGF | ActA | BMP4 | SCF | VEGF | IL3 | IL6 | bFGF | Apelin | Epo | d4 Growth Factors + TpO | Flt3 | G-CSF | GM-CSF | IGF-2 |
| 20 | 50 | 2 | 20 | 100 | 50 | 25 | 25 | 10 | 50 | 2 | 50 | 50 | 50 | 25 | 25 |
| STEMDiff APEL | | | STEMDiff APEL | | | | | | | | STEMDiff APEL | | |
| d0 | | | d4 | | | | | | | | d7 | | | | d14 |

Fig. 3

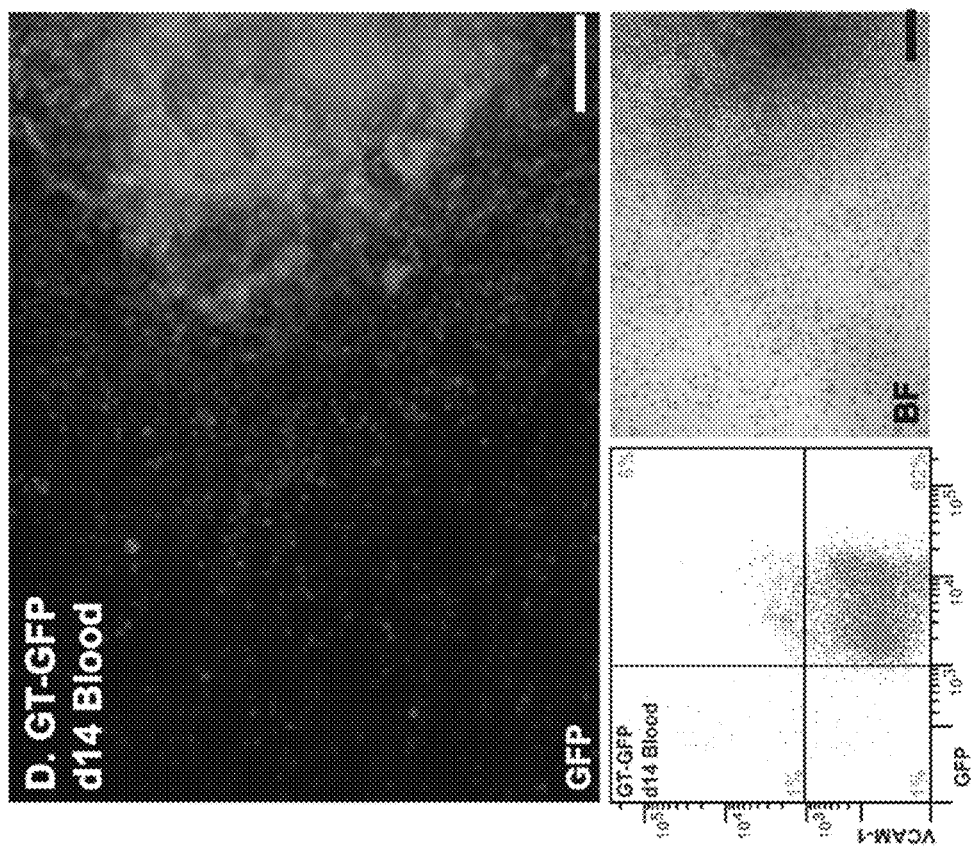
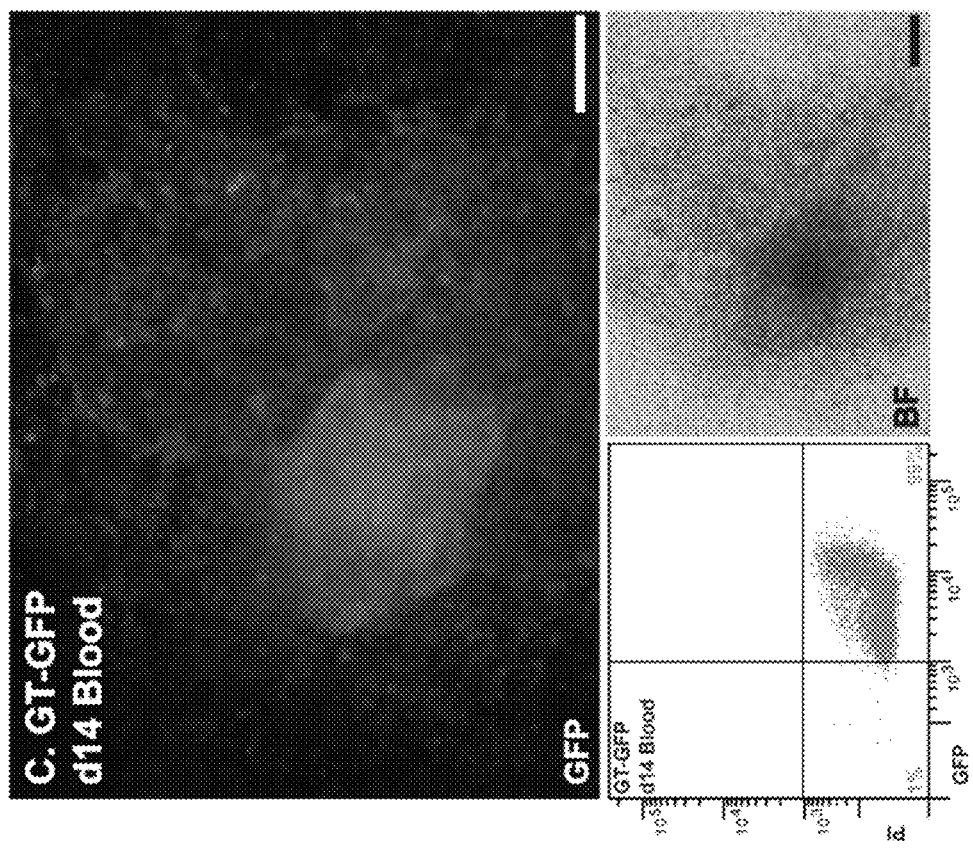
Fig. 5D
Fig. 5C

Fig. 7A
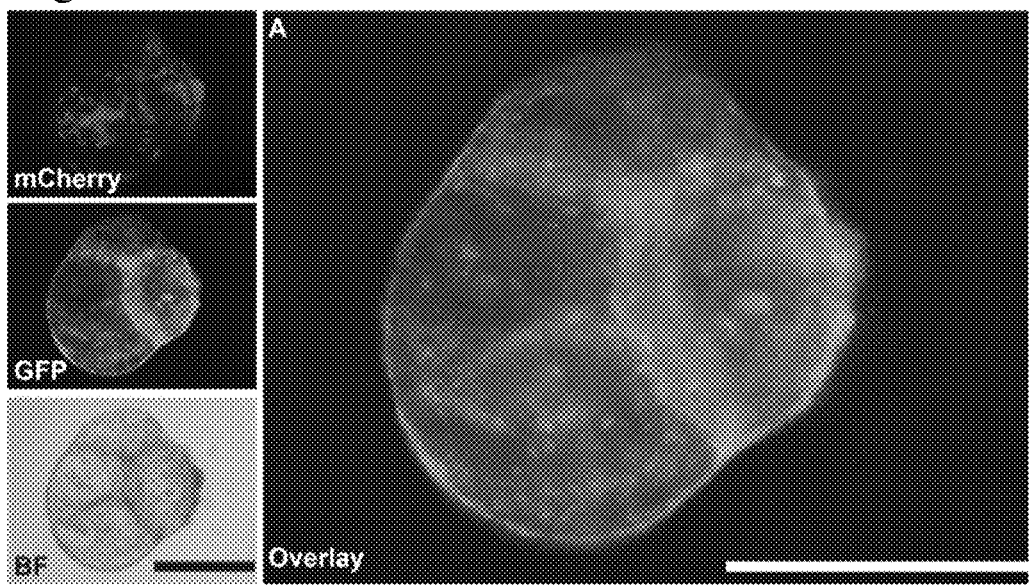
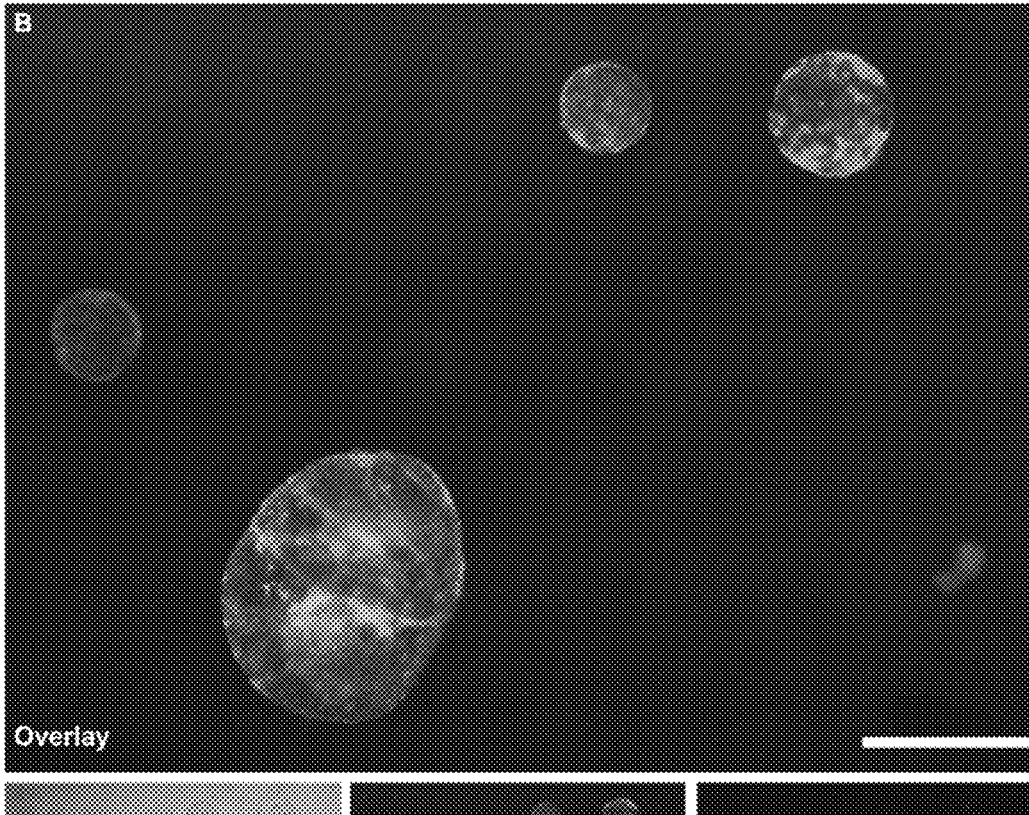
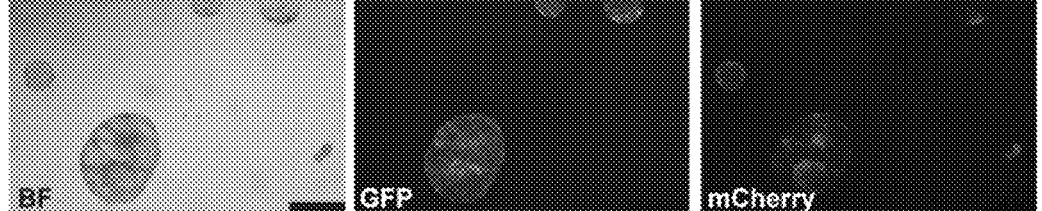
Fig. 7B

Fig. 8A
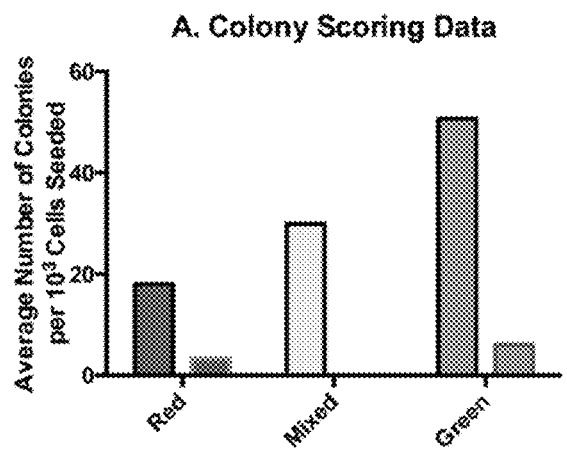
Fig. 8B
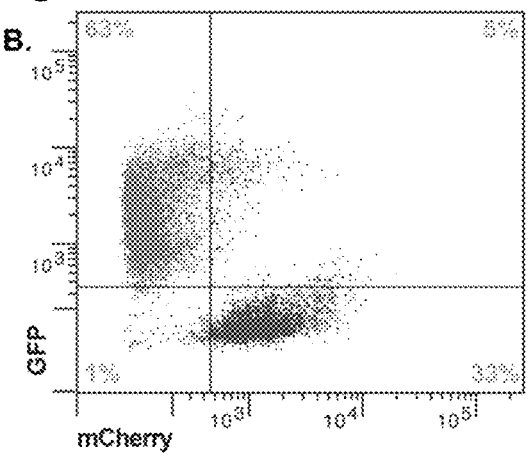
Fig. 8C
Fig. 9
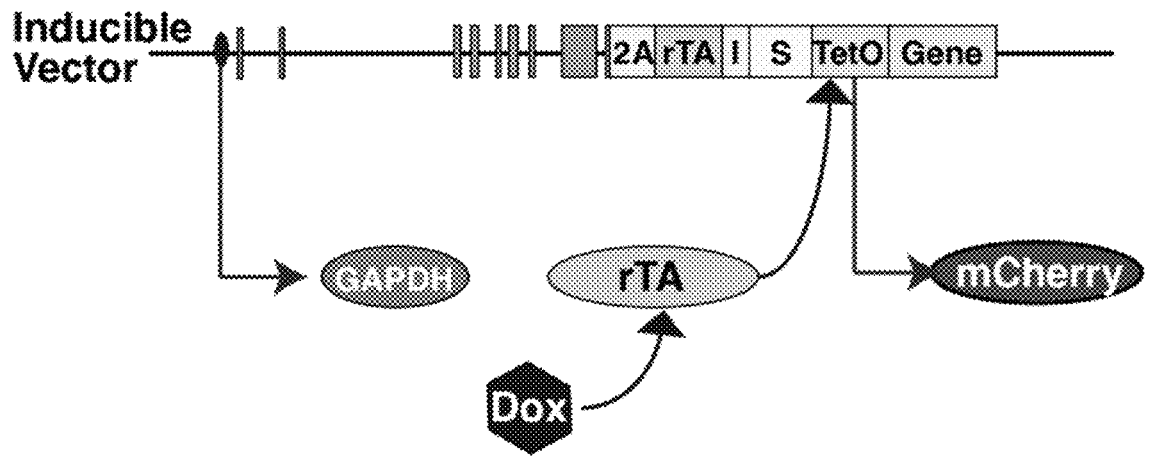

Fig. 13A
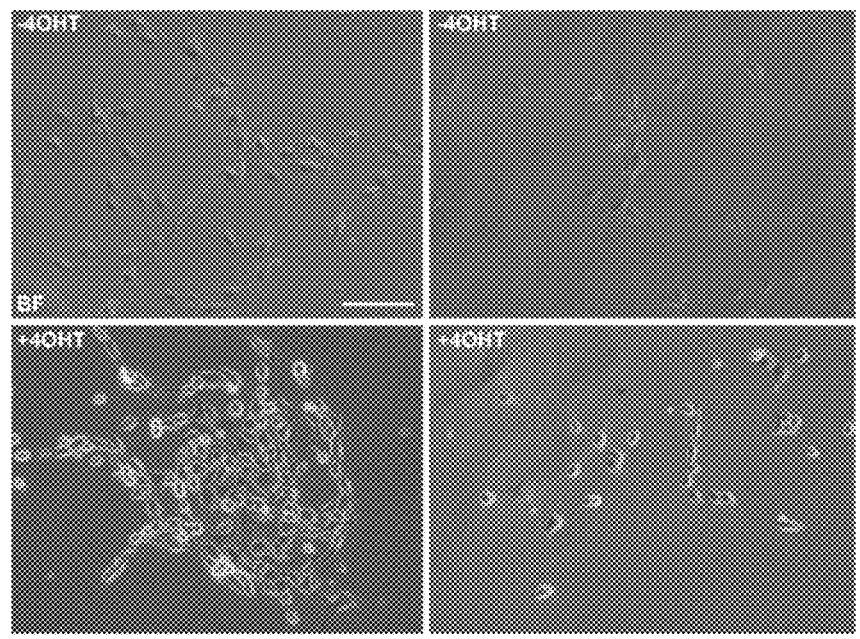
Fig. 13B
Fig. 14A
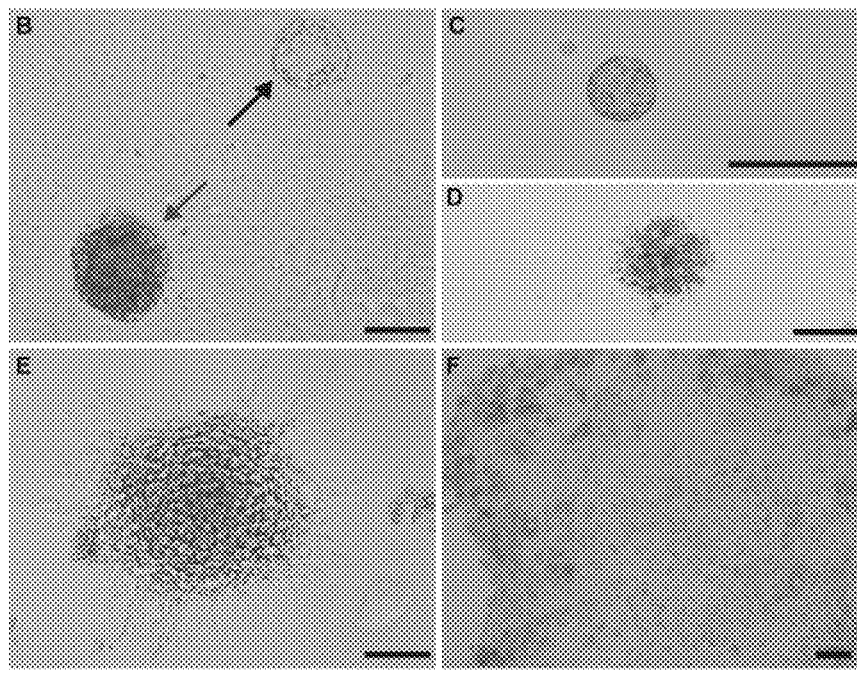
Fig. 14B
Fig. 14C
Fig. 14D
Fig. 14E
Fig. 14F

```
cgtggcggcgggTCCGGAGGAGAGGGCAGAGGAAGTCTTCTAACATGCGGTGACGTGGAGGAGAATCCTGGCCCAAT
```

Figure 17 (SEQ ID NO: 1)

```
gggaaggtgaaggtcggagtcaacgggtgagttcgcgggtggctgggggcgccctgggctgcgaccgcccccgaaccgcgtcta
cgagccttgcgggctccgggtctttgcagtcgtatgggggcagggtagctgttccccgcaaggagagctcaaggtcagcgctc
ggacctggcggagccccgcacccaggctgtggcgccctgtgcagctccgcccttgcggcgccatctgcccggagcctccttcc
cctagtccccagaaacaggaggtccctactcccgcccgagatcccgacccggaccccctaggtggggggacgctttcttcctt
cgcgctctgcggggtcacgtgtcgcagaggagcccctcccccacggcctccggcaccgcaggcccgggatgctagtgcgcag
cgggtgcatcctgtccggatgctgcgcctgcggtagagcggccgccatgttgcaaccgggaaggaaatgaatgggcagccgt
taggaaagcctgccggtgactaaccctgcgctcctgcctcgatgggtggagtcgcgtgtggcggggaagtcaggtggagcgag
gctagctggcccgatttctcctccgggtgatgcttttcctagattattctctggtaaatcaaagaagtgggtttatggaggtc
ctcttgtgtccctccccgcagaggtgtggtggctgtggcatggtgccaagccgggagaagctgagtcatgggtagttggaaa
aggacatttccaccgcaaaatggcccctctggtggtggccccttcctgcagcgccggctcacctcacggccccgcccttcccc
tgccagcctagcgttgacccgaccccaaaggccaggctgtaaatgtcaccgggaggattgggtgtctgggcgcctcggggaac
ctgcccttctcccattccgtcttccggaaaccagatctccaccgcaccctggtctgaggttaaatatagctgctgacctt
ctgtagctgggggcctgggctggggctctctcccatcccttctccccacacacatgcacttacctgtgctcccactcctgatt
tctggaaaagagctaggaaggacaggcaacttggcaaatcaaagccctgggactagggggttaaaatacagcttccctctc
ccacccgccccagtctctgtcccttttgtaggagggacttagagaaggggtgggcttgccctgtccagttaatttctgacctt
tactcctgcccttgagtttgatgatgctgagtgtacaagcgttttctccctaaagggtgcagctgagctaggcagcagcaag
cattcctggggtggcatagtggggtggtgaataccatgtacaaagcttgtgcccagactgtgggtggcagtgccccacatggc
cgcttctcctggaagggcttcgtatgactgggggtgttgggcagccctggagccttcagttgcagccatgccttaagccaggc
cagcctggcagggaagctcaagggagataaaattcaacctcttgggccctcctgggggtaaggagatgctgcattcgccctct
taatggggaggtggcctagggctgctcacatattctggaggagcctcccctcctcatgccttcttgcctcttgtctcttagat
ttggtcgtattgggcgcctggtcaccagggctgcttttaactctggtaaagtggatattgttgccatcaatgaccccttcatt
gacctcaactacatggtgagtgctacatggtgagccccaaagctggtgtgggaggagccacctggctgatgggcagcccttc
ataccctcacgtattccccaggtttacatgttccaatatgattccacccatggcaaattccatggcaccgtcaaggctgaga
acgggaagcttgtcatcaatggaaatcccatcaccatcttccaggagtgagtggaagacagaatggaagaaatgtgctttggg
gaggcaactaggatggtgtggctcccttgggtatatggtaaccttgtgtccctcaatatggtcctgtcccatctcccccca
ccccataggcgagatccctccaaaatcaagtggggcgatgctggcgctgagtacgtcgtggagtccactggcgtcttcacca
ccatggagaaggctggggtgagtgcaggagggcccgcgggagggaagctgactcagccctgcaaaggcaggacccgggttca
taactgtctgcttctgctgtaggctcatttgcaggggggagccaaaagggtcatcatctctgcccctctgctgatgcccc
catgttcgtcatgggtgtgaaccatgagaagtatgacaacagcctcaagatcatcaggtgaggaaggcagggcccgtggagaa
gcggccagcctggcacccatggacacgctcccctgacttgcgcccgctccctctttctttgcagcaatgcctcctgcacca
ccaactgcttagcacccctggccaaggtcatccatgacaactttggtatcgtggaaggactcatggtatgagagctggggaat
gggactgaggctcccacctttctcatccaagactggctcctccctgccggggctgcgtgcaaccctggggttggggttctgg
ggactggctttcccataatttccttcaaggtggggagggaggtagaggggtgatgtggggagtacgctgcagggcctcactc
cttttgcagaccacagtccatgccatcactgccacccagaagactgtggatggcccctccgggaaactgtggcgtgatggccg
cggggctctccagaacatcatccctgcctctactggcgctgccaaggctgtgggcaaggtcatccctgagctgaacgggaagc
tcactggcatggcctttcgtgtccccactgccaacgtgtcagtggtggacctgacctgccgtctagaaaaacctgccaaatat
gatgacatcaagaaggtggtgaagcaggcgtcggagggccccctcaagggcatcctgggctacactgagcaccaggtggtctc
ctctgacttcaacagcgacacccactcctccacctttgacgctggggctggcattgccctcaacgaccactttgtcaagctca
tttcctggtatgtggctgggccagagactggctcttaaaaagtgcagggtctggcgccctctggtggctggctcagaaaaag
ggccctgacaactcttttcatcttctaggtatgacaacgaatttggctacagcaacagggtggtggacctcatggcccacatg
gcctccaaggagggaaTG
```

Figure 18 (SEQ ID NO: 2)

aagaggaagagagagaccctcactgctggggagtccctgccacactcagtcccccaccacactgaatctcccctcctcacagt
tgccatgtagacccCttgaagagGggagGggcctagggagccgcaccttgtcatgtaccatcaataaagtaccctgtgctcaa
ccagttacttgtcctgtcttattctagggtctggggcagaggggagggaagctgggcttgtgtcaaggtgagacattcttgct
ggggagggacctggtatgttctcctcagactgagggtagggcctccaaacagccttgcttgcttcgagaaccattgcttccc
gctcagacgtcttgagtgctacaggaagctggcaccactacttcagagaacaaggccttttcctctcctcgctccagtcctag
gctatctgctgttggccaaacatggaagaagctattctgtgggcagccccagggaggctgacaggtggaggaagtcagggctc
gcactgggctctgacgctgactggttagtggagctcagcctggagctggagctgcagcgggcaattccagcttggcctccgcag
ctgtgaggtcttgagcacgtgctctattgctttctgtgccctcgtgtcttatctgaggacatcgtggccagccccctaaggtct
tcaagcaggattcatctaggtaaaccaagtacctaaaaccatgcccaaggcggtaaggactatataatgtttaaaaatcggta
aaaatgcccacctcgcatagttttgaggaagatgaactgagatgtgtcagggtgacttatttccatcatcgtccttaggggaa
cttgggtaggGgcaaggcgtgtagctgggacctaggtccagaccCctggctctgccactgaacggctcagttgctttgggcag
ttactcccgggcctcactttgcacgtgtgcttacctagtggagacaaaagtacatacctcggtagagcgcgcacgcctgtaac
cccagcactttgggaggccaaggtgggtgtatcacctgaggtcaggagtttgagaccagcctggccaacatggtgaaactccg
tctctactaaaattacaaaaatcagccaggcttcatggcacatgcctatagtcccagctacaggcatgctgaagcaggagaat
cgcttgcaccccggaggcagaggctgcagtgagctgagaccacaccactgcactccagcctaggcaacagagtatgagactcc
atctcaaaaaaaaaaaagtacctacctcagagttcaaactagtgaatattaggaagtgcttgagacagtgacaccaaagtgc
acaataaatactcgccagtttcattattattaaagaatccatttgaatgtcagctcaacacagcctcctataccgaggcattg
tgaaccgcatctccccagcttctccaggcttttccaagaatcagggacactgtagcctgttggtctcagtgtatgacagacac
ggaggaagcacatctttagctgatacttaaacagagaccctgagcgcacatacacccgcgcacacatgcatggagcttcacct
tctctgtcattctgcagtgaccaggagagcaagagctcccacctcccttcaaaacactgtgcccatcccgggcactaaggcct
ctttaaagcacggcacctccacgaggGaggGccacagccacatacactccacctggcaggtggacagcgtgagcacgtggacc
atagcagggacaaggtgccccggccagccccaacgccctctgccgctgacagggacagaagccctctccagctgcgtgtgctg
cagaggccatgcgtagcctccagctgcattctattccactccagtgcctgggccagttagcaccagtgtggaagacagtgagc
tggctccggacaacagggatggaggaaaggtcccacattcacattcctgatacgtggacaaggtgaggggccgcaatcgctct
ggcagcattttaaagatggggaagtagcagacacccacgcgtgaaggcaggagagccccaactgtggtggaaatggcccccaga
atggtagggccaagcctagctccagacaccccagagccctggagaagcaagactgagggagaaagcctgagggaggagcgcc
ccagtccccagggaccggcctggtgcagagctgcagctgatgttccctctgtgcagccccacctctgcctcgctgagctcc
ctgctgcgagggcctcggGtgcaaggGggaggcaggtctctatctcatggagctgtcagatgagacatcgcgatcggagtcct
cagcctcgcttggcggcggcggcgggtcgctaagcgggaccgcagtgaaagcaggagactttctagaaaaaaaacaccagttgt
caaccttggggcaggcaggaatcctgaagacggacggcactcctcctcctgctgcctcaccctctggcagcccgtgagaagta
ccggaagcgagggcggggccgcgggatggcgagggagcggcagggactgaactctctccaaacccaccctgacagggaaatgg
gccccgcctgtgtcttgggaactcagaggctgaggtcaggcatgatggctcacgcctgtaattccagcactttggGaggcaga
ggcgggtggatcacgacgtcaggagttcaaggcaagcctggccaacatggtgaaacCccatctctactaaaaatgcaaaaatt
agccaggtgtggtggcgggcgccttggaggctgaggcaagataatcacttgaacctgggaggcggaggttgtagtgagccaaa
aaaaaaaaaaaagaaatagctgaagtcacagtaggagagaagctgctgagcctccagcaccctgactctagggccttggctt
tatgtctatctgcagtattttttgtgattttaaaaattcactttcttgttgcggtgtaacttacacagggtcaaatgcacaaa
tcatggccctgactttagataaaaatctgcccccacaacccttctgttccttgccagttttaaactgcctctaaccagggga
accaccagagctggtggccttgggaggtttcagccctcccgtcatgaatggacatagctcatccaactgccaagggagagagc
tgtgggtctggccagccccaccaggtaactcccaaagggcagccccacagcaagatgtgacccagtcattgcctgagggtct
ctggggctgtgttccaacctttctccccgctgtgtcccctggaaggccccatgcccaggggaggcgcctaccggtctccaga
ctgggtgatgagccggcggcaggtctccatctgcacgtccaggccgcgcttcatgctgcacatctccatgtactcgtgcaggt
gccggttcatgtcgttcttggccgtggccaactccagctgtggtggggcaggcagggccatcggggttaacaggtggcgttca
cagcgcctctgttgccccgccaggaggccaacacgccaagagcagtggctgggccgggggcccaggcagccattactgaagg
ctcagattttaaaataaaccagaccaaggcagaaggcagcgaatacaccattgtttcctctgcttttcctggaaatctttgcc
tatggaggaatgcaaaggtactgctgcaggctgtgttcttttaagactgataagagtggtgaggaaagtcagtgtgggcggga
tggagcagatccacaggctcccagggccacacaggttcctatgggcccggctcaccCctcatccCctgtactgcgctggtcc
tgggctgtcccctcactgcactgtgagctcccgtaagggttagcgacaggttttcctcatcctggcagacccagacctcgaag
ggaattaactctctctgtgacccgtggcatacaagcctggctaactgctgaaagggcccaatcctcttaccattctctccctt
atcactttatttttctcacctaaaagccattttcagacactaaaaggaagactcccatattggaggtgccattgattctgagac
ctgtcctgatttcagaaatgtcacacgtggaaaacacgggctcagaatcaaagaaatccggtctccctccccgggcccattc
tgcagcccacactctgaggcaggcggagaggcagggcccaggcagcacaaactcagtgccagggacagtcgaTTAATTAAGCG
ATC Figure 19 (SEQ ID NO: 3)

CCCCCCCTAACGTTACTGGCCGAAGCCGCTTGGAATAAGGCCGGTGTGCGTTTGTCTATATGTTATTTTCCACCATATTGCCG
TCTTTTGGCAATGTGAGGGCCCGGAAACCTGGCCCTGTCTTCTTGACGAGCATTCCTAGGGGTCTTTCCCCTCTCGCCAAAGG
AATGCAAGGTCTGTTGAATGTCGTGAAGGAAGCAGTTCCTCTGGAAGCTTCTTGAAGACAAACAACGTCTGTAGCGACCCTTT
GCAGGCAGCGGAACCCCCCACCTGGCGACAGGTGCCTCTGCGGCCAAAAGCCACGTGTATAAGATACACCTGCAAAGGCGGCA
CAACCCCAGTGCCACGTTGTGAGTTGGATAGTTGTGGAAAGAGTCAAATGGCTCTCCTCAAGCGTATTCAACAAGGGGCTGAA
GGATGCCCAGAAGGTACCCCATTGTATGGGATCTGATCTGGGGCCTCGGTACACATGCTTTACATGTGTTTAGTCGAGGTTAA
AAAAACGTCTAGGCCCCCCGAACCACGGGGACGTGGTTTTCCTTTGAAAAACACGATGATAATATGGCCACAACCATG

Figure 20 (SEQ ID NO: 4)

```
GATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACA
GGAAACAGCTATGACCATGATTACGCCAAGCTCGAAATTAACCCTCACTAAAGGGAACAAAAGCTGGTACGTTAATtaaaggg
aaggtgaaggtcggagtcaacggtgagttcgcgggtggctgggggccctgggctgcgaccgccccgaaccgcgtctacga
gccttgcgggctccgggtctttgcagtcgtatggggcagggtagctgttccccgcaaggagagctcaaggtcagcgctcgga
cctggcggagcccgcacccaggctgtggcgccctgtgcagctccgcccttgcggcgccatctgcccggagcctccttcccct
agtccccagaaacaggaggtccctactcccgcccgagatcccgacccggacccctaggtgggggacgctttctttcctttcgc
gctctgcggggtcacgtgtcgcagaggagcccctcccccacggcctccggcaccgcaggccccgggatgctagtgcgcagcgg
gtgcatcctgtccggatgctgcgcctgcggtagagcggccgccatgttgcaaccgggaaggaaatgaatgggcagccgttag
gaaagcctgccggtgactaaccctgcgctcctgcctcgatgggtggagtcgcgtgtggcggggaagtcaggtggagcgaggct
agctggcccgatttctcctccgggtgatgcttttcctagattattctctggtaaatcaaagaagtgggtttatggaggtcctc
ttgtgtccctccccgcagaggtgtggtggctgtggcatggtgccaagccgggagaagctgagtcatgggtagttggaaaagg
acatttccaccgcaaaatggcccctctggtggtggcccttcctgcagcgccggctcacctcacggcccgcccttcccctgc
cagcctagcgttgacccgaccccaaaggccaggctgtaaatgtcaccgggaggattgggtgtctgggcgcctcggggaacctg
cccttctcccattccgtcttccggaaaccagatctcccaccgcaccctggtctgaggttaaatatagctgctgacctttctg
tagctgggggcctgggctggggctctctcccatccctctccccacacacatgcacttacctgtgctcccactcctgatttct
ggaaaagagctaggaaggacaggcaacttggcaaatcaaagccctgggactaggggggttaaaatacagcttccccctcttccca
cccgcccagtctctgtccttttgtaggagggacttagagaaggggtgggcttgcctgtccagttaatttctgaccttac
tcctgccctttgagtttgatgatgctgagtgtacaagcgttttctccctaaagggtgcagctgagctaggcagcagcaagcat
tcctggggtggcatagtggggtggtgaataccatgtacaaagcttgtgcccagactgtgggtggcagtgccccacatggccgc
ttctcctggaagggcttcgtatgactggggtgttgggcagccctggagccttcagttgcagccatgccttaagccaggccag
cctggcagggaagctcaagggagataaaattcaacctcttgggccctcctgggggtaaggagatgctgcattcgccctcttaa
tggggaggtggcctagggctgctcacatattctggaggagcctcccctcctcatgccttcttgcctcttgtctcttagatttg
gtcgtattgggcgcctggtcaccagggctgcttttaactctggtaaagtggatattgttgccatcaatgaccccttcattgac
ctcaactacatggtgagtgctacatggtgagcccaaagctggtgtgggaggagccacctggctgatgggcagcccttcata
ccctcacgtattccccaggtttacatgttccaatatgattccacccatggcaaattccatggcaccgtcaaggctgagaacg
ggaagcttgtcatcaatggaaatcccatcaccatcttccaggagtgagtggaagacagaatggaagaaatgtgctttggggag
gcaactaggatggtgtggctcccttgggtatatggtaaccttgtgtccctcaatatggtcctgtccccatctcccccccaccc
ccataggcgagatccctccaaaatcaagtggggcgatgctggcgctgagtacgtcgtggagtccactggcgtcttccaccaca
tggagaaggctggggtgagtgcaggagggcccgcgggagggaagctgactcagccctgcaaaggcaggacccgggttcataa
ctgtctgcttctctgctgtaggctcatttgcaggggggagccaaaagggtcatcatctctgcccctctgctgatgccccat
gttcgtcatgggtgtgaaccatgagaagtatgacaacagcctcaagatcatcaggtgaggaaggcagggcccgtggagaagcg
gccagcctggcaccctatggacacgctcccctgacttgcgcccgctccctctttctttgcagcaatgcctcctgcaccacca
actgcttagcacccctggccaaggtcatccatgacaactttggtatcgtggaaggactcatggtatgagagctggggaatggg
actgaggctccacctttctcatccaagactggctcctccctgccggggctgcgtcaaccctgggttggggtctgggga
ctggctttcccataatttcctttcaaggtggggaggagtagaggggtgatgtgggagtacgctgcagggcctcactcctt
ttgcagaccacagtccatgccatcactgccacccagaagactgtggatggcccctccgggaaactgtggcgtgatggccgcgg
ggctctccagaacatcatccctgcctctactggcgctgccaaggctgtgggcaaggtcatccctgagctgaacgggaagctca
ctggcatggccttccgtgtccccactgccaacgtgtcagtggtggacctgacctgccgtctagaaaaacctgccaaatatgat
gacatcaagaaggtggtgaagcaggcgtcggagggcccccctcaagggcatcctgggctacactgagcaccaggtggtctcctc
tgacttcaacagcgacacccactcctccaccttgacgctgggggctggcattgccctcaacgaccactttgtcaagctcattt
cctggtatgtggctggggccagagactggctcttaaaaagtgcagggtctggcgccctctggtggctggctcagaaaaaggc
cctgacaactcttttcatcttctaggtatgacaacgaatttggctacagcaacagggtggtggacctcatggcccacatggcc
tccaaggagggaaTGGcgcgtggcggcgggTCCGGAGGAGAGGGCAGAGGAAGTCTTCTAACATGCGGTGACGTGGAGGAGAA
TCCTGGCCCAATGGTGAGCAAGGGCGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGCTTCAGCCGCTACCCCGACCACATGAA
GCAGCACGACTTCTTCAAGTCCGCCATGCCCGAAGGCTACGTCCAGGAGCGCACCATCTTCTTCAAGGACGACGGCAACTACA
AGACCCGCGCCGAGGTGAAGTTCGAGGGCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCAAAGACCCCAACGAGAAGCGCGATCAC
ATGGTCCTGCTGGAGTTCGTGACCGCCGCCGGGATCACTCTCGGCATGGACGAGCTGTACAAGTAAGGATCCGCCCCTCTCCC
TCCCCCCCCCCTAACGTTACTGGCCGAAGCCGCTTGGAATAAGGCCGGTGTGCGTTTGTCTATATGTTATTTTCCACCATATT
GCCGTCTTTTGGCAATGTGAGGGCCCGGAAACCTGGCCCTGTCTTCTTGACGAGCATTCCTAGGGGTCTTTCCCCTCTCGCCA
AAGGAATGCAAGGTCTGTTGAATGTCGTGAAGGAAGCAGTTCCTCTGGAAGCTTCTTGAAGACAAACAACGTCTGTAGCGACC
CTTTGCAGGCAGCGGAACCCCCACCTGGCGACAGGTGCCTCTGCGGCCAAAAGCCACGTGTATAAGATACACCTGCAAAGGC
GGCACAACCCCAGTGCCACGTTGTGAGTTGGATAGTTGTGGAAAGAGTCAAATGGCTCTCCTCAAGCGTATTCAACAAGGGGC
TGAAGGATGCCCAGAAGGTACCCCATTGTATGGGATCTGATCTGGGGCCTCGGTACACATGCTTTACATGTGTTTAGTCGAGG
TTAAAAAAACGTCTAGGCCCCCCGAACCACGGGGACGTGGTTTTCCTTTGAAAAACACGATGATAATATGGCCACAACCATGG
CGCGTGGGATTGAACAAGATGGATTGCACGCAGGTTCTCCGGCCGCTTGGGTGGAGAGGCTATTCGGCTATGACTGGGCACAA
CAGACAATCGGCTGCTCTGATGCCGCCGTGTTCCGGCTGTCAGCGCAGGGGCGCCCGGTTCTTTTTGTCAAGACCGACCTGTC
CGGTGCCCTGAATGAACTGCAGGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTCCTGTCATCTCACCTTGCTCCT
```

Figure 21 (SEQ ID NO: 5)

```
GCCGAGAAAGTATCCATCATGGCTGATGCAATGCGGCGGCTGCATACGCTTGATCCGGCTACCTGCCCATTCGACCACCAAGC
GAAACATCGCATCGAGCGAGCACGTACTCGGATGGAAGCCGGTCTTGTCGATCAGGATGATCTGGACGAAGAGCATCAGGGGC
TCGCGCCAGCCGAACTGTTCGCCAGGCTCAAGGCGCGCATGCCCGACGGCGAGGATCTCGTCGTGACCCATGGCGATGCCTGC
TTGCCGAATATCATGGTGGAAAATGGCCGCTTTTCTGGATTCATCGACTGTGGCCGGCTGGGTGTGGCGGACCGCTATCAGGA
CATAGCGTTGGCTACCCGTGATATTGCTGAAGAGCTTTGCGGCGAATGGGCTGACCGCTTCCTCGTGCTTTACGGTATCGCCG
CTCCCGATTCGCAGCGCATCGCCTTCTATCGCCTTCTTGACGAGTTCTTCTGAGGGGATCGATCCGCTGTAAGTCTGCAGAAA
TTGATGATCTATTAAACAATAAAGATGTCCACTAAAATGGAAGTTTTTTACTGTCATACTTTGTTAAGAAGGGTGAGAACAGA
GTACCTACATTTTGAATGGAAGGATTGGAGCTACGGGGTGGGGGTGGGGGTGGGATTAGATAAATGCCTGCTCTTTACTGAA
GGCTCTTTACTATTGCTTTATGATAATGTTTCATAGTTGGATATCATAATTTAAACAAGCAAAACCAAATTAAGGGCCAGCTC
ATTCCTCCACTCATGATCTATAGATCTATAGATCTCTCGGGGGATCATTGTTTTTTTCTTGATTCCCACTTTGTGGTTCTAAG
TACTGTGGTTTCCAAATGTGTCAGTTTCATAGCCTGAAGAACGAGATCAGCAGCCTCTGTTCCACATACACTTCATTCTCAGT
ATTGTTTTGCCAAGTTCTAATTCCATCAGAAGCTGACTatCGATAAGCTTAgatcgagcacaagaggaagagagagaccctca
ctgctggggagtccctgccacactcagtcccccaccacactgaatctcccctcctcacagttgccatgtagaccccttgaaga
ggggaggggcctagggagccgcaccttgtcatgtaccatcaataaagtaccctgtgctcaaccagttacttgtcctgtcttat
tctagggtctggggcagaggggagggaagctgggcttgtgtcaaggtgagacattcttgctggggagggacctggtatgttct
cctcagactgagggtagggcctccaaacagccttgcttgcttcgagaaccatttgcttcccgctcagacgtcttgagtgctac
aggaagctggcaccactacttcagagaacaaggccttttcctctcctcgctccagtcctaggctatctgctgttggccaaaca
tggaagaagctattctgtgggcagccccagggaggctgacaggtggaggaagtcagggctcgcactgggctctgacgctgact
ggttagtggagctcagcctggagctgagctgcagcgggcaattccagcttggcctccgcagctgtgaggtcttgagcacgtgc
tctattgctttctgtgccctcgtgtcttatctgaggacatcgtggccagccctaaggtcttcaagcaggattcatctaggta
aaccaagtacctaaaaccatgcccaaggcggtaaggactatataatgtttaaaaatcggtaaaaatgcccacctcgcatagtt
ttgaggaagatgaactgagatgtgtcagggtgacttatttccatcatcgtccttaggggaacttgggtaggggcaaggcgtgt
agctgggacctaggtccagaccctggctctgccactgaacggctcagttgctttgggcagttactcccgggcctcactttgc
acgtgtgcttacctagtggagacaaaagtacatacctcggtagagcgcgcacgcctgtaaccccagcactttgggaggccaag
gtgggtgtatcacctgaggtcaggagtttgagaccagcctggccaacatggtgaaactccgtctctactaaaattacaaaaat
cagccaggcttcatggcacatgcctatagtcccagctacaggcatgctgaagcaggagaatcgcttgcaccccggaggcagag
gctgcagtgagctgagaccacaccactgcactccagcctaggcaacagagtatgagactccatctcaaaaaaaaaaaagtac
ctacctcagagttcaaactagtgaatattaggaagtgcttgagacagtgacaccaaagtgcacaataaatactcgccagtttc
attattattaaagaatccatttgaatgtcagctcaacacagcctcctataccgaggcattgtgaaccgcatctcccagcttc
tccaggctttttccaagaatcagggacactgtagcctgttggtctcagtgtatgacagacacggaggaagcacatccttagctg
atacttaaacagagaccctgagcgcacatacacccgcgcacacatgcatggagcttcaccttctctgtcattctgcagtgacc
aggagagcaagagctcccacctccctcaaaaacactgtgcccatcccgggcactaaggcctcttaaagcacggcacctccac
gagggagggccacagccacatacactccacctggcaggtggacagcgtgagcacgtggaccatagcagggacaaggtgccccg
gccagccccaacgccctctgccgctgacagggacagaagccctctccagctgcgtgtgctgcagaggccatgcgtagcctcca
gctgcattctattccactccagtgcctgggccagttagcaccagtgtggaagacagtgagctggctccggacaacagggatgg
aggaaaggtcccacattcacattcctgatacgtggacaaggtgaggggccgcaatcgctctggcagcattttaaagatgggga
agtagcagacacccacgcgtgaaggcaggagagccccaactgtggtggaaatggccccagaatggtagggccaagcctagctc
cagacacccagagccctggagaagccaagactgagggagaaagcctgagggaggagcgccccagtcccagggaccggcctg
gtgcagagctgcagctgatgttcccctctgtgcagcccaccctctgcctcgctgagctccctgctgcgagggcctcgggtgc
aaggggaggcaggtctctatctcatggagctgtcagatgagacatcgcgatcggagtcctcagcctcgcttggcggcggcgg
cgggtcgctaagcgggaccgcagtgaaagcaggagactttctagaaaaaaaacaccagttgtcaaccttggggcaggcaggaat
cctgaagacggacggcactcctcctcctgctgcctcaccctctggcagcccgtgagaagtaccggaagcgagggcgggccgc
gggatggcgagggagcggcagggactgaactctctccaaaccccaccctgacagggaaatgggcccgcctgtgtcctgggaac
tcagaggctgaggtcaggcatgatggctcacgcctgtaattccagcactttgggaggcagaggcgggtggatcacgacgtcag
gagttcaaggcaagcctggccaacatggtgaaacccatctctactaaaaatgcaaaaattagccaggtgtggtggcgggcgc
cttggaggctgaggcaagataatcacttgaacctgggaggcggaggttgtagtgagccaaaaaaaaaaaaaaagaaatagct
gaagtcacagtaggagagaagctgctgagcctccagcaccctgactctagggccttggctttatgtctatctgcagtattttt
gtgattttttaaaaattcactttcttgttgcggtgtaacttacacagggtcaaatgcacaaatcatggccctgactttagataa
aaatctgccccacaaccttctgttccttgccagtttttaaactgcctctaaccaggggaaccaccagagctggtggccttg
ggaggtttcagccctcccgtcatgaatggacatagctcatccaactgccaagggagagagctgtgggtctgggccagccccac
caggtaactcccaaagggcagcccacagcaagatgtgacccagtcattgcctgagggtctctggggctgtgttccaaccttt
ctccccgctgtgtcccctggaaggccccatgcccaggggaggcgcctaccggtctccagactgggtgatgagccggcggcag
gtctccatctgcacgtccaggccgcgcttcatgctgcacatctccatgtactcgtgcaggtgccggttcatgtcgttcttggc
cgtggccaactccagctgtggtggggcaggcagggccatcgggcttaacaggtggcgttcacagccgcctctgttgccccgcc
aggaggccaacacgccaagagcagtggctgggccggggggcccaggcagccattactgaaggctcagattttaaaataaaccag
accaaggcagaaggcagcgaatacaccattgtttcctctgcttttcctggaaatcttttgcctatggaggaatgcaaaggtact
gctgcaggctgtgttcttttaagactgataagagtggtgaggaaagtcagtgtgggcgggatggagcagatccacaggctccc
agggccacacaggttcctatgggcccggctcacccctcatccctgtactgcgctggtcctgggctgtcccctcactgcact
gtgagctcccgtaagggttagcgacaggttttcctcatcctggcagacccagacctcgaagggaattaactctctctgtgacc
cgtggcatacaagcctggctaactgctgaaagggccccaatcctcttaccattctctccttatcactttattttctcacctaa
aagccattttcagacactaaaggaagactcccatattggaggtgccattgattctgagacctgtcctgatttcagaaatgtc
acacgtggaaaacacggggctcagaatcaaagaaatccggtctccctccccgggcccattctgcagcccacactctgaggcag
gcggagaggcagggcccaggcagcacaaactcagtgccagggacagtcgaTTAATTAAGCGATCGCAGGCCGCCCGCGGTGga
gctccaattcgccctatagtgagtcgtattacgcgcgctcactggccgtcgttttacaacgtcgtgactgggaaaaccctggc
```

Figure 21 continued (SEQ ID NO: 5 continued)

```
Gttacccaacttaatcgccttgcagcacatccccctttcgccagctggcgtaatagcgaagaggcccgcaccgatcgcccttc
ccaacagttgcgcagcctgaatggcgaatggaaattgtaagcgttaatattttgttaaaattcgcgttaaattttttgttaaat
cagctcatttttttaaccaataggccgaaatcggcaaaatcccttataaatcaaaagaatagaccgagataggggttgagtgttg
ttccagtttggaacaagagtccactattaaagaacgtggactccaacgtcaaagggcgaaaaaccgtctatcagggcgatggc
ccactacgtgaaccatcaccctaatcaagttttttggggtcgaggtgccgtaaagcactaaatcggaaccctaaagggagccc
ccgatttagagcttgacggggaaagccggcgaacgtggcgagaaaggaagggaagaaagcgaaaggagcgggcgctagggcgc
tggcaagtgtagcggtcacgctgcgcgtaaccaccacacccgccgcgcttaatgcgccgctacagggcgcgtcag
```

Figure 21 continued (SEQ ID NO: 5 continued)

```
GATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACA
GGAAACAGCTATGACCATGATTACGCCAAGCTCGAAATTAACCCTCACTAAAGGGAACAAAAGCTGGTACGTTAATtaaaggg
aaggtgaaggtcggagtcaacgggtgagttcgcgggtggctgggggggccctgggctgcgaccgccccgaaccgcgtctacga
gccttgcgggctccgggtctttgcagtcgtatgggggcagggtagctgttccccgcaaggagagctcaaggtcagcgctcgga
cctggcggagccccgcacccaggctgtggcgccctgtgcagctccgcccctttgcggcgccatctgcccggagcctccttcccct
agtccccagaaacaggaggtccctactcccgcccgagatcccgacccggaccctaggtgggggacgctttcttttcctttcgc
gctctgcggggtcacgtgtcgcagaggagcccctcccccacggcctccggcaccgcaggccccgggatgctagtgcgcagcgg
gtgcatccctgtccggatgctgcgcctgcggtagagcggccgccatgttgcaaccgggaaggaaatgaatgggcagccgttag
gaaagcctgccggtgactaaccctgcgctcctgcctcgatgggtggagtcgcgtgtggcggggaagtcaggtggagcgaggct
agctggcccgatttctcctccgggtgatgcttttcctagattattctctggtaaatcaaagaagtgggtttatggaggtcctc
ttgtgtccccctccccgcagaggtgtggtggctgtggcatggtgccaagccgggagaagctgagtcatgggtagttggaaaagg
acatttccaccgcaaaatggcccctctggtggtggccccttcctgcagcgccggctcacctcacggcccgcccttcccctgc
cagcctagcgttgacccgaccccaaaggccaggctgtaaatgtcaccgggaggattgggtgtctgggcgcctcggggaacctg
cccttctcccattccgtcttccggaaaccagatctcccaccgcaccctggtctgaggttaaatatagctgctgaccttctg
tagctgggggcctgggctgggctctctcccatcccttctcccacacacatgcacttacctgtgctcccactcctgatttct
ggaaaagagctaggaaggacaggcaacttggcaaatcaaagccctgggactaggggttaaaatacagcttccccttccca
cccgcccagtctctgtcccttttgtaggagggacttagagaaggggtgggcttgccctgtccagttaatttctgacctttac
tcctgccctttgagtttgatgatgctgagtgtacaagcgttttctccctaaaggggtgcagctgagctaggcagcagcaagcat
tcctggggtggcatagtggggtggtgaataccatgtacaaagcttgtgcccagactgtgggtggcagtgccccacatggccgc
ttctcctggaagggcttcgtatgactggggtgttgggcagccctggagccttcagttgcagccatgccttaagccaggccag
cctggcagggaagctcaagggagataaaattcaacctcttgggccctcctgggggtaaggagatgctgcattcgcctcttaa
tggggaggtggcctagggctgctcacatattctggaggagcctcccctcctcatgccttcttgcctcttgtctcttagatttg
gtcgtattgggcgcctggtcaccagggctgcttttaactctggtaaagtggatattgttgccatcaatgacccctcattgac
ctcaactacatggtgagtgctacatggtgagcccaaagctggtgtgggaggagccacctggctgatggcagcccttcata
ccctcacgtattccccaggtttacatgttccaatatgattccacccatggcaaattccatggcaccgtcaaggctgagaacg
ggaagcttgtcatcaatggaaatcccatcaccatcttccaggagtgagtggaagacagaatggaagaaatgtgcttggggag
gcaactaggatggtgtggctcccttgggtatatggtaaccttgtgtccctcaatatggtcctgtcccatctcccccccaccc
ccataggcgagatccctccaaaatcaagtggggcgatgctggcgctgagtacgtcgtggagtccactggcgtcttcaccacca
tggagaaggctggggtgagtcaggaggggcccgcgggagggaagctgactcagccctgcaaaggcaggacccggggttcataa
ctgtctgcttctctgctgtaggctcattgcagggggagccaaaagggtcatcatctctgccccctctgctgatgcccccat
gttcgtcatgggtgtgaaccatgagaagtatgacaacagcctcaagatcatcaggtgaggaaggcagggcccgtggagaagcg
gccagcctggcaccctatggacacgctcccctgacttgcgcccgctccctctttctttgcagcaatgcctcctgcaccacca
actgcttagcacccctggccaaggtcatccatgacaactttggtatcgtggaaggactcatggtatgagagctggggaatggg
actgaggctcccacctttctcatccaagactggctcctccctgccgggctgcgtgcaaccctggggttgggggttctgggga
ctggctttcccataatttcctttcaaggtggggaggaggtagaggggtgatgtggggagtacgctgcagggcctcactcctt
ttgcagaccacagtccatgccatcactgccacccagaagactgtggatggccctccgggaaactgtggcgtgatggccgcgg
ggctctccagaacatcatccctgcctctactggcgctgccaaggctgtgggcaaggtcatccctgagctgaacgggaagctca
ctggcatggccttccgtgtccccactgccaacgtgtcagtggtggacctgacctgccgtctagaaaaacctgccaaatatgat
gacatcaagaaggtggtgaagcaggcgtcggagggcccctcaagggcatcctgggctacactgagcaccaggtggtctcctc
tgacttcaacagcgacacccactcctccaccttttgacgctgggctggcattgccctcaacgaccactttgtcaagctcattt
cctggtatgtggctggggccagagactggctcttaaaaagtgcagggtctggcgccctctggtggctggctcagaaaagggc
cctgacaactcttttcatcttctaggtatgacaacgaatttggctacagcaacagggtggtggacctcatggcccacatggcc
tccaaggagggaaTGGcgcgtggccggcgggTCCGGAGGAGAGGGCAGAGGAAGTCTTCTAACATGCGGTGACGTGGAGGAGAA
TCCTGGCCCAATGGTGAGCAAGGGCGAGGAGGATAACATGGCCATCATCAAGGAGTTCATGCGCTTCAAGGTGCACATGGAGG
GCTCCGTGAACGGCCACGAGTTCGAGATCGAGGGCGAGGGCGAGGGCCGCCCCTACGAGGGCACCCAGACCGCCAAGCTGAAG
GTGACCAAGGGTGGCCCCCTGCCCTTCGCCTGGGACATCCTGTCCCCTCAGTTCATGTACGGCTCCAAGGCCTACGTGAAGCA
CCCCGCCGACATCCCCGACTACTTGAAGCTGTCCTTCCCCGAGGGCTTCAAGTGGGAGCGCGTGATGAACTTCGAGGACGGCG
GCGTGGTGACCGTGACCCAGGACTCCTCCCTGCAGGACGGCGAGTTCATCTACAAGGTGAAGCTGCGCGGCACCAACTTCCCC
TCCGACGGCCCCGTAATGCAGAAGAAGACCATGGGCTGGGAGGCCTCCTCCGAGCGGATGTACCCCGAGGACGGCGCCCTGAA
GGGCGAGATCAAGCAGAGGCTGAAGCTGAAGGACGGCGGCCACTACGACGCTGAGGTCAAGACCACCTACAAGGCCAAGAAGC
```

Figure 22 (SEQ ID NO: 6)

```
CCGTGCAGCTGCCCGGCGCCTACAACGTCAACATCAAGTTGGACATCACCTCCCACAACGAGGACTACACCATCGTGGAACAG
TACGAACGCGCCGAGGGCCGCCACTCCACCGGCGGCATGGACGAGCTGTACAAGTCTAGATCATAATCAGCGGATCCGCCCCT
CTCCCTCCCCCCCCCCTAACGTTACTGGCCGAAGCCGCTTGGAATAAGGCCGGTGTGCGTTTGTCTATATGTTATTTTCCACC
ATATTGCCGTCTTTTGGCAATGTGAGGGCCCGGAAACCTGGCCCTGTCTTCTTGACGAGCATTCCTAGGGGTCTTTCCCCTCT
CGCCAAAGGAATGCAAGGTCTGTTGAATGTCGTGAAGGAAGCAGTTCCTCTGGAAGCTTCTTGAAGACAAACAACGTCTGTAG
CGACCCTTTGCAGGCAGCGGAACCCCCCACCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTCAAATGGCTCTCCTCAAGCGTATTCAACAA
GGGGCTGAAGGATGCCCAGAAGGTACCCCATTGTATGGGATCTGATCTGGGGCCTCGGTACACATGCTTTACATGTGTTTAGT
CGAGGTTAAAAAAACGTCTAGGCCCCCCGAACCACGGGGACGTGGTTTTCCTTTGAAAAACACGATGATAATATGGCCACAAC
CATGGCGCGTATGGCTCGGGGCATTGAACAGGATGGGCTGCACGCCGGGTCACCTGCTGCTTGGGTCGAAAGACTGTTTGGGT
ATGATTGGGCTCAGCAGACAATCGGCTGCTCTGACGCCGCCGTGTTCAGGCTGAGTGCTCAGGGACGCCCCGTGCTGTTTGTC
AAGACTGACCTGTCAGGGGCACTGAACGAGCTGCAGGATGAGGCAGCCCGCCTGAGCTGGCTGGCAACCACAGGAGTGCCTTG
TGCTGCAGTCCTGGACGTGGTCACTGAGGCCGGACGAGATTGGCTGCTGCTGGGAGAAGTGCCAGGACAGGACCTGCTGAGCT
CCCACCTGGCACCAGCTGAGAAGGTCTCCATCATGGCAGATGCCATGGAGACTGCATACTCTGGACCCCGCCACCTGCCCT
TTCGATCACCAGGCTAAACATCGCATTGAGCGGGCTCGCACACGAATGGAAGCAGGCCTGGTGGACCAGGACGATCTGGATGA
GGAACACCAGGGACTGGCTCCTGCAGAGCTGTTTGCAAGGCTGAAAGCCAGAATGCCAGACGGCGAAGATCTGGTGGTCACCC
ATGGAGACGCTTGCCTGCCCAACATCATGGTGGAGAATGGAAGATTCAGTGGGTTTATTGATTGTGGCCGACTGGGAGTCGCC
GACAGGTACCAGGATATCGCCCTGGCTACAAGAGACATTGCAGAGGAACTGTGCGGGGAATGGGCCGATCGGTTCCTGGTGCT
GTATGGCATTGCTGCTCCCGACAGTCAGAGGATTGCTTTTTACAGGCTGCTGGACGAGTTCTTTTGAATCTAGAcgcgCCcgc
gtacAAGGGCGAATTCCAGCACACTGGCGGCCGTTACTAGTGGATCCGAGCTCGgtacatCGATAAGCTTAgatcgagcacaa
gaggaagagagagaccctcactgctggggagtccctgccacactcagtcccccaccacactgaatctcccctcctcacagttg
ccatgtagaccccttgaagaggggagggcctagggagccgcaccttgtcatgtaccatcaataaagtaccctgtgctcaacc
agttacttgtcctgtcttattctagggtctggggcagaggggagggaagctgggcttgtgtcaaggtgagacattcttgctgg
ggagggacctggtatgttctcctcagactgagggtagggcctccaaacagccttgcttgcttcgagaaccatttgcttcccgc
tcagacgtcttgagtgctacaggaagctggcaccactacttcagagaacaaggccttttcctctcctcgctccagtcctaggc
tatctgctgttggccaaacatggaagaagctattctgtgggcagccccagggaggctgacaggtggaggaagtcagggctcgc
actgggctctgacgctgactggttagtggagctcagcctggagctgagctgcagcggcaattccagcttggcctccgcagct
gtgaggtcttgagcacgtgctctattgctttctgtgccctcgtgtcttatctgaggacatcgtggccagccctaaggtcttc
aagcaggattcatctaggtaaaccaagtacctaaaaccatgcccaaggcggtaaggactatataatgtttaaaaatcggtaaa
aatgcccacctcgcatagttttgaggaagatgaactgagatgtgtcagggtgacttatttccatcatcgtccttagggaact
tgggtagggcaaggcgtgtagctgggaccaggtccagacccctggctctgccactgaacggctcagttgctttgggcagtt
actcccgggcctcactttgcacgtgtgcttacctagtggagacaaaagtacatacctcggtagagcgcgcacgcctgtaaccc
cagcactttgggaggccaaggtgggtgtatcacctgaggtcaggagtttgagaccagcctggccaacatggtgaaactccgtc
tctactaaaattacaaaaatcagccaggcttcatggcacatgcctatagtcccagctacaggcatgctgaagcaggagaatcg
cttgcaccccggaggcagaggctgcagtgagctgagaccacaccactgcactccagcctaggcaacagagtatgagactccat
ctcaaaaaaaaaaaaagtacctacctcagagttcaaactagtgaatattaggaagtgcttgagacagtgacaccaaagtgcac
aataaatactcgccagtttcattattattaaagaatccatttgaatgtcagctcaacacagcctcctataccgaggcattgtg
aaccgcatctccccagcttctccaggcttttccaagaatcagggacactgtagcctgttggtctcagtgtatgacagacacgg
aggaagcacatctttagctgatacttaaacagagaccctgagcgcacatacacccgcgcacacatgcatggagcttcaccttc
tctgtcattctgcagtgaccaggagagcaagagctcccacctcccttcaaaacactgtgcccatcccgggcactaaggcctct
ttaaagcacggcacctccacgagggagggccacagccacatacactccacctggcaggtggacagcgtgagcacgtggaccat
agcagggacaaggtgccccggccagccccaacgccctctgccgctgacagggacagaagccctctccagctgcgtgtgctgca
gaggccatgcgtagcctccagctgcattctattccactccagtgcctgggccagttagcaccagtgtggaagacagtgagctg
gctccggacaacagggatggaggaaaggtcccacattcacattcctgatacgtggacaaggtgaggggccgcaatcgctctgg
cagcatttttaaagatggggaagtagcagacacccacgcgtgaaggcaggagagccccaactgtggtggaaatggcccagaat
ggtagggccaagcctagctccagacaccccagagccctggagaagccaagactgagggagaaagcctgagggaggagcgcccc
agtccccagggaccggcctggtgcagagctgcagctgatgttcccctctgtgcagccccaccctctgcctcgctgagctccct
gctgcgagggcctcggtgcaaggggaggcaggtctctatctcatggagctgtcagatgagacatcgcgatcggagtcctca
gcctcgcttggcggcggcggcgggtcgctaagcgggaccgcagtgaaagcaggagactttctagaaaaaaacaccagttgtca
accttggggcaggcaggaatcctgaagacggacggcactcctcctcctgctgcctcaccctctggcagcccgtgagaagtacc
ggaagcgagggcggggccgcgggatggcgagggagcggcagggactgaactctctccaaacccaccctgacagggaaatgggc
cccgcctgtgtcttgggaactcagaggctgaggtcaggcatgatggctcacgcctgtaattccagcactttgggaggcagagg
cgggtggatcacgacgtcaggagttcaaggcaagcctggccaacatggtgaaaccccatctctactaaaaatgcaaaaattag
ccaggtgtggtggcgggcgccttggaggctgaggcaagataatcacttgaacctgggaggcggaggttgtagtgagccaaaaa
aaaaaaaaaagaaatagctgaagtcacagtaggagagaagctgctgagcctccagcacccctgactctagggcctcggcttta
tgtctatctgcagtatttttgtgattttttaaaaattcactttcttgttgcggtgtaacttacacagggtcaaatgcacaaatc
atggccctgactttagataaaaatctgccccacaacccttctgttccttgccagttttttaaactgcctctaaccaggggaac
caccagagctggtggccttgggaggtttcagccctcccgtcatgaatggacatagctcatccaactgccaagggagagagctg
tgggtctgggccagccccaccaggtaactcccaaagggcagcccacagcaagatgtgacccagtcattgcctgagggtctct
ggggctgtgttccaacctttctccccgctgtgtccccctggaaggccccatgcccaggggaggcgcctaccggtctccagact
gggtgatgagccggcggcaggtctccatctgcacgtccaggccgcgcttcatgctgcacatctccatgtactcgtgcaggtgc
cggttcatgtcgttcttggccgtggccaactccagctgtggtggggcaggcagggccatcggggttaacaggtggcgttcaca
gcgcctctgttgccccgccaggaggccaacacgccaagagcagtggctgggccgggggcccaggcagccattactgaaggct
cagattttaaaataaaccagaccaaggcagaaggcagcgaatacaccattgtttcctctgcttttcctggaaatctttgccta
```

Figure 22 continued (SEQ ID NO: 6 continued)

```
tggaggaatgcaaaggtactgctgcaggctgtgttcttttaagactgataagagtggtgaggaaagtcagtgtgggcgggatg
gagcagatccacaggctcccagggccacacaggttcctatggggcccggctcacccctcatccctgtactgcgctggtcctg
ggctgtcccctcactgcactgtgagctcccgtaagggttagcgacaggttttcctcatcctggcagacccagacctcgaaggg
aattaactctctctgtgacccgtggcatacaagcctggctaactgctgaaaggggcccaatcctcttaccattctctccttat
cactttattttctcacctaaaagccattttcagacactaaaaggaagactcccatattggaggtgccattgattctgagacct
gtcctgatttcagaaatgtcacacgtggaaaacacggggctcagaatcaaagaaatccggtctccctccccgggcccattctg
cagcccacactctgaggcaggcggagaggcagggcccaggcagcacaaactcagtgccagggacagtcgaTTAATTAAGCGAT
CGCAGGCCGCCCGCGGTGgagctccaattcgccctatagtgagtcgtattacgcgcgctcactggccgtcgttttacaacgtc
gtgactgggaaaaccctggcgttacccaacttaatcgccttgcagcacatcccccttttcgccagctggcgtaatagcgaagag
gcccgcaccgatcgcccttcccaacagttgcgcagcctgaatggcgaatggaaattgtaagcgttaatattttgttaaaattc
gcgttaaattttttgttaaatcagctcatttttttaaccaataggccgaaatcggcaaaatcccttataaatcaaaagaatagac
cgagatagggttgagtgttgttccagtttggaacaagagtccactattaaagaacgtggactccaacgtcaaagggcgaaaaa
ccgtctatcagggcgatggcccactacgtgaaccatcaccctaatcaagttttttggggtcgaggtgccgtaaagcactaaat
cggaaccctaaagggagcccccgatttagagcttgacggggaaagccggcgaacgtggcgagaaaggaagggaagaaagcgaa
aggagcgggcgctagggcgctggcaagtgtagcggtcacgctgcgcgtaaccaccacacccgccgcgcttaatgcgccgctac
agggcgcgtcag
```

Figure 22 continued (SEQ ID NO: 6 continued)

```
GATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACA
GGAAACAGCTATGACCATGATTACGCCAAGCTCGAAATTAACCCTCACTAAAGGGAACAAAAGCTGGTACGTTAATtaaggaa
ggtgaaggtcggagtcaacgggtgagttcgcgggtggctgggggcccctgggctgcgaccgccccgaaccgcgtctacgagc
cttgcgggctccgggtctttgcagtcgtatggggcagggtagctgttccccgcaaggagagctcaaggtcagcgctcggacc
tggcggagcccgcacccaggctgtggcgccctgtgcagctccgcccttgcggcgccatctgcccggagcctccttcccctag
tccccagaaacaggaggtccctactcccgcccgagatcccgacccggacccctaggtgggggacgctttcttttccttcgcgc
tctgcgggtcacgtgtcgcagaggagcccctcccccacggcctccggcaccgcaggccccgggatgctagtgcgcagcgggt
gcatccctgtccggatgctgcgcctgcggtagagcggccgccatgttgcaaccgggaaggaaatgaatgggcagccgttagga
aagcctgccggtgactaaccctgcgctcctgcctcgatgggtggagtcgcgtgtggcggggaagtcaggtggagcgaggctag
ctggcccgatttctcctccgggtgatgcttttcctagattattctctggtaaatcaaagaagtgggtttatggaggtcctctt
gtgtcccctccccgcagaggtgtggtggctgtggcatggtgccaagccgggagaagctgagtcatgggtagttggaaaaggac
atttccaccgcaaaatggcccctctggtggtggcccttcctgcagcgccggctcacctcacggcccgcccttcccctgcca
gcctagcgttgacccgaccccaaaggccaggctgtaaatgtcaccgggaggattgggtgtctgggcgcctcggggaacctgcc
cttctccccattccgtcttccggaaaccagatctcccaccgcaccctggtctgaggttaaatatagctgctgaccttctgta
gctgggggcctgggctggggctctctcccatcccttctcccacacacatgcacttacctgtgctcccactcctgatttctgg
aaaagagctaggaaggacaggcaacttggcaaatcaaagccctgggactagggggttaaaatacagcttccctcttcccacc
cgccccagtctctgtcccttttgtaggagggacttagagaaggggtgggcttgccctgtccagttaatttctgacctttactc
ctgcccctttgagtttgatgatgctgagtgtacaagcgttttctccctaaagggtgcagctgagctaggcagcagcaagcattc
ctggggtggcatagtggggtggtgaataccatgtacaaagcttgtgcccagactgtgggtggcagtgccccacatggccgctt
ctcctggaagggcttcgtatgactggggtgttgggcagccctggagccttcagttgcagccatgccttaagcaggccagcc
tggcagggaagctcaaggagataaaattcaacctcttgggccctcctgggggtaaggagatgctgcattcgccctcttaatg
gggaggtggcctagggctgctcacatattctggaggagcctcccctcctcatgccttcttgcctcttgtctcttagatttggt
cgtattgggcgcctggtcaccagggctgcttttaactctggtaaagtggatattgttgccatcaatgaccccttcattgacct
caactacatggtgagtgctacatggtgagcccaaagctggtgtgggaggagccacctggctgatgggcagcccttcatacc
ctcacgtattccccaggtttacatgttccaatatgattccacccatggcaaattccatggcaccgtcaaggctgagaacggg
aagcttgtcatcaatggaaatcccatcaccatcttccaggagtgagtggaagacagaatggaagaaatgtgctttggggaggc
aactaggatggtgtggctccctttgggtatatggtaaccttgtgtccctcaatatggtcctgtccccatctcccccaccccc
ataggcgagatccctccaaaatcaagtggggcgatgctggcgtcgagtacgtcgtggagtccactgcgtcttcaccaccatg
gagaaggctggggtgagtgcaggagggcccgcggagggaagctgactcagccctgcaaaggcaggacccgggttcataact
gtctgcttctctgctgtaggctcatttgcaggggggagccaaaagggtcatcatctctgcccctctgctgatgcccccatgt
tcgtcatgggtgtgaaccatgagaagtatgacaacagcctcaagatcatcaggtgaggaaggcagggcccgtggagaagcggc
cagcctggcacccatggacacgctcccctgacttgcgccccgctccctctttctttgcagcaatgcctcctgcaccaccaac
tgcttagcacccctggccaaggtcatccatgacaactttggtatcgtggaaggactcatggtatgagagctggggaatgggac
tgaggctcccacctttctcatccaagactggctcctccctgccggggctgcgtgcaaccctgggttggggttctggggact
ggctttcccataatttcctttcaaggtggggaggaggtagagggtgatgtggggagtacgctgcagggcctcactccttt
gcagaccacagtccatgccatcactgccacccagaagactgtggatggcccctccgggaaactgtggcgtgatggccgcgggg
ctctccagaacatcatccctgcctctactggcgctgccaaggctgtgggcaaggtcatccctgagctgaacgggaagctcact
ggcatggccttccgtgtccccactgccaacgtgtcagtggtggacctgacctgccgtctagaaaacctgccaaatatgatga
catcaagaaggtggtgaagcaggcgtcggagggcccctcaagggcatcctgggctacactgagcaccaggtggtctcctctg
acttcaacagcgacacccactcctccacctttgacgctggggctggcattgccctcaacgaccactttgtcaagctcatttcc
```

Figure 23 (SEQ ID NO: 7)

```
tggtatgtggctggggccagagactggctcttaaaaagtgcagggtctggcgccctctggtggctggctcagaaaaagggccc
tgacaactcttttcatcttctaggtatgacaacgaatttggctacagcaacagggtggtggacctcatggcccacatggcctc
caaggagggaaTGGcgcgtggcggcgggTCCGGAGGAGAGGGCAGAGGAAGTCTTCTAACATGCGGTGACGTGGAGGAGAATC
CTGGCCCGGCGCGTCGCGTCTCGACCACCatgccoctcaacgttagcttcaccaacaggaactatgacctcgactacgactcg
gtgcagccgtatttctactgcgacgaggaggagaacttctaccagcagcagcagcagagcgagctgcagccccggcgcccag
cgaggatatctggaagaaattcgagctgctgcccaccccgccctgtccctagccgccgctccgggctctgctcgcctcct
acgttgcggtcacaccttctcccttcggggagacaacgacggcggtggcgggagcttctccacggccgaccagctggagtg
gtgaccgagctgctgggaggagacatggtgaaccagagtttcatctgcgacccggacgacgagaccttcatcaaaaacatcat
catccaggactgtatgtggagcggcttctcggccgccgccaagctcgtctcagagaagctggcctcctaccaggctgcgcgca
aagacagcggcagcccgaaccccgcccgcggccacagcgtctgctccacctccagcttgtacctgcaggatctgagcgccgcc
gcctcagagtgcatcgaccctcggtggtcttccctaccctctcaacgacagcagctcgcccaagtcctgcgcctcgcaaga
ctccagcgccttctctccgtcctcggattctctgctctcctcgacggagtcctccccgcagggcagcccgagccctggtgc
tccatgaggagacaccgccaccaccagcagcgactctgaggaggaacaagaagatgaggaagaaatcgatgttgtttctgtg
gaaaagaggcaggctcctggcaaaaggtcagagtctggatcaccttctgctggaggccacagcaaacctcctcacagcccact
ggtcctcaagaggtgccacgtctccacacatcagcacaactacgcagcgcctccctccactcggaaggactatcctgctgcca
agagggtcaagttggacagtgtcagagtcctgagacagatcagcaacaaccgaaaatgcaccagcccccaggtcctcggacacc
gaggagaatgtcaagaggcgaacacacaacgtcttggagcgccagaggaggaacgagctaaaacggagctattttgccctgcg
tgaccagatcccggagttggaaaacaatgaaaaggccccaaggtagttatccttaaaaaagccacagcatacatcctgtccg
tccaagcagaggagcaaaagctcatttctgaagaggacttgttgcggaaacgacgagaacagttgaaacacaaacttgaacag
ctacgggatccACGAAATGAAATGGGTGCTTCAGGAGACATGAGGGCTGCCAACCTTTGGCCAAGCCCTCTTGTGATTAAGCA
CACTAAGAAGAATAGCCCTGCCTTGTCCTTGACAGCTGACCAGATGGTCAGTGCCTTGTTGGATGCTGAACCGCCCATGATCT
ATTCTGAATATGATCCTTCTAGACCCTTCAGTGAAGCCTCAATGATGGGCTTATTGACCAACCTAGCAGATAGGGAGCTGGTT
CATATGATCAACTGGGCAAAGAGAGTGCCAGGCTTTGGGGACTTGAATCTCCATGATCAGGTCCACCTTCTCGAGTGTGCCTG
GCTGGAGATTCTGATGATTGGTCTCGTCTGGCGCTCCATGGAACACCCGGGGAAGCTCCTGTTTGCTCCTAACTTGCTCCTGG
ACAGGAATCAAGGTAAATGTGTGGAAGGCATGGTGGAGATCTTTGACATGTTGCTTGCTACGTCAAGTCGGTTCCGCATGATG
AACCTGCAGGGTGAAGAGTTTGTGTGCCTCAAATCCATCATTTTGCTTAATTCCGGAGTGTACACGTTTCTGTCCAGCACCTT
GAAGTCTCTGGAAGAGAAGGACCACATCCACCGTGTCCTGGACAAGATCACAGACACTTTGATCCACCTGATGGCCAAAGCTG
GCCTGACTCTGCAGCAGCAGCATCGCCGCCTAGCTCAGCTCCTTCTCATTCTTTCCCATATCCGGCATATGAGTAACAAACGC
ATGGAGCATCTCTACAACATGAAATGCAAAAACGTGGTACCCCTCTATGACCTGCTCCTGGAGATGTTGGATGCCCACCGCCT
TCATGCCCCAGCCAGTCGCATGGGAGTGCCCCCAGAGGAGCCCAGCCAGACCCAGCTGGCCACCACCAGCTCCACTTCAGCAC
ATTCCTTACAAACCTACTACATACCCCCGGAAGCAGAGGGCTTCCCCAACACGATCTGAGAGCTAGGTCGACGGATCCGCCCC
TCTCCCTCCCCCCCCCTAACGTTACTGGCCGAAGCCGCTTGGAATAAGGCCGGTGTGCGTTTGTCTATATGTTATTTTCCAC
CATATTGCCGTCTTTTGGCAATGTGAGGGCCCGGAAACCTGGCCCTGTCTTGACGAGCATTCCTAGGGGTCTTTCCCCTC
TCGCCAAAGGAATGCAAGGTCTGTTGAATGTCGTGAAGGAAGCAGTTCCTCTGGAAGCTTCTTGAAGACAAACAACGTCTGTA
GCGACCCTTTGCAGGCAGCGGAACCCCCCACCTGGCGACAGGTGCCTCTGCGGCCAAAAGCCACGTGTATAAGATACACCTGC
AAAGGCGGCACAACCCCAGTGCCACGTTGTGAGTTGGATAGTTGTGGAAAGAGTCAAATGGCTCTCCTCAAGCGTATTCAACA
AGGGGCTGAAGGATGCCCAGAAGGTACCCCATTGTATGGGATCTGATCTGGGGCCTCGGTACACATGCTTTACATGTGTTTAG
TCGAGGTTAAAAAAACGTCTAGGCCCCCCGAACCACGGGGACGTGGTTTTCCTTTGAAAAACACGATGATAATATGGCCACAA
CCATGGCGCGTATGAAAAAGCCCGAGCTGACTGCCACCTCTGTCGAGAAGTTCCTGATTGAAAAGTTTGATTCCGTGAGTGAC
CTGATGCAGCTGAGCGAGGGCGAGGAATCCCGGGCCTTCTCTTTTGACGTGGGCGGAAGGGGCTACGTGCTGAGAGTCAACTC
TTGCGCCGACGGATTCTATAAGGATCGCTACGTGTATCGACACTTTGCTAGTGCCGCTCTGCCCATCCCTGAGGTGCTGGACA
TTGGCGAGTTCAGCGAATCCCTGACATACTGTATCTCCAGGAGAGCCCAGGGAGTGACTCTGCAGGATCTGCCTGAGACCGAA
CTGCCTGCCGTGCTGCAGCCTGTGGCTGAAGCTATGGACGCTATCGCAGCCGCTGATCTGTCACAGACTAGCGGGTTCGGCCC
ATTTGGCCCCCAGGGAATTGGGCAGTACACCACATGGAGAGACTTTATCTGCGCAATTGCCGATCCCCACGTGTATCATTGGC
AGACAGTCATGGACGATACCGTGAGCGCCAGTGTCGCTCAGGCACTGGACGAGCTGATGCTGTGGGCAGAGGATTGTCCTGAA
GTGAGGCACCTGGTCCATGCTGACTTCGGGAGCAACAATGTGCTGACCATAACGGCAGAATCACAGCCGTCATTGACTGGAG
TGAGGCTATGTTTGGCGATTCACAGTACGAAGTGGCTAATATCTTCTTTTGGCGACCCTGGCTGGCATGCATGGAGCAGCAGA
CCCGCTATTTCGAGCGGCGCCATCCTGAACTGGCAGGGTCTCCAAGACTGCGGGCCTACATGCTGCGGATTGGCCTGGACCAG
CTGTATCAGAGCCTGGTGGATGGAAATTTTGACGATGCAGCATGGGCACAGGGGCGGTGCGACGCTATCGTGCGCAGCGGAGC
AGGAACTGTGGGAAGAACCCAGATTGCCCGAAGGTCCGCTGCAGTGTGGACAGATGGGTGCGTGGAGGTGCTGGCAGATAGCG
GAAATAGGAGACCAAGTACAAGACCACGGGCAAAAGAGTAATCTAGAcgcgtatcgatAAGCTTAgatcgagcacaagaggaa
gagagagaccctcactgctggggagtccctgccacactcagtcccccaccacactgaatctcccctcctcacagttgccatgt
agacccctttgaagaggggaggggcctagggagccgcaccttgtcatgtaccatcaataaagtaccctgtgctcaaccagttac
ttgtcctgtcttattctagggtctggggcagaggggagggaagctgggcttgtgtcaaggtgagacattcttgctggggaggg
acctggtatgttctcctcagactgagggtagggcctccaaacagccttgcttgcttcgagaaccatttgcttcccgctcagac
gtcttgagtgctacaggaagctggcaccactacttcagagaacaaggccttttcctctcctcgctccagtcctaggctatctg
ctgttggccaaacatggaagaagctattctgtgggcagcccagggaggctgacaggtggaggaagtcagggctcgcactggg
ctctgacgctgactggttagtggagctcagcctggagctgagctgcagcgggcaattccagcttggcctccgcagctgtgagg
tcttgagcacgtgctctattgctttctgtgccctcgtgtcttatctgaggacatcgtggccagcccctaaggtcttcaagcag
gattcatctaggtaaaccaagtacctaaaaccatgcccaaggcggtaaggactatataatgtttaaaaatcggtaaaaatgcc
cacctcgcatagttttgaggaagatgaactgagatgtgtcagggtgacttatttccatcatcgtccttagggggaacttgggta
ggggcaaggcgtgtagctgggacctaggtccagacccctggctctgccactgaacggctcagttgctttgggcagttactccc
gggcctcactttgcacgtgtgcttacctagtggagacaaaagtacatacctcggtagagcgcgcacgcctgtaacccagcac
```

Figure 23 continued (SEQ ID NO: 7 continued)

```
tttgggaggccaaggtgggtgtatcacctgaggtcaggagtttgagaccagcctggccaacatggtgaaactccgtctctact
aaaattacaaaaatcagccaggcttcatggcacatgcctatagtcccagctacaggcatgctgaagcaggagaatcgcttgca
ccccggaggcagaggctgcagtgagctgagaccacaccactgcactccagcctaggcaacagagtatgagactccatctcaaa
aaaaaaaaaagtacctacctcagagttcaaactagtgaatattaggaagtgcttgagacagtgacaccaaagtgcaaataaa
tactcgccagtttcattattattaaagaatccatttgaatgtcagctcaacacagcctcctataccgaggcattgtgaaccgc
atctccccagcttctccaggcttttccaagaatcagggacactgtagcctgttggtctcagtgtatgacagacacggaggaag
cacatctttagctgatacttaaacagagaccctgagcgcacatacacccgcgcacacatgcatggagcttcaccttctctgtc
attctgcagtgaccaggagagcaagagctcccacctcccttcaaaacactgtgcccatcccgggcactaaggcctcttcaaag
cacggcacctccacgagggagggccacagccacatacactccacctggcaggtggacagcgtgagcacgtggaccatagcagg
gacaaggtgccccggccagccccaacgccctctgccgctgacagggacagaagccctctccagctgcgtgtgctgcagaggcc
atgcgtagcctccagctgcattctattccactccagtgcctgggccagttagcaccagtgtggaagacagtgagctggctccg
gacaacagggatggaggaaaggtcccacattcacattcctgatacgtggacaaggtgaggggccgcaatcgctctggcagcat
tttaaagatggggaagtagcagacacccacgcgtgaaggcaggagagccccaactgtggtggaaatggcccagaatggtagg
gccaagcctagctccagacaccccagagccctggagaagccaagactgagggagaaagcctgagggaggagcgcccagtccc
cagggaccggcctggtgcagagctgcagctgatgttccctctgtgcagccccacctctgcctcgctgagctccctgctgcg
agggcctcgggtgcaaggggaggcaggtctctatctcatggagctgtcagatgagacatcgcgatcggagtcctcagcctcg
cttggcggcggcggcgggtcgctaagcgggaccgcagtgaaagcaggagactttctagaaaaaaaaccagttgtcaaccttg
gggcaggcaggaatcctgaagacggacggcactcctcctcctgctgcctcaccctctggcagcccgtgagaagtaccggaagc
gagggcggggccgcgggatggcgagggagcggcagggactgaactctctccaaacccaccctgacagggaaatgggccccgcc
tgtgtcttgggaactcagaggctgaggtcaggcatgatggctcacgcctgtaattccagcactttgggaggcagaggcgggtg
gatcacgacgtcaggagttcaaggcaagcctggccaacatggtgaaacccatctctactaaaaatgcaaaattagccaggt
gtggtggcgggcgccttggaggctgaggcaagataatcacttgaacctgggaggcggaggttgtagtgagcaaaaaaaaaa
aaaaagaaatagctgaagtcacagtaggagagaagctgctgagcctccagcaccctgactctagggccttggctttatgtcta
tctgcagtatttttgtgatttttaaaaattcactttcttgttgcggtgtaacttacacagggtcaaatgcacaaatcatggcc
ctgactttagataaaaatctgccccacaaccttctgttccttgccagttttaaactgcctctaaccaggggaaccaccag
agctggtggccttggaggtttcagccctcccgtcatgaatggacatagctcatccaactgccaagggagagagctgtgggtc
tgggccagccccaccaggtaactcccaaagggcagcccacagcaagatgtgacccagtcattgcctgagggtctctggggct
gtgttccaacctttctccccgctgtgtcccctggaaggccccatgcccaggggaggcgcctaccggtctccagactgggtga
tgagccggcggcaggtctccatctgcacgtccaggccgcgcttcatgctgcacatctccatgtactcgtgcaggtgccggttc
atgtcgttcttggccgtggccaactccagctgtggtggggcaggcagggccatcggggttaacaggtggcgttcacagccgcct
ctgttgccccgccaggaggccaacacgccaagagcagtggctgggccggggcccaggcagccattactgaaggctcagatt
ttaaaataaaccagaccaaggcagaaggcagcgaatacaccattgtttcctctgcttttcctggaaatctttgcctatggagg
aatgcaaaggtactgctgcaggctgtgttcttttaagactgataagagtggtgaggaaagtcagtgtgggcggatggagcag
atccacaggctcccagggccacacaggttcctatggggcccggctcacccctcatccctgtactgcgctggtcctgggctgt
cccctcactgcactgtgagctcccgtaaggggttagcgacaggttttcctcatcctggcagacccagacctcgaagggaattaa
ctctctctgtgacccgtggcatacaagcctggctaactgctgaaagggcccaatcctcttaccattctctccttatcacttt
attttctcacctaaaagccattttcagacactaaaaggaagactcccatattggaggtgccattgattctgagacctgtcctg
atttcagaaatgtcacacgtggaaaacacggggctcagaatcaaagaaatccggtctccctccccgggcccattctgcagccc
acactctgaggcaggcggagaggcagggcccaggcagcacaaactcagtgccagggacagtcgaTTAATTAAGCGATCGCAGG
CCGCCaCCGCGGTGgagctccaattcgccctatagtgagtcgtattacgcgcgctcactggccgtcgttttacaacgtcgtga
ctgggaaaaccctggcgttacccaacttaatcgccttgcagcacatccccctttcgccagctggcgtaatagcgaagaggccc
gcaccgatcgcccttcccaacagttgcgcagcctgaatggcgaatggaaattgtaagcgttaatattttgttaaaattcgcgt
taaattttgttaaatcagctcatttttaaccaataggccgaaatcggcaaaatcccttataaatcaaaagaatagaccgag
atagggttgagtgttgttccagtttggaacaagagtccactattaaagaacgtggactccaacgtcaaagggcgaaaaccgt
ctatcagggcgatggcccactacgtgaaccatcaccctaatcaagttttttggggtcgaggtgccgtaaagcactaaatcgga
accctaaagggagcccccgatttagagcttgacggggaaagccggcgaacgtggcgagaaaggaagggaagaaagcgaagga
gcgggcgctagggcgctggcaagtgtagcggtcacgctgcgcgtaaccaccacacccgccgcgcttaatgcgccgctacaggg
cgcgtcag
```

Figure 23 continued (SEQ ID NO: 7 continued)

```
GATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACA
GGAAACAGCTATGACCATGATTACGCCAAGCTCGAAATTAACCCTCACTAAAGGGAACAAAAGCTGGTACGTTAATtaaaggg
aaggtgaaggtcggagtcaacgggtgagttcgcgggtggctggggggccctgggctgcgaccgccccgaaccgcgtctacga
gccttgcgggctccggtctttgcagtcgtatggggcagggtagctgttccccgcaaggagagctcaaggtcagcgctcgga
cctggcggagcccgcacccaggctgtggcgccctgtcagctccgcccttgcggcgccatctgcccggagcctccttcccct
agtccccagaaacaggaggtccctactcccgcccgagatcccgaccggacccctaggtggggacgctttctttccttcgc
gctctgcgggtcacgtgtcgcagaggagcccctcccccacgcctccggcaccgcaggccccgggatgctagtgcgcagcgg
gtgcatccctgtccggatgctgcgcctgcggtagagcggccgccatgttgcaaccgggaaggaaatgaatgggcagccgttag
```

Figure 24 (SEQ ID NO: 8)

```
gaaagcctgccggtgactaaccctgcgctcctgcctcgatgggtggagtcgcgtgtggcggggaagtcaggtggagcgaggct
agctggcccgatttctcctccgggtgatgcttttcctagattattctctggtaaatcaaagaagtgggtttatggaggtcctc
ttgtgtccccctccccgcagaggtgtggtggctgtggcatggtgccaagccgggagaagctgagtcatgggtagttggaaaagg
acatttccaccgcaaaatggcccctctggtggtggccccttcctgcagcgccggctcacctcacggcccc gccctccccctgc
cagcctagcgttgacccgaccccaaaggccaggctgtaaatgtcaccgggaggattgggtgtctgggcgcctcggggaacctg
cccttctccccattccgtcttccggaaaccagatctcccaccgcaccctggtctgaggttaaatatagctgctgaccttctg
tagctgggggcctgggctggggctctctcccatcccttctcccacacacatgcacttacctgtgctcccactcctgatttct
ggaaaagagctaggaaggacaggcaacttggcaaatcaaagccctgggactaggggttaaaatacagcttccccctcttccca
cccgcccagtctctgtcccttttgtaggagggacttagagaaggggtgggcttgccctgtccagttaatttctgaccttac
tcctgcccttttgagtttgatgatgctgagtgtacaagcgttttctccctaaagggtgcagctgagctaggcagcagcaagcat
tcctgggtggcatagtggggtggtgaataccatgtacaaagcttgtgcccagactgtgggtggcagtgccccacatggccgc
ttctcctggaagggcttcgtatgactggggtgttgggcagccctggagccttcagttgcagccatgccttaagccaggccag
cctggcagggaagctcaagggagataaaattcaacctcttgggccctcctgggggtaaggagatgctgcattcgcctcttaa
tggggaggtggcctagggctgctcacatattctggaggagcctcccctcctcatgccttcttgcctcttgtctcttagatttg
gtcgtattgggcgcctggtcaccagggctgcttttaactctggtaaagtggatattgttgccatcaatgaccccttcattgac
ctcaactacatggtgagtgctacatggtgagccccaaagctggtgtgggaggagccacctggctgatgggcagcccttcata
ccctcacgtattccccaggtttacatgttccaatatgattccacccatggcaaattccatggcaccgtcaaggctgagaacg
ggaagcttgtcatcaatggaaatcccatcaccatcttccaggagtgagtggaagacagaatgaagaaatgtgcttggggag
gcaactaggatggtgtggctcccttgggtatatggtaaccttgtgtccctcaatatggtcctgtcccatctcccccccaccc
ccataggcgagatccctccaaaatcaagtggggcgatgctggcgctgagtacgtcgtggagtccactggcgtcttcaccacca
tggagaaggctgggtgagtgcaggagggcccgcggaggggaagctgactcagccctgcaaaggcaggacccggttcataa
ctgtctgcttctctgctgtaggctcatttgcagggggagccaaaagggtcatcatctctgccccctctgctgatgccccccat
gttcgtcatgggtgtgaaccatgagaagtatgacaacgacctcaagatcatcaggtgaggaaggcagggcccgtgggagaagcg
gccagcctggcacccta tggacacgctccc ctgacttgcgccc cgctccctctttc tttgcagcaatgcctcctgcaccacca
actgcttagcacccctggccaaggtcatccatgacaactttggtatcgtggaaggactcatggtatgagagctggggaatggg
actgaggctccaccttctcatccaagactggctcctccctgccggggctgcgtgcaaccctgggttgggggttctgggga
ctggctttcccataatttccttttcaaggtggggagggaggtagaggggtgatgtgggggagtacgctgcagggcctcactcctt
ttgcagaccacagtccatgccatcactgccacccagaagactgtggatggcccctcggggaaactgtggcgtgatggccgcgg
ggctctccagaacatcatccctgcctctactggcgctgccaaggctgtgggcaaggtcatccctgagctgaacgggaagctca
ctggcatggccttccgtgtccccactgccaacgtgtcagtggtggacctgacctgccgtctagaaaaacctgccaaatatgat
gacatcaagaaggtggtgaagcaggcgtcggagggcccc ctcaagggcatcctgggctacactgagcaccaggtggtctcctc
tgacttcaacagcgacacccactcctccacctttgacgctggggctggcattgccctcaacgaccactttgtcaagctcattt
cctggtatgtggctggggccagagactggctcttaaaaagtgcagggtctggcgccctctggtggctggctcagaaaaagggc
cctgacaactcttttcatcttctaggtatgacaacgaatttggctacagcaacagggtggtgg acctcatggcccacatggcc
tccaaggagggaaTGGcgcgtggcggcgggTCCGGAGGAGAGGGCAGAGGAAGTCTTCTAACATGCGGTGACGTGGAGGAGAA
TCCTGGCCCgGCGCGCCCCATGCCAAAGAGACCCAGACCCTCTAGATTAGATAAAAGTAAAGTGATTAACAGCGCATTAGAGC
TGCTTAATGAGGTCGGAATCGAAGGTTTAACAACCCGTAAACTCGCCCAGAAGCTTGGTGTAGAGCAGCCTACACTGTATTGG
CATGTAAAAAATAAGCGGGCTTTGCTCGACGCCTTAGCCATTGAGATGTTAGATAGGCACCATACTCACTTTTGCCCTTTAAA
AGGGGAAAGCTGGCAAGATTTTTTACGCAATAACGCTAAAAGTTTTAGATGTGCTTTACTAAGTCATCGCAATGGAGCAAAAG
TACATTCAGATACACGGCCTACAGAAAAACAGTATGAAACTCTCGAAAATCAATTAGCCTTTTTATGCCAACAAGGTTTTTCA
CTAGAGAACGCGTTATATGCACTCAGCGCTGTGGGGCATTTTACTTTAGGTTGCGTATTGGAAGATCAAGAGCATCAAGTCGC
TAAAGAAGAAAGGGAAACACCTACTACTGATAGTATGCCGCCATTATTACGACAAGCTATCGAATTATTTGATCACCAAGGTG
CAGAGCCAGCCTTCTTATTCGGCCTTGAATTGATCATATGCGGATTAGAAAAACAACTTAAATGTGAAAGTGGGTCCGCGTAC
AGCCGCGCGCGTACGAAAAACAATTACGGGTCTACCATCGAGGGCCTGCTCGATCTCCCGGACGACGACGCCCCGAAGAGGC
GGGGCTGGCGGCTCCGCGCCTGTCCTTTCTCCCCGCGGACACACGCGCAGACTGTCGACGGCCCCCCGACCGATGTCAGCC
TGGGGGACGAGCTCCACTTAGACGGCGGAGACGTGGCGCATGCCGACGCGCTAGACGATTTCGATCTGGACATGTTG
GGGGACGGGGATTCCCCGGGTCCGGGATTTACCCCCCACGACTCCGCCCCCTACGGCGCTCTGGATATGGCCGACTTCGAGTT
TGAGCAGATGTTTACCGATGCCCTTGGAATTGACGAGTACGGTGGGTAGGGGATCCGCCCCTCTCCCTCCCCCCCCCTAACG
TTACTGGCCGAAGCCGCTTGGAATAAGGCCGGTGTGCGTTTGTCTATATGTTATTTTCCACCATATTGCCGTCTTTTGGCAAT
GTGAGGGCCCGGAAACCTGGCCCTGTCTTCTTGACGAGCATTCCTAGGGGTCTTTCCCCTCTCGCCAAAGGAATGCAAGGTCT
GTTGAATGTCGTGAAGGAAGCAGTTCCTCTGGAAGCTTCTTGAAGACAAACAACGTCTGTAGCGACCCTTTGCAGGCAGCGGA
ACCCCCCACCTGGCGACAGGTGCCTCTGCGGCCAAAAGCCACGTGTATAAGATACACCTGCAAAGGCGGCACAACCCCAGTGC
CACGTTGTGAGTTGGATAGTTGTGGAAAGAGTCAAATGGCTCTCCTCAAGCGTATTCAACAAGGGGCTGAAGGATGCCCAGAA
GGTACCCCATTGTATGGGATCTGATCTGGGGCCTCGGTACACATGCTTTACATGTGTTTAGTCGAGGTTAAAAAAACGTCTAG
GCCCCCCGAACCACGGGGACGTGGTTTTCCTTTGAAAAACACGATGATAATATGGCCACAACCATGGCGCGTATGGCTCGGGG
CATTGAACAGGATGGGCTGCACGCCGGGTCACCTGCTGCTTGGGTCGAAAGACTGTTTGGGTATGATTGGGCTCAGCAGACAA
TCGGCTGCTCTGACGCCGCCGTGTTCAGGCTGAGTGCTCAGGGACGCCCCGTGCTGTTTGTCAAGACTGACCTGTCAGGGGCA
CTGAACGAGCTGCAGGATGAGGCAGCCCGCCTGAGCTGGCTGGCAACCACAGGAGTGCCTTGTGCTGCAGTCCTGGACGTGGT
CACTGAGGCCGGACAGATTGGCTGCTGGGAGAAGTGCCAGGACAGGACCTGCTGAGCTCCCACCTGGCACCAGCTGAGA
AGGTCTCCATCATGGCAGATGCCATGAGGAGACTGCATACTCTGGACCCCGCCACCTGCCCTTTCGATCACCAGGCTAAACAT
CGCATTGAGCGGGCTCGCACACGAATGGAAGCAGGCCTGGTGGACCAGGACGATCTGGATGAGGAACACCAGGGACTGGCTCC
TGCAGAGCTGTTTGCAAGGCTGAAAGCCAGAATGCCAGACGGCGAAGATCTGGTGGTCACCCATGGAGACGCTTGCCTGCCCA
ACATCATGGTGGAGAATGGAAGATTCAGTGGGTTTATTGATTGTGGCCGACTGGGAGTCGCCGACAGGTACCAGGATATCGCC
```

Figure 24 continued (SEQ ID NO: 8 continued)

```
CTGGCTACAAGAGACATTGCAGAGGAACTGTGCGGGGAATGGGCCGATCGGTTCCTGGTGCTGTATGGCATTGCTGCTCCCGA
CAGTCAGAGGATTGCTTTTTACAGGCTGCTGGACGAGTTCTTTTGAATCTAGAcgcgtatCGAACCAGACAtGATAAGATACA
TTGATGAGTTTGGACAAACCACAACTAGAATGCAGTGAAAAAAATGCTTTATTTGTGAAATTTGTGATGCTATTGCTTTATTT
GTAACCATTATAAGCTGCAATAAACAAGTTAACAACAACAATTGCATTCATTTTATGTTTCAGGTTCAGGGGGAGGTGTGGGA
GGTTTTTTAAAGCAAGTAAAACCTCTACAAATGTGGTATGGCTGATTATGATCCTGCAAGCCTCGTCGTCCTGGCCGGACCAC
GCTATCTGTGCAAGGTCCCCGGCCCCGGACGCGCGCTCCATGAGCAGAGCGCCCGCCGCCGAGGCGAAGACTCGGGCGGCGCC
CTGCCCGTCCCACCAGGTCAACAGGCGGTAACCGGCCTCTTCATCGGGAATGCGCGCGACCTTCAGCATCGCCGGCATGTCCC
CCTGGCGGACGGGAAGTATCCAGCTCGACCAAGCTTGGCGAGATTTTCAGGAGCTAAGGAAGCTTCGTCTTCACTCGAGTTTA
CTCCCTATCAGTCGATAGAGAACGTATGTCGAGTTTACTCCCTATCAGTGATAGAGAACGATGTCGAGTTTACTCCCTATCAGT
GATAGAGAACGTATGTCGAGTTTACTCCCTATCAGTGATAGAGAACGTATGTCGAGTTTACTCCCTATCAGTGATAGAGAACG
TATGTCGAGTTTATCCCTATCAGTGATAGAGAACGTATGTCGAGTTTACTCCCTATCAGTGATAGAGAACGTATGTCGAGGTA
GGCGTGTACGGTGGGAGGCCTATATAAGCAGAGCTCGTTTAGTGAACCGTCAGATCGCCTGGAAATCGATGCCACCATGGTGA
GCAAGGGCGAGGAGGATAACATGGCCATCATCAAGGAGTTCATGCGCTTCAAGGTGCACATGGAGGGCTCCGTGAACGGCCAC
GAGTTCGAGATCGAGGGCGAGGGCGAGGGCCGCCCCTACGAGGGCACCCAGACCGCCAAGCTGAAGGTGACCAAGGGTGGCCC
CCTGCCCTTCGCCTGGGACATCCTGTCCCCTCAGTTCATGTACGGCTCCAAGGCCTACGTGAAGCACCCCGCCGACATCCCCG
ACTACTTGAAGCTGTCCTTCCCCGAGGGCTTCAAGTGGGAGCGCGTGATGAACTTCGAGGACGGCGGCGTGGTGACCGTGACC
CAGGACTCCTCCCTGCAGGACGGCGAGTTCATCTACAAGGTGAAGCTGCGCGGCACCAACTTCCCCTCCGACGGCCCCGTAAT
GCAGAAGAAGACCATGGGCTGGGAGGCCTCCTCCGAGCGGATGTACCCCGAGGACGGCGCCCTGAAGGGCGAGATCAAGCAGA
GGCTGAAGCTGAAGGACGGCGGCCACTACGACGCTGAGGTCAAGACCACCTACAAGGCCAAGAAGCCCGTGCAGCTGCCCGGC
GCCTACAACGTCAACATCAAGTTGGACATCACCTCCCACAACGAGGACTACACCATCGTGGAACAGTACGAACGCGCCGAGGG
CCGCCACTCCACCGGCGGCATGGACGAGCTGTACAAGTCTAGATCATAATCAGCGGATCCATCGATGgatCCAAGCTTAgatc
gagcacaagaggaagagagagaccctcactgctggggagtccctgccacactcagtcccccaccacactgaatctccccctcct
cacagttgccatgtagaccccttgaagaggggagggggcctagggagccgcacccttgtcatgtaccatcaataaagtaccctgt
gctcaaccagttacttgtcctgtcttattctagggtctggggcagaggggagggaagctgggcttgtgtcaaggtgagacatt
cttgctggggagggacctggtatgttctcctcagactgagggtagggcctccaaacagccttgcttgcttcgagaaccatttg
cttcccgctcagacgtcttgagtgctacaggaagctggcaccactacttcagagaacaaggccttttcctctcctcgctccag
tcctaggctatctgctgttggccaaacatggaagaagctattctgtgggcagccccagggaggctgacaggtggaggaagtca
gggctcgcactgggctctgacgctgactggttagtggagctcagcctggagctgagctgcagcgggcaattccagcttggcct
ccgcagctgtgaggtcttgagcacgtgctctattgctttctgtgccctcgtgtcttatctgaggacatcgtggccagccccta
aggtcttcaagcaggattcatctaggtaaaccaagtacctaaaaccatgcccaaggcggtaaggactatataatgtttaaaaa
tcggtaaaaatgcccacctcgcatagttttgaggaagatgaactgagatgtgtcagggtgacttatttccatcatcgtcctta
ggggaacttgggtaggggcaaggcgtgtagctgggacctaggtccagacccctggctctgccactgaacggctcagttgcttt
gggcagttactcccgggcctcactttgcacgtgtgcttacctagtggagacaaaagtacatacctcggtagagcgcgcacgcc
tgtaaccccagcactttgggaggccaaggtgggtgtatcacctgaggtcaggagtttgagaccagcctggccaacatggtgaa
actccgtctctactaaaattacaaaaattcagccaggcttcatggcacatgcctatagtcccagctacaggcatgctgaagcag
gagaatcgcttgcaccccggaggcagaggctgcagtgagctgagacacaccactgcactccagcctaggcaacagagtatga
gactccatctcaaaaaaaaaaaaagtacctacctcagagttcaaactagtgaatattaggaagtgcttgagacagtgacacca
aagtgcacaataaatactcgccagtttcattattattaaagaatccatttgaatgtcagctcaacacagcctcctataccgag
gcattgtgaaccgcatctccccagcttctccaggcttttccaagaatcagggacactgtagcctgttggtctcagtgtatgac
agacacgaggaagcacatctttagctgatacttaaacagagaccctgagcgcacatacaccgcgcacacatgcatggagct
tcacctttctctgtcattctgcagtgaccaggagagcaagagctcccacctcccttcaaaacactgtgcccatcccgggcacta
aggcctcttaaagcacggcacctccacgagggagggccacagccacatacactccacctggcaggtggacagcgtgagcacg
tggaccatagcagggacaaggtgccccggccagccccaacgccctctgccgctgacagggacagaagccctctccagctgcgt
gtgctgcagaggccatgcgtagcctccagctgcattctattccactccagtgcctgggccagttagcaccagtgtggaagaca
gtgagctggctccggacaacagggatggaggaaaggtcccacattcacattcctgatacgtggacaaggtgaggggccgcaat
cgctctggcagcattttaaagatggggaagtagcagacacccacgcgtgaaggcaggagagcccccaactgtggtggaaatggc
cccagaatggtaggggccaagcctagctccagacacccccagagccctggagaagccaagactgagggagaaagcctgagggagg
agcgcccagtccccagggaccggcctggtgcagagctgcagctgatgttccccctctgtgcagccccaccctctgcctcgctg
agctccctgctgcgagggcctcgggtgcaagggggaggcaggtctctatctcatggagctgtcagatgagacatcgcgatcgg
agtcctcagcctcgcttggcggcggcggcgggtcgctaagcgggaccgcagtgaaagcaggagactttctagaaaaaaacacc
agttgtcaaccttggggcaggcaggaatcctgaagacggacggcactcctcctcctgctgcctcaccctctggcagcccgtga
gaagtaccggaagcgagggcggggccgcgggatggcgagggagcggcagggactgaactctctccaaacccaccctgacaggg
aaatgggccccgcctgtgtcttgggaactcagaggctgaggtcaggcatgatggctcacgcctgtaattccagcactttggga
ggcagaggcgggtggatcacgacgtcaggagttcaaggcaagcctggccaacatggtgaaaccccatctctactaaaaatgca
aaaattagccaggtgtggtggcggcgccttggaggctgaggcaagataatcacttgaacctgggaggcggaggttgtagtga
gccaaaaaaaaaaaaaagaaatagctgaagtcacagtaggagagaagctgctgagcctccagcaccctgactctagggcct
tggctttatgtctatctgcagtattttgtgattttaaaaattcactttcttgttgcggtgtaacttacacagggtcaaatg
cacaaatcatggccctgactttagataaaaatctgccccacaacccttctgttccttgccagttttaaactgcctctaacc
aggggaaccaccagagctggtggccttgggaggtttcagccctcccgtcatgaatggacatagctcatccaactgccaaggga
gagagctgtgggtctgggccagccccaccaggtaactcccaaaggcagccccacagcaagatgtgaccccagtcatgcctga
gggtctctgggctgtgttccaacctttctccccgctgtgtcccctggaaggccccatgcccaggggaggcgcctaccggtc
tccagactgggtgatgagccggcggcaggtctccatctgcacgtccaggccgcgcttcatgctgcacatctccatgtactcgt
gcaggtgccggttcatgtcgttcttggccgtggccaactccagctgtggtggggcaggcagggccatcggggttaacaggtgg
```

Figure 24 continued (SEQ ID NO: 8 continued)

cgttcacagcgcctctgttgccccgccaggaggccaacacgccaagagcagtggctgggccgggggcccaggcagccattac
tgaaggctcagattttaaaataaaccagaccaaggcagaaggcagcgaatacaccattgtttcctctgcttttcctggaaatc
tttgcctatggaggaatgcaaaggtactgctgcaggctgtgttcttttaagactgataagagtggtgaggaaagtcagtgtgg
gcgggatggagcagatccacaggctcccagggccacacaggttcctatggggcccggctcaccccctcatccctgtactgcgc
tggtcctgggctgtcccctcactgcactgtgagctcccgtaagggttagcgacaggttttcctcatcctggcagacccagacc
tcgaagggaattaactctctctgtgacccgtggcatacaagcctggctaactgctgaaaggggcccaatcctcttaccattct
ctccttatcactttatttctcacctaaaagccattttcagacactaaaaggaagactcccatattggaggtgccattgattc
tgagacctgtcctgatttcagaaatgtcacacgtggaaaacacggggctcagaatcaaagaaatccggtctccctccccgggc
ccattctgcagcccacactctgaggcaggcggagaggcagggcccaggcagcacaaactcagtgccagggacagtcgaTTAAT
TAAGCGATCGCAGGCCGCCCGCGGTGgagctccaattcgccctatagtgagtcgtattacgcgcgctcactggccgtcgtttt
acaacgtcgtgactgggaaaaccctggcgttacccaacttaatcgccttgcagcacatccccctttcgccagctggcgtaata
gcgaagaggcccgcaccgatcgcccttcccaacagttgcgcagcctgaatggcgaatggaaattgtaagcgttaatattttgt
taaaattcgcgttaaattttgttaaatcagctcattttttaaccaataggccgaaatcggcaaaatcccttataaatcaaaa
gaatagaccgagatagggttgagtgttgttccagtttggaacaagagtccactattaaagaacgtggactccaacgtcaaagg
gcgaaaaaccgtctatcagggcgatggcccactacgtgaaccatcaccctaatcaagttttttggggtcgaggtgccgtaaag
cactaaatcggaaccctaaaggagcccccgatttagagcttgacggggaaagccggcgaacgtggcgagaaaggaagggaag
aaagcgaaaggagcgggcgctagggcgctggcaagtgtagcggtcacgctgcgcgtaaccaccacacccgccgcgcttaatgc
gccgctacagggcgcgtcag Figure 24 continued (SEQ ID NO: 8 continued)

gggaaggtgaaggtcggagtcaacgggtgagttcgcgggtggctgggggggccctgggctgcgaccgcccccgaaccgcgtcta
cgagccttgcgggctccgggtctttgcagtcgtatgggggcagggtagctgttccccgcaaggagagctcaaggtcagcgctc
ggacctggcggagccccgcacccaggctgtggcgccctgtgcagctccgcccttgcggcgccatctgcccggagcctccttcc
cctagtccccagaaacaggaggtccctactcccgcccgagatcccgacccggaccccctaggtgggggacgtttctttcctttt
cgcgctctgcggggtcacgtgtcgcagaggagcccctcccccacggcctccggcaccgcaggccccgggatgctagtgcgcag
cgggtgcatccctgtccggatgctgcgcctgcggtagagcggccgccatgttgcaaccgggaaggaaatgaatgggcagccgt
taggaaagcctgccggtgactaaccctgcgctcctgcctcgatgggtggagtcgcgtgtggcggggaagtcaggtggagcgag
gctagctggcccgatttctcctccgggtgatgcttttcctagattattctctggtaaatcaaagaagtgggtttatggaggtc
ctcttgtgtccctccccgcagaggtgtggtggctgtggcatggtgccaagccgggagaagctgagtcatgggtagttggaaa
aggacatttccaccgcaaaatggcccctctggtggtggcccttcctgcagcgccggctcacctcacggccccgcccttcccc
tgccagcctagcgttgacccgaccccaaaggccaggctgtaaatgtcaccgggaggattgggtgtctgggcgcctcggggaac
ctgcccttctcccattccgtcttccggaaaccagatctcccaccgcaccctggtctgaggttaaatatagctgctgacctttt
ctgtagctggggcctgggctggggctctctcccatcccttctccccacacacatgcacttacctgtgctcccactcctgatt
tctggaaaagagctaggaaggacaggcaacttggcaaatcaaagccctggactaggggttaaaatacagcttcccctcttc
ccaccgcccagtctctgtcccttttgtaggagggacttagagaagggtgggcttgccctgtccagttaatttctgaccttt
tactcctgcccttgagtttgatgatgctgagtgtacaagcgttttctccctaaagggtgcagctgagctaggcagcagcaag
cattcctggggtggcatagtggggtggtgaataccatgtacaaagcttgtgcccagactgtgggtggcagtgccccacatggc
cgcttctcctggaagggcttcgtatgactgggggtgttgggcagccctggagccttcagttgcagccatgccttaagccaggc
cagcctggcagggaagctcaagggagataaaattcaacctcttgggccctcctgggggtaaggagatgctgcattcgccctct
taatgggggaggtggcctagggctgctcacatattctggaggagcctcccctcctcatgccttcttgcctcttgtctcttagat
ttggtcgtattgggcgcctggtcaccagggctgcttttaactctggtaaagtggatattgttgccatcaatgacccccttcatt
gacctcaactacatggtgagtgctacatggtgagccccaaagctggtgtgggaggagccacctggctgatgggcagccccttc
atacccctcacgtattccccaggtttacatgttccaatatgattccacccatggcaaattccatggcaccgtcaaggctgaga
acgggaagcttgtcatcaatggaaatcccatcaccatcttccaggagtgagtggaagacagaatggaagaaatgtgctttggg
gaggcaactaggatggtgtggctcccttgggtatatggtaaccttgtgtccctcaatatggtcctgtcccatctcccccca
ccccataggcgagatccctccaaaatcaagtggggcgatgctggcgctgagtacgtcgtggagtccactggcgtcttcacca
ccatggagaaggctgggtgagtgcaggagggcccgcggagggggaagctgactcagccctgcaaaggcaggacccgggttca
taactgtctgcttctctgctgtaggctcatttgcagggggagccaaaagggtcatcatctctgcccctctgctgatgcccc
catgttcgtcatggtgtgaaccatgagaagtatgacaacagcctcaagatcatcaggtgaggaaggcagggcccgtggagaa
gcggccagcctggcaccctatggacacgctcccctgacttgcgcccgctccctctttctttgcagcaatgcctcctgcacca
ccaactgcttagcaccccctggccaaggtcatccatgacaactttggtatcgtggaaggactcatggtatgagagctggggaat
gggactgaggctcccacctttctcatccaagactggctcctccctgccggggctgcgtgcaaccctgggttgggggttctgg
ggactggcttcccataatttccttcaaggtggggagggaggtagaggggtgatgtggggagtacgctgcagggcctcactc
cttttgcagaccacagtccatgccatcactgccacccagaagactgtggatggcccctccgggaaactgtggcgtgatggccg
cggggctctccagaacatcatccctgcctctactggcgctgccaaggctgtgggcaaggtcatccctgagctgaacgggaagc
tcactggcatggccttccgtgtccccactgccaacgtgtcagtggtggacctgacctgccgtctagaaaaacctgccaaatat
gatgacatcaagaaggtggtgaagcaggcgtcggagggcccctcaagggcatcctgggctacactgagcaccaggtggtctc
ctctgacttcaacagcgacacccactcctccaccttttgacgctggggctggcattgccctcaacgaccactttgtcaagctca
tttcctggtatgtggctggggccaggagactggctcttaaaaagtgcaggtctggcgccctctggtggctggctcagaaaaag
ggccctgacaactctttttcatcttctaggtatgacaacgaatttggctacagcaacagggtggtggacctcatggcccacatg
gcctccaaggagggaaTGGcgcgtggccggcgggTCCGGAGGAGAGGGCAGAGGAAGTCTTCTAACATGCGGTGACGTGGAGGA
GAATCCTGGCCCAAT Figure 25 (SEQ ID NO: 9)

SEQUENCE LISTING

<160> NUMBER OF SEQ ID NOS: 9

<210> SEQ ID NO 1
<211> LENGTH: 77
<212> TYPE: DNA
<213> ORGANISM: Artificial Sequence
<220> FEATURE:
<223> OTHER INFORMATION: translation interruption-reinitiation signal

<400> SEQUENCE: 1

| | |
|---|---|
| cgtggcggcg ggtccggagg agagggcaga ggaagtcttc taacatgcgg tgacgtggag | 60 |
| gagaatcctg gcccaat | 77 |

<210> SEQ ID NO 2
<211> LENGTH: 3338
<212> TYPE: DNA
<213> ORGANISM: Artificial Sequence
<220> FEATURE:
<223> OTHER INFORMATION: 5' nucleic acid that is homologous to a genomic
      sequence of 5' of a genomic stop codon of a constitutively
      expressed gene

<400> SEQUENCE: 2

| | |
|---|---|
| gggaaggtga aggtcggagt caacgggtga gttcgcgggt ggctgggggg ccctgggctg | 60 |
| cgaccgcccc cgaaccgcgt ctacgagcct tgcgggctcc gggtctttgc agtcgtatgg | 120 |
| gggcagggta gctgttcccc gcaaggagag ctcaaggtca gcgctcggac ctggcggagc | 180 |
| cccgcaccca ggctgtggcg ccctgtgcag ctccgccctt gcggcgccat ctgcccggag | 240 |
| cctccttccc ctagtcccca gaaacaggag gtccctactc ccgcccgaga tcccgacccg | 300 |
| gaccccctagg tgggggacgc tttctttcct ttcgcgctct gcggggtcac gtgtcgcaga | 360 |
| ggagcccctc ccccacggcc tccggcaccg caggccccgg gatgctagtg cgcagcgggt | 420 |
| gcatccctgt ccggatgctg cgcctgcggt agagcggccg ccatgttgca accgggaagg | 480 |
| aaatgaatgg gcagccgtta ggaaagcctg ccggtgacta accctgcgct cctgcctcga | 540 |
| tgggtggagt cgcgtgtggc ggggaagtca ggtggagcga ggctagctgg cccgatttct | 600 |
| cctccgggtg atgcttttcc tagattattc tctggtaaat caaagaagtg ggtttatgga | 660 |
| ggtcctcttg tgtcccctcc ccgcagaggt gtggtggctg tggcatggtg ccaagccggg | 720 |
| agaagctgag tcatgggtag ttggaaaagg acatttccac cgcaaaatgg cccctctggt | 780 |
| ggtggcccct tcctgcagcg ccggctcacc tcacggcccc gcccttcccc tgccagccta | 840 |
| gcgttgaccc gaccccaaag gccaggctgt aaatgtcacc gggaggattg ggtgtctggg | 900 |
| cgcctcgggg aacctgccct tctccccatt ccgtcttccg gaaaccagat ctcccaccgc | 960 |
| accctggtct gaggttaaat atagctgctg acctttctgt agctggggc ctgggctggg | 1020 |
| gctctctccc atcccttctc cccacacaca tgcacttacc tgtgctccca ctcctgattt | 1080 |
| ctggaaaaga gctaggaagg acaggcaact tggcaaatca aagccctggg actaggggt | 1140 |
| taaaatacag cttcccctct tcccaccccgc cccagtctct gtccctttg taggagggac | 1200 |
| ttagagaagg ggtgggcttg ccctgtccag ttaatttctg acctttactc ctgccctttg | 1260 |
| agtttgatga tgctgagtgt acaagcgttt tctccctaaa gggtgcagct gagctaggca | 1320 |
| gcagcaagca ttcctgggt ggcatagtgg ggtggtgaat accatgtaca agcttgtgc | 1380 |
| ccagactgtg ggtggcagtg ccccacatgg ccgcttctcc tggaagggct tcgtatgact | 1440 |
| gggggtgttg ggcagccctg gagccttcag ttgcagccat gccttaagcc aggccagcct | 1500 |
| ggcagggaag ctcaagggag ataaaattca acctcttggg ccctcctggg ggtaaggaga | 1560 |

```
tgctgcattc gccctcttaa tgggaggtg gcctagggct gctcacatat tctggaggag   1620
cctcccctcc tcatgccttc ttgcctcttg tctcttagat ttggtcgtat tgggcgcctg   1680
gtcaccaggg ctgcttttaa ctctggtaaa gtggatattg ttgccatcaa tgacccctc   1740 attgacctca actacatggt gagtgctaca tggtgagccc caaagctggt gtgggaggag   1800
ccacctggct gatgggcagc cccttcatac cctcacgtat tcccccaggt ttacatgttc   1860
caatatgatt ccacccatgg caaattccat ggcaccgtca aggctgagaa cgggaagctt   1920
gtcatcaatg gaaatcccat caccatcttc caggagtgag tggaagacag aatggaagaa   1980
atgtgctttg gggaggcaac taggatggtg tggctcccct gggtatatgg taaccttgtg   2040
tccctcaata tggtcctgtc cccatctccc ccccaccccc ataggcgaga tccctccaaa   2100
atcaagtggg gcgatgctgg cgctgagtac gtcgtggagt ccactggcgt cttcaccacc   2160
atggagaagg ctggggtgag tgcaggaggg cccgcgggag gggaagctga ctcagccctg   2220
caaaggcagg acccgggttc ataactgtct gcttctctgc tgtaggctca tttgcagggg   2280
ggagccaaaa gggtcatcat ctctgccccc tctgctgatg cccccatgtt cgtcatgggt   2340
gtgaaccatg agaagtatga caacagcctc aagatcatca ggtgaggaag cagggcccg   2400 tggagaagcg gccagcctgg caccctatgg acacgctccc ctgacttgcg ccccgctccc   2460
tctttctttg cagcaatgcc tcctgcacca ccaactgctt agcacccctg gccaaggtca   2520
tccatgacaa ctttggtatc gtggaaggac tcatggtatg agagctgggg aatgggactg   2580
aggctcccac ctttctcatc caagactggc tcctccctgc cggggctgcg tgcaaccctg   2640
gggttggggg ttctggggac tggctttccc ataatttcct ttcaaggtgg ggagggaggt   2700 agagggtga tgtggggagt acgctgcagg gcctcactcc ttttgcagac cacagtccat   2760
gccatcactg ccacccagaa gactgtggat ggccctccg ggaaactgtg gcgtgatggc   2820
cgcggggctc tccagaacat catccctgcc tctactggcg ctgccaaggc tgtgggcaag   2880
gtcatccctg agctgaacgg gaagctcact ggcatggcct tccgtgtccc cactgccaac   2940
gtgtcagtgg tggacctgac ctgccgtcta gaaaaacctg ccaaatatga tgacatcaag   3000
aaggtggtga agcaggcgtc ggagggcccc ctcaagggca tcctgggcta cactgagcac   3060
caggtggtct cctctgactt caacagcgac acccactcct ccacctttga cgctggggct   3120
ggcattgccc tcaacgacca cttttgtcaag ctcatttcct ggtatgtggc tggggccaga   3180
gactggctct taaaaagtgc agggtctggc gccctctggt ggctggctca gaaaaagggc   3240
cctgacaact cttttcatct tctaggtatg acaacgaatt tggctacagc aacagggtgg   3300
tggacctcat ggcccacatg gcctccaagg agggaatg                           3338
```

<210> SEQ ID NO 3
<211> LENGTH: 4236
<212> TYPE: DNA
<213> ORGANISM: Artificial Sequence
<220> FEATURE:
<223> OTHER INFORMATION: 3' nucleic acid that is homologous to a genomic
    sequence of 3' of a genomic stop codon of a constitutively
    expressed gene

<400> SEQUENCE: 3

```
aagaggaaga gagagaccct cactgctggg gagtccctgc cacactcagt cccccaccac     60
actgaatctc ccctcctcac agttgccatg tagacccctt gaagagggga ggggcctagg   120
gagccgcacc ttgtcatgta ccatcaataa agtaccctgt gctcaaccag ttacttgtcc   180
tgtcttattc tagggtctgg ggcagagggg agggaagctg ggcttgtgtc aaggtgagac   240
```

-continued

```
attcttgctg gggagggacc tggtatgttc tcctcagact gagggtaggg cctccaaaca      300
gccttgcttg cttcgagaac catttgcttc ccgctcagac gtcttgagtg ctacaggaag      360
ctggcaccac tacttcagag aacaaggcct tttcctctcc tcgctccagt cctaggctat      420
ctgctgttgg ccaaacatgg aagaagctat tctgtgggca gccccaggga ggctgacagg      480
tggaggaagt cagggctcgc actgggctct gacgctgact ggttagtgga gctcagcctg      540
gagctgagct gcagcgggca attccagctt ggcctccgca gctgtgaggt cttgagcacg      600
tgctctattg ctttctgtgc cctcgtgtct tatctgagga catcgtggcc agcccctaag      660
gtcttcaagc aggattcatc taggtaaacc aagtacctaa aaccatgccc aaggcggtaa      720
ggactatata atgtttaaaa atcggtaaaa atgcccacct cgcatagttt tgaggaagat      780
gaactgagat gtgtcagggt gacttatttc catcatcgtc cttaggggaa cttgggtagg      840
ggcaaggcgt gtagctggga cctaggtcca gaccccctggc tctgccactg aacggctcag      900
ttgctttggg cagttactcc cgggcctcac tttgcacgtg tgcttaccta gtggagacaa      960
aagtacatac ctcggtagag cgcgcacgcc tgtaaccccca gcactttggg aggccaaggt     1020
gggtgtatca cctgaggtca ggagtttgag accagcctgg ccaacatggt gaaactccgt     1080
ctctactaaa attacaaaaa tcagccaggc ttcatggcac atgcctatag tcccagctac     1140
aggcatgctg aagcaggaga atcgcttgca ccccggaggc agaggctgca gtgagctgag     1200
accacaccac tgcactccag cctaggcaac agagtatgag actccatctc aaaaaaaaaa     1260
aaagtaccta cctcagagtt caaactagtg aatattagga agtgcttgag acagtgacac     1320
caaagtgcac aataaatact cgccagtttc attattatta aagaatccat ttgaatgtca     1380
gctcaacaca gcctcctata ccgaggcatt gtgaaccgca tctccccagc ttctccaggc     1440
ttttccaaga atcagggaca ctgtagcctg ttggtctcag tgtatgacag acacggagga     1500
agcacatctt tagctgatac ttaaacagag accctgagcg cacatacacc cgcgcacaca     1560
tgcatggagc ttcaccttct ctgtcattct gcagtgacca ggagagcaag agctcccacc     1620
tcccttcaaa acactgtgcc catcccgggc actaaggcct cttttaaagca cggcacctcc     1680 acgagggagg gccacagcca catacactcc acctggcagg tggacagcgt gagcacgtgg     1740
accatagcag ggacaaggtg ccccggccag ccccaacgcc ctctgccgct gacagggaca     1800
gaagccctct ccagctgcgt gtgctgcaga ggccatgcgt agcctccagc tgcattctat     1860
tccactccag tgcctgggcc agttagcacc agtgtggaag acagtgagct ggctccggac     1920
aacagggatg gaggaaaggt cccacattca cattcctgat acgtggacaa ggtgagggggc     1980 cgcaatcgct ctggcagcat tttaaagatg gggaagtagc agacacccac gcgtgaaggc     2040
aggagagccc caactgtggt ggaaatggcc ccagaatggt agggcaagc ctagctccag     2100 acaccccaga gccctggaga agccaagact gagggagaaa gcctgaggga ggagcgcccc     2160
agtccccagg gaccggcctg gtgcagagct gcagctgatg ttcccctctg tgcagcccca     2220
ccctctgcct cgctgagctc cctgctgcga gggcctcggt tgcaaggggg aggcaggtct     2280
ctatctcatg gagctgtcag atgagacatc gcgatcggag tcctcagcct cgcttggcgg     2340
cggcggcggg tcgctaagcg ggaccgcagt gaaagcagga gactttctag aaaaaaacac     2400
cagttgtcaa ccttggggca ggcaggaatc ctgaagacgg acggcactcc tcctcctgct     2460
gcctcaccct ctggcagccc gtgagaagta ccggaagcga gggcgggggcc gcgggatggc     2520 gagggagcgc cagggactga actctctcca aacccacccct gacagggaaa tgggccccgc     2580
ctgtgtcttg ggaactcaga ggctgaggtc aggcatgatg gctcacgcct gtaattccag     2640
```

-continued

| | |
|---|---|
| cactttggga ggcagaggcg ggtggatcac gacgtcagga gttcaaggca agcctggcca | 2700 |
| acatggtgaa accccatctc tactaaaaat gcaaaaatta gccaggtgtg gtggcgggcg | 2760 |
| ccttggaggc tgaggcaaga taatcacttg aacctgggag gcggaggttg tagtgagcca | 2820 |
| aaaaaaaaaa aaaagaaat agctgaagtc acagtaggag agaagctgct gagcctccag | 2880 |
| caccctgact ctagggcctt ggctttatgt ctatctgcag tattttgtg attttaaaa | 2940 |
| attcactttc ttgttgcggt gtaacttaca cagggtcaaa tgcacaaatc atggccctga | 3000 |
| ctttagataa aaatctgccc ccacaaccct tctgttcctt gccagttttt aaactgcctc | 3060 |
| taaccagggg aaccaccaga gctggtggcc ttgggaggtt tcagccctcc cgtcatgaat | 3120 |
| ggacatagct catccaactg ccaagggaga gagctgtggg tctgggccag ccccaccagg | 3180 |
| taactcccaa agggcagccc cacagcaaga tgtgacccag tcattgcctg agggtctctg | 3240 |
| gggctgtgtt ccaacctttc tccccgctgt gtccccctgg aaggccccat gcccagggga | 3300 |
| ggcgcctacc ggtctccaga ctgggtgatg agccggcggc aggtctccat ctgcacgtcc | 3360 |
| aggccgcgct tcatgctgca catctccatg tactcgtgca ggtgccggtt catgtcgttc | 3420 |
| ttggccgtgg ccaactccag ctgtggtggg gcaggcaggg ccatcggggt taacaggtgg | 3480 |
| cgttcacagc gcctctgttg cccccgccag gaggccaaca cgccaagagc agtggctggg | 3540 |
| ccggggcccc aggcagccat tactgaaggc tcagatttta aaataaacca gaccaaggca | 3600 |
| gaaggcagcg aatacaccat tgtttcctct gcttttcctg gaaatctttg cctatggagg | 3660 |
| aatgcaaagg tactgctgca ggctgtgttc ttttaagact gataagagtg gtgaggaaag | 3720 |
| tcagtgtggg cgggatggag cagatccaca ggctcccagg gccacacagg ttcctatggg | 3780 |
| gcccggctca cccctcatcc cctgtactgc gctggtcctg ggctgtcccc tcactgcact | 3840 |
| gtgagctccc gtaagggtta gcgacaggtt ttcctcatcc tggcagaccc agacctcgaa | 3900 |
| gggaattaac tctctctgtg accgtggca tacaagcctg gctaactgct gaaaggggcc | 3960 |
| caatcctctt accattctct ccttatcact ttattttctc acctaaaagc cattttcaga | 4020 |
| cactaaaagg aagactccca tattggaggt gccattgatt ctgagacctg tcctgatttc | 4080 |
| agaaatgtca cacgtggaaa cacggggct cagaatcaaa gaatccggt ctccctcccc | 4140 |
| gggcccattc tgcagcccac actctgaggc aggcggagag gcagggccca ggcagcacaa | 4200 |
| actcagtgcc agggacagtc gattaattaa gcgatc | 4236 |

<210> SEQ ID NO 4
<211> LENGTH: 576
<212> TYPE: DNA
<213> ORGANISM: Artificial Sequence
<220> FEATURE:
<223> OTHER INFORMATION: internal ribosomal entry site

<400> SEQUENCE: 4

| | |
|---|---|
| cccccctaa cgttactggc cgaagccgct tggaataagg ccggtgtgcg tttgtctata | 60 |
| tgttattttc caccatattg ccgtcttttg gcaatgtgag ggcccggaaa cctggccctg | 120 |
| tcttcttgac gagcattcct aggggtcttt cccctctcgc caaaggaatg caaggtctgt | 180 |
| tgaatgtcgt gaaggaagca gttcctctgg aagcttcttg aagacaaaca acgtctgtag | 240 |
| cgacccttg caggcagcgg aaccccccac ctggcgacag gtgcctctgc ggccaaaagc | 300 |
| cacgtgtata agatacacct gcaaaggcgg cacaacccca gtgccacgtt gtgagttgga | 360 |
| tagttgtgga aagagtcaaa tggctctcct caagcgtatt caacaagggg ctgaaggatg | 420 |
| cccagaaggt accccattgt atgggatctg atctggggcc tcggtacaca tgctttacat | 480 |

```
gtgtttagtc gaggttaaaa aaacgtctag gccccccgaa ccacggggac gtggttttcc      540
tttgaaaaac acgatgataa tatggccaca accatg                               576

<210> SEQ ID NO 5
<211> LENGTH: 11197
<212> TYPE: DNA
<213> ORGANISM: Artificial Sequence
<220> FEATURE:
<223> OTHER INFORMATION: vector GT-GFP

<400> SEQUENCE: 5
gattcattaa tgcagctggc acgacaggtt cccgactgg aaagcgggca gtgagcgcaa       60
cgcaattaat gtgagttagc tcactcatta ggcaccccag gctttacact ttatgcttcc    120
ggctcgtatg ttgtgtggaa ttgtgagcgg ataacaattt cacacaggaa acagctatga    180
ccatgattac gccaagctcg aaattaaccc tcactaaagg gaacaaaagc tggtacgtta    240
attaaaggga aggtgaaggt cggagtcaac gggtgagttc gcggtggct gggggggccct    300 gggctgcgac cgccccgaa ccgcgtctac gagccttgcg ggctccggt cttttgcagtc    360 gtatgggggc agggtagctg ttccccgcaa ggagagctca aggtcagcgc tcggacctgg    420
cggagccccg cacccaggct gtggcgccct gtgcagctcc gcccttgcgg cgccatctgc    480
ccggagcctc cttcccctag tccccagaaa caggaggtcc ctactcccgc ccgagatccc    540
gacccggacc cctaggtggg ggacgctttc tttccttcg cgctctgcgg ggtcacgtgt    600
cgcagaggag cccctccccc acggcctccg gcaccgcagg cccgggatg ctagtgcgca    660 gcgggtgcat ccctgtccgg atgctgcgcc tgcggtagag cggccgccat gttgcaaccg    720
ggaaggaaat gaatgggcag ccgttaggaa agcctgccgg tgactaaccc tgcgctcctg    780
cctcgatggg tggagtcgcg tgtggcgggg aagtcaggtg gagcgaggct agctggcccg    840
atttctcctc cgggtgatgc ttttcctaga ttattctctg gtaaatcaaa gaagtgggtt    900 tatgaggtc ctcttgtgtc ccctccccgc agaggtgtgg tggctgtggc atggtgccaa    960
gccgggagaa gctgagtcat gggtagttgg aaaaggacat ttccaccgca aaatggcccc    1020
tctggtggtg gccccttcct gcagcgccgg ctcacctcac ggccccgccc ttcccctgcc    1080
agcctagcgt tgacccgacc ccaaaggcca ggctgtaaat gtcaccggga ggattgggtg    1140
tctgggcgcc tcggggaacc tgccccttctc cccattccgt cttccggaaa ccagatctcc    1200
caccgcaccc tggtctgagg ttaaatatag ctgctgacct ttctgtagct gggggcctgg    1260
gctggggctc tctcccatcc cttctccca cacacatgca cttacctgtg ctcccactcc    1320
tgatttctgg aaaagagcta ggaaggacag gcaacttggc aaatcaaagc cctgggacta    1380
gggggttaaa atacagcttc ccctcttccc acccgcccca gtctctgtcc cttttgtagg    1440
agggacttag agaagggtg ggcttgccct gtccagttaa tttctgacct ttactcctgc    1500
cctttgagtt tgatgatgct gagtgtacaa gcgttttctc cctaaagggt gcagctgagc    1560
taggcagcag caagcattcc tggggtggca tagtggggtg gtgaatacca tgtacaaagc    1620
ttgtgcccag actgtgggtg gcagtgcccc acatggccgc ttctcctgga agggcttcgt    1680
atgactgggg gtgttgggca gcccctggagc cttcagttgc agccatgcct taagccaggc    1740
cagcctggca gggaagctca aggagataa aattcaacct cttgggccct cctgggggta    1800
aggagatgct gcattcgccc tcttaatggg gaggtggcct agggctgctc acatattctg    1860
gaggagcctc ccctcctcat gccttcttgc ctcttgtctc ttagatttgg tcgtattggg    1920
cgcctggtca ccagggctgc ttttaactct ggtaaagtgg atattgttgc catcaatgac    1980
```

```
cccttcattg acctcaacta catggtgagt gctacatggt gagccccaaa gctggtgtgg    2040
gaggagccac ctggctgatg ggcagcccct tcataccctc acgtattccc ccaggtttac    2100
atgttccaat atgattccac ccatggcaaa ttccatggca ccgtcaaggc tgagaacggg    2160
aagcttgtca tcaatggaaa tcccatcacc atcttccagg agtgagtgga agacagaatg    2220
gaagaaatgt gctttgggga ggcaactagg atggtgtggc tcccttgggt atatggtaac    2280
cttgtgtccc tcaatatggt cctgtcccca tctccccccc accccatag gcgagatccc    2340 tccaaaatca agtggggcga tgctggcgct gagtacgtcg tggagtccac tggcgtcttc    2400
accaccatgg agaaggctgg ggtgagtgca ggagggcccg cggggagggga agctgactca    2460 gccctgcaaa ggcaggaccc gggttcataa ctgtctgctt ctctgctgta ggctcatttg    2520 cagggggggag ccaaaagggt catcatctct gccccctctg ctgatgcccc catgttcgtc    2580
atgggtgtga accatgagaa gtatgacaac agcctcaaga tcatcaggtg aggaaggcag    2640
ggcccgtgga gaagcggcca gcctggcacc ctatggacac gctcccctga cttgcgcccc    2700
gctccctctt tctttgcagc aatgcctcct gcaccaccaa ctgcttagca cccctggcca    2760
aggtcatcca tgacaacttt ggtatcgtgg aaggactcat ggtatgagag ctggggaatg    2820
ggactgaggc tcccacccttt ctcatccaag actggctcct ccctgccggg gctgcgtgca    2880
accctggggt tgggggttct ggggactggc tttcccataa tttccttttca aggtggggag    2940 ggaggtagag gggtgatgtg gggagtacgc tgcagggcct cactccttttt gcagaccaca    3000 gtccatgcca tcactgccac cagaagact gtggatggcc cctccgggaa actgtggcgt    3060 gatgccgcg gggctctcca gaacatcatc cctgcctcta ctggcgctgc caaggctgtg    3120
ggcaaggtca tccctgagct gaacgggaag ctcactggca tggccttccg tgtccccact    3180
gccaacgtgt cagtggtgga cctgacctgc cgtctagaaa aacctgccaa atatgatgac    3240
atcaagaagg tggtgaagca ggcgtcggag ggccccctca agggcatcct gggctacact    3300
gagcaccagg tggtctcctc tgacttcaac agcgacaccc actcctccac ctttgacgct    3360
ggggctggca ttgccctcaa cgaccacttt gtcaagctca tttcctggta tgtggctggg    3420
gccagagact ggctcttaaa aagtgcaggg tctggcgccc tctggtggct ggctcagaaa    3480
aagggccctg acaactcttt tcatcttcta ggtatgacaa cgaatttggc tacagcaaca    3540
gggtggtgga cctcatggcc cacatggcct ccaaggaggg aatggcgcgt ggcggcgggt    3600
ccggaggaga gggcagagga agtcttctaa catgcggtga cgtggaggag aatcctggcc    3660
caatggtgag caagggcgag gagctgttca ccggggtggt gcccatcctg gtcgagctgg    3720
acggcgacgt aaacggccac aagttcagcg tgtccggcga gggcgagggc gatgccacct    3780
acggcaagct gaccctgaag ttcatctgca ccaccggcaa gctgcccgtg ccctggccca    3840
ccctcgtgac caccctgacc tacggcgtgc agtgcttcag ccgctacccc gaccacatga    3900
agcagcacga cttcttcaag tccgccatgc ccgaaggcta cgtccaggag cgcaccatct    3960
tcttcaagga cgacggcaac tacaagaccc gcgccgaggt gaagttcgag ggcgacaccc    4020
tggtgaaccg catcgagctg aagggcatcg acttcaagga ggacggcaac atcctggggc    4080
acaagctgga gtacaactac aacagccaca acgtctatat catggccgac aagcagaaga    4140
acggcatcaa ggtgaacttc aagatccgcc acaacatcga ggacggcagc gtgcagctcg    4200
ccgaccacta ccagcagaac acccccatcg gcgacggccc cgtgctgctg ccgacaaccc    4260
actacctgag cacccagtcc gccctgagca aagaccccaa cgagaagcgc gatcacatgg    4320
tcctgctgga gttcgtgacc gccgccggga tcactctcgg catggacgag ctgtacaagt    4380
```

```
aaggatccgc ccctctccct cccccccccc taacgttact ggccgaagcc gcttggaata    4440
aggccggtgt gcgtttgtct atatgttatt ttccaccata ttgccgtctt ttggcaatgt    4500
gagggcccgg aaacctggcc ctgtcttctt gacgagcatt cctaggggtc tttcccctct    4560
cgccaaagga atgcaaggtc tgttgaatgt cgtgaaggaa gcagttcctc tggaagcttc    4620
ttgaagacaa acaacgtctg tagcgaccct ttgcaggcag cggaaccccc cacctggcga    4680
caggtgcctc tgcggccaaa agccacgtgt ataagataca cctgcaaagg cggcacaacc    4740
ccagtgccac gttgtgagtt ggatagttgt ggaaagagtc aaatggctct cctcaagcgt    4800
attcaacaag gggctgaagg atgcccagaa ggtaccccat tgtatgggat ctgatctggg    4860
gcctcggtac acatgcttta catgtgttta gtcgaggtta aaaaaacgtc taggcccccc    4920
gaaccacggg gacgtggttt tcctttgaaa aacacgatga taatatgcc acaaccatgg    4980
cgcgtgggat tgaacaagat ggattgcacg caggttctcc ggccgcttgg gtggagaggc    5040
tattcggcta tgactgggca aacagacaa tcggctgctc tgatgccgcc gtgttccggc    5100
tgtcagcgca ggggcgcccg gttcttttg tcaagaccga cctgtccggt gccctgaatg    5160
aactgcagga cgaggcagcg cggctatcgt ggctggccac gacgggcgtt ccttgcgcag    5220
ctgtgctcga cgttgtcact gaagcgggaa gggactggct gctattgggc gaagtgccgg    5280
ggcaggatct cctgtcatct caccttgctc ctgccgagaa agtatccatc atggctgatg    5340
caatgcggcg gctgcatacg cttgatccgg ctacctgccc attcgaccac caagcgaaac    5400
atcgcatcga gcgagcacgt actcggatgg aagccggtct tgtcgatcag gatgatctgg    5460
acgaagagca tcaggggctc gcgccagccg aactgttcgc caggctcaag gcgcgcatgc    5520
ccgacggcga ggatctcgtc gtgacccatg gcgatgcctg cttgccgaat atcatggtgg    5580
aaaatggccg cttttctgga ttcatcgact gtggccggct gggtgtggcg gaccgctatc    5640
aggacatagc gttggctacc cgtgatattg ctgaagagct tgcggcgaa tgggctgacc    5700
gcttcctcgt gctttacggt atcgccgctc ccgattcgca gcgcatcgcc ttctatcgcc    5760
ttcttgacga gttcttctga ggggatcgat ccgctgtaag tctgcagaaa ttgatgatct    5820
attaaacaat aaagatgtcc actaaaatgg aagtttttta ctgtcatact ttgttaagaa    5880
gggtgagaac agagtaccta cattttgaat ggaaggattg gagctacggg ggtggggtg    5940
ggggtgggat tagataaatg cctgctcttt actgaaggct cttctatt gctttatgat     6000
aatgtttcat agttggatat cataatttaa acaagcaaaa ccaaattaag ggccagctca    6060
ttcctccact catgatctat agatctatag atctctcggg ggatcattgt ttttttcttg    6120
attcccactt tgtggttcta agtactgtgg tttccaaatg tgtcagtttc atagcctgaa    6180
gaacgagatc agcagcctct gttccacata cacttcattc tcagtattgt tttgccaagt    6240
tctaattcca tcagaagctg actatcgata agcttagatc gagcacaaga ggaagagaga    6300
gaccctcact gctggggagt ccctgccaca ctcagtcccc caccacactg aatctcccct    6360
cctcacagtt gccatgtaga ccccttgaag aggggagggg cctagggagc cgcaccttgt    6420
catgtaccat caataaagta ccctgtgctc aaccagttac ttgtcctgtc ttattctagg    6480
gtctgggca gaggggaggg aagctgggct tgtgtcaagg tgagacattc ttgctgggga    6540
gggacctggt atgttctcct cagactgagg gtagggcctc caaacagcct tgcttgcttc    6600
gagaaccatt tgcttcccgc tcagacgtct tgagtgctac aggaagctgg caccactact    6660
tcagagaaca aggcctttc ctctcctcgc tccagtccta ggctatctgc tgttggccaa    6720
acatggaaga agctattctg tgggcagccc cagggaggct gacaggtgga ggaagtcagg    6780
```

```
gctcgcactg ggctctgacg ctgactggtt agtggagctc agcctggagc tgagctgcag    6840
cgggcaattc cagcttggcc tccgcagctg tgaggtcttg agcacgtgct ctattgcttt    6900
ctgtgccctc gtgtcttatc tgaggacatc gtggccagcc cctaaggtct tcaagcagga    6960
ttcatctagg taaaccaagt acctaaaacc atgcccaagg cggtaaggac tatataatgt    7020
ttaaaaatcg gtaaaaatgc ccacctcgca tagttttgag gaagatgaac tgagatgtgt    7080
cagggtgact tatttccatc atcgtcctta ggggaacttg ggtaggggca aggcgtgtag    7140
ctgggaccta ggtccagacc cctggctctg ccactgaacg gctcagttgc tttgggcagt    7200
tactcccggg cctcactttg cacgtgtgct tacctagtgg agacaaaagt acatacctcg    7260
gtagagcgcg cacgcctgta accccagcac tttgggaggc caaggtgggt gtatcacctg    7320
aggtcaggag tttgagacca gcctggccaa catggtgaaa ctccgtctct actaaaatta    7380
caaaaatcag ccaggcttca tggcacatgc ctatagtccc agctacaggc atgctgaagc    7440
aggagaatcg cttgcacccc ggaggcagag gctgcagtga gctgagacca ccactgca     7500 ctccagccta ggcaacagag tatgagactc atctcaaaa aaaaaaaag tacctacctc      7560 agagttcaaa ctagtgaata ttaggaagtg cttgagacag tgacaccaaa gtgcacaata    7620
aatactcgcc agtttcatta ttattaaaga atccatttga atgtcagctc aacacagcct    7680
cctataccga ggcattgtga accgcatctc cccagcttct ccaggctttt ccaagaatca    7740
gggacactgt agcctgttgg tctcagtgta tgacagacac ggaggaagca catctttagc    7800
tgatacttaa acagagaccc tgagcgcaca tacacccgcg cacacatgca tggagcttca    7860
ccttctctgt cattctgcag tgaccaggag agcaagagct cccacctccc ttcaaaacac    7920
tgtgcccatc ccgggcacta aggcctcttt aaagcacggc acctccacga gggagggcca    7980
cagccacata cactccacct ggcaggtgga cagcgtgagc acgtggacca tagcagggac    8040
aaggtgcccc ggccagcccc aacgccctct gccgctgaca gggacagaag ccctctccag    8100
ctgcgtgtgc tgcagaggcc atgcgtagcc tccagctgca ttctattcca ctccagtgcc    8160
tgggccagtt agcaccagtg tggaagacag tgagctggct ccggacaaca gggatggagg    8220
aaaggtccca cattcacatt cctgatacgt ggacaaggtg aggggccgca atcgctctgg    8280
cagcatttta aagatgggga agtagcgac ccacgcgt gaaggcagga gagccccaac       8340
tgtggtggaa atggccccag aatggtaggg ccaagcctag ctccagacac cccagagccc    8400
tggagaagcc aagactgagg gagaaagcct gagggaggag cgcccagtc cccagggacc     8460 ggcctggtgc agagctgcag ctgatgttcc cctctgtgca gccccaccct ctgcctcgct    8520
gagctccctg ctgcgagggc ctcgggtgca agggggaggc aggtctctat ctcatggagc    8580
tgtcagatga gacatcgcga tcggagtcct cagcctcgct tggcggcggc ggcgggtcgc    8640
taagcgggac cgcagtgaaa gcaggagact ttctagaaaa aaacaccagt tgtcaacctt    8700
ggggcaggca ggaatcctga agacggacgg cactcctcct cctgctgcct caccctctgg    8760
cagcccgtga gaagtaccgg aagcgagggc ggggccgcgg gatggcgagg gagcggcagg    8820
gactgaactc tctccaaacc caccctgaca gggaaatggg ccccgcctgt gtcttgggaa    8880
ctcagaggct gaggtcaggc atgatggctc acgcctgtaa ttccagcact ttgggaggca    8940
gaggcgggtg gatcacgacg tcaggagttc aaggcaagcc tggccaacat ggtgaaaccc    9000
catctctact aaaaatgcaa aaattagcca ggtgtggtgg cgggcgcctt ggaggctgag    9060
```

```
gcaagataat cacttgaacc tgggaggcgg aggttgtagt gagccaaaaa aaaaaaaaaa   9120
agaaatagct gaagtcacag taggagagaa gctgctgagc ctccagcacc ctgactctag   9180
ggccttggct ttatgtctat ctgcagtatt tttgtgattt ttaaaaattc actttcttgt   9240
tgcggtgtaa cttacacagg gtcaaatgca caaatcatgg ccctgacttt agataaaaat   9300
ctgcccccac aaccccttctg ttccttgcca gttttaaac tgcctctaac caggggaacc   9360
accagagctg gtggccttgg gaggtttcag ccctcccgtc atgaatggac atagctcatc   9420
caactgccaa gggagagagc tgtgggtctg gccagcccc accaggtaac tcccaaggg    9480 cagccccaca gcaagatgtg acccagtcat tgcctgaggg tctctggggc tgtgttccaa   9540
cctttctccc cgctgtgtcc ccctggaagg ccccatgccc aggggaggcg cctaccggtc   9600
tccagactgg gtgatgagcc ggcggcaggt ctccatctgc acgtccaggc cgcgcttcat   9660
gctgcacatc tccatgtact cgtgcaggtg ccggttcatg tcgttcttgg ccgtggccaa   9720
ctccagctgt ggtggggcag gcagggccat cggggttaac aggtggcgtt cacagcgcct   9780
ctgttgcccc cgccaggagg ccaacacgcc aagagcagtg gctgggccgg gggcccaggc   9840
agccattact gaaggctcag attttaaaat aaaccagacc aaggcagaag gcagcgaata   9900
caccattgtt cctctgctt ttcctggaaa tctttgccta tggaggaatg caaaggtact    9960
gctgcaggct gtgttctttt aagactgata agagtggtga ggaaagtcag tgtgggcggg  10020
atggagcaga tccacaggct cccagggcca cacaggttcc tatggggccc ggctcacccc  10080
tcatcccctg tactgcgctg gtcctgggct gtccctcac tgcactgtga gctcccgtaa   10140
gggttagcga caggttttcc tcatcctggc agacccagac ctcgaaggga attaactctc  10200
tctgtgaccc gtggcataca agcctggcta actgctgaaa ggggcccaat cctcttacca  10260
ttctctcctt atcactttat tttctcacct aaaagccatt ttcagacact aaaaggaaga  10320
ctcccatatt ggaggtgcca ttgattctga gacctgtcct gatttcagaa atgtcacacg  10380
tggaaaacac ggggctcaga atcaaagaaa tccgtctcc ctccccgggc ccattctgca   10440
gcccacactc tgaggcaggc ggagaggcag ggcccaggca gcacaaactc agtgccaggg  10500
acagtcgatt aattaagcga tcgcaggccg ccgcgtgg agctccaatt cgccctatag    10560
tgagtcgtat tacgcgcgct cactggccgt cgttttacaa cgtcgtgact gggaaaaccc  10620
tggcgttacc caacttaatc gccttgcagc acatcccct ttcgccagct ggcgtaatag    10680
cgaagaggcc cgcaccgatc gcccttccca acagttgcgc agcctgaatg gcgaatggaa  10740
attgtaagcg ttaatatttt gttaaaattc gcgttaaatt tttgttaaat cagctcattt  10800
tttaaccaat aggccgaaat cggcaaaatc ccttataaat caaaagaata gaccgagata  10860
gggttgagtg ttgttccagt ttggaacaag agtccactat taaagaacgt ggactccaac  10920 gtcaaaggc gaaaaccgt ctatcagggc gatggcccac tacgtgaacc atcaccctaa    10980
tcaagttttt tggggtcgag gtgccgtaaa gcactaaatc ggaaccctaa agggagcccc  11040
cgatttagag cttgacgggg aaagccggcg aacgtggcga gaaaggaagg gaagaaagcg  11100
aaaggagcgg gcgctagggc gctggcaagt gtagcggtca cgctgcgcgt aaccaccaca  11160
cccgccgcgc ttaatgcgcc gctacagggc gcgtcag                           11197
```

<210> SEQ ID NO 6
<211> LENGTH: 10802
<212> TYPE: DNA
<213> ORGANISM: Artificial Sequence
<220> FEATURE:
<223> OTHER INFORMATION: vector GT-mCherry

<400> SEQUENCE: 6

```
gattcattaa tgcagctggc acgacaggtt tcccgactgg aaagcgggca gtgagcgcaa       60
cgcaattaat gtgagttagc tcactcatta ggcaccccag gctttacact ttatgcttcc      120
ggctcgtatg ttgtgtggaa ttgtgagcgg ataacaattt cacacaggaa acagctatga      180
ccatgattac gccaagctcg aaattaaccc tcactaaagg gaacaaaagc tggtacgtta      240
attaaaggga aggtgaaggt cggagtcaac gggtgagttc gcgggtggct gggggggccct     300
gggctgcgac cgcccccgaa ccgcgtctac gagccttgcg ggctccgggt ctttgcagtc      360
gtatggggggc agggtagctg ttccccgcaa ggagagctca aggtcagcgc tcggacctgg     420
cggagccccg cacccaggct gtggcgccct gtgcagctcc gcccttgcgg cgccatctgc      480
ccggagcctc cttcccctag tccccagaaa caggaggtcc ctactcccgc ccagatccc      540
gacccggacc cctaggtggg ggacgctttc tttccttcg cgctctgcgg ggtcacgtgt       600
cgcagaggag cccctccccc acggcctccg gcaccgcagg ccccgggatg ctagtgcgca      660
gcgggtgcat ccctgtccgg atgctgcgcc tgcggtagag cggccgccat gttgcaaccg      720
ggaaggaaat gaatgggcag ccgttaggaa agcctgccgg tgactaaccc tgcgctcctg      780
cctcgatggg tggagtcgcg tgtggcgggg aagtcaggtg gagcgaggct agctggcccg      840
atttctcctc cgggtgatgc ttttcctaga ttattctctg gtaaatcaaa gaagtgggtt      900
tatggaggtc ctcttgtgtc ccctccccgc agaggtgtgg tggctgtggc atggtgccaa      960
gccgggagaa gctgagtcat gggtagttgg aaaaggacat ttccaccgca aaatggcccc    1020
tctggtggtg gccccttcct gcagcgccgg ctcacctcac ggccccgccc ttcccctgcc    1080
agcctagcgt tgacccgacc ccaaaggcca ggctgtaaat gtcaccggga ggattgggtg    1140
tctgggcgcc tcggggaacc tgcccttctc cccattccgt cttccggaaa ccagatctcc    1200
caccgcaccc tggtctgagg ttaaatatag ctgctgacct ttctgtagct gggggcctgg    1260
gctgggctc tctcccatcc cttctcccca cacacatgca cttacctgtg ctcccactcc    1320
tgatttctgg aaaagagcta ggaaggacag gcaacttggc aaatcaaagc cctgggacta    1380
ggggggttaaa atacagcttc ccctcttccc acccgcccca gtctctgtcc cttttgtagg    1440
agggacttag agaaggggtg ggcttgccct gtccagttaa tttctgacct ttactcctgc    1500
cctttgagtt tgatgatgct gagtgtacaa gcgttttctc cctaaagggt gcagctgagc    1560
taggcagcag caagcattcc tggggtggca tagtggggtg gtgaatacca tgtacaaagc    1620
ttgtgcccag actgtgggtg gcagtgcccc acatggccgc ttctcctgga agggcttcgt    1680
atgactgggg gtgttgggca gccctggagc cttcagttgc agccatgcct taagccaggc    1740
cagcctggca gggaagctca agggagataa aattcaacct cttgggccct cctgggggta    1800
aggagatgct gcattcgccc tcttaatggg gaggtggcct agggctgctc acatattctg    1860
gaggagcctc ccctcctcat gccttcttgc ctcttgtctc ttagatttgg tcgtattggg    1920
cgcctggtca ccagggctgc ttttaactct ggtaaagtgg atattgttgc catcaatgac    1980
cccttcattg acctcaacta catggtgagt gctacatggt gagccccaaa gctggtgtgg    2040
gaggagccac ctggctgatg ggcagcccct tcataccctc acgtattccc ccaggtttac    2100
atgttccaat atgattccac ccatggcaaa ttccatggca ccgtcaaggc tgagaacggg    2160
aagcttgtca tcaatggaaa tcccatcacc atcttccagg agtgagtgga agacagaatg    2220
gaagaaatgt gctttgggga ggcaactagg atggtgtggc tcccttgggt atatggtaac    2280
cttgtgtccc tcaatatggt cctgtcccca tctccccccc accccatag gcgagatccc    2340
```

```
tccaaaatca agtggggcga tgctggcgct gagtacgtcg tggagtccac tggcgtcttc    2400
accaccatgg agaaggctgg ggtgagtgca ggagggcccg cgggagggga agctgactca    2460
gccctgcaaa ggcaggaccc gggttcataa ctgtctgctt ctctgctgta ggctcatttg    2520
caggggggag ccaaaagggt catcatctct gcccctctg ctgatgcccc catgttcgtc     2580
atgggtgtga accatgagaa gtatgacaac agcctcaaga tcatcaggtg aggaaggcag    2640
ggcccgtgga gaagcggcca gcctggcacc ctatggacac gctccctga cttgcgcccc     2700 gctccctctt tctttgcagc aatgcctcct gcaccaccaa ctgcttagca ccctggcca     2760 aggtcatcca tgacaacttt ggtatcgtgg aaggactcat ggtatgagag ctggggaatg    2820
ggactgaggc tcccacccttt ctcatccaag actggctcct ccctgccggg gctgcgtgca   2880 accctgggt tggggttct ggggactggc tttcccataa tttccttca aggtggggag       2940 ggaggtagag gggtgatgtg gggagtacgc tgcagggcct cactccttt gcagaccaca    3000 gtccatgcca tcactgccac ccagaagact gtggatggcc cctccgggaa actgtggcgt    3060
gatggccgcg ggctctccca gaacatcatc cctgcctcta ctggcgctgc caaggctgtg    3120
ggcaaggtca tccctgagct gaacgggaag ctcactggca tggccttccg tgtccccact    3180
gccaacgtgt cagtggtgga cctgacctgc cgtctagaaa aacctgccaa atatgatgac    3240
atcaagaagg tggtgaagca ggcgtcggag ggccccctca agggcatcct gggctacact    3300
gagcaccagg tggtctcctc tgacttcaac agcgacaccc actcctccac ctttgacgct    3360
ggggctggca ttgccctcaa cgaccacttt gtcaagctca tttcctggta tgtggctggg    3420
gccagagact ggctcttaaa agtgcaggg tctggcgccc tctggtggct ggctcagaaa     3480
aagggccctg acaactcttt tcatcttcta ggtatgacaa cgaatttggc tacagcaaca    3540
gggtggtgga cctcatggcc cacatggcct ccaaggaggg aatggcgcgt ggcggcgggt    3600
ccggaggaga gggcagagga agtcttctaa catgcggtga cgtggaggag aatcctggcc    3660
caatggtgag caagggcgag gaggataaca tggccatcat caaggagttc atgcgcttca    3720
aggtgcacat ggagggctcc gtgaacggcc acgagttcga gatcgagggc gagggcgagg    3780
gccgccccta cgagggcacc cagaccgcca agctgaaggt gaccaagggt ggccccctgc    3840
ccttcgcctg gacatcctg tcccctcagt tcatgtacgg ctccaaggcc tacgtgaagc     3900
accccgccga catccccgac tacttgaagc tgtccttccc cgagggcttc aagtgggagc    3960
gcgtgatgaa cttcgaggac ggcggcgtgg tgaccgtgac ccaggactcc tccctgcagg    4020
acggcgagtt catctacaag gtgaagctgc gcggcaccaa cttccccctcc gacgccccg    4080 taatgcagaa gaagaccatg ggctgggagg cctcctccga gcggatgtac cccgaggacg    4140
gcgccctgaa gggcgagatc aagcagaggc tgaagctgaa ggacggcggc cactacgacg    4200
ctgaggtcaa gaccacctac aaggccaaga gcccgtgca gctgcccggc gcctacaacg    4260
tcaacatcaa gttggacatc acctcccaca acgaggacta caccatcgtg aacagtacg     4320 aacgcgccga gggcgccac tccaccggcg gcatggacga gctgtacaag tctagatcat    4380
aatcagcgga tccgcccctc tccctccccc ccccctaacg ttactggccg aagccgcttg    4440
gaataaggcc ggtgtgcgtt tgtctatatg ttattttcca ccatattgcc gtcttttggc    4500
aatgtgaggg cccggaaacc tggccctgtc ttcttgacga gcattcctag ggtctttcc    4560 cctctcgcca aaggaatgca aggtctgttg aatgtcgtga aggaagcagt tcctctggaa    4620
gcttcttgaa gacaaacaac gtctgtagcg acccttgca ggcagcggaa ccccccacct     4680
ggcgacaggt gcctctgcgg ccaaaagcca cgtgtataag atacacctgc aaaggcggca    4740
```

```
caacccccagt gccacgttgt gagttggata gttgtggaaa gagtcaaatg gctctcctca      4800
agcgtattca acaaggggct gaaggatgcc cagaaggtac cccattgtat gggatctgat      4860
ctggggcctc ggtacacatg ctttacatgt gtttagtcga ggttaaaaaa acgtctaggc      4920
cccccgaacc acggggacgt ggttttcctt tgaaaaacac gatgataata tggccacaac      4980
catggcgcgt atggctcggg gcattgaaca ggatgggctg cacgccgggt cacctgctgc      5040
ttgggtcgaa agactgtttg ggtatgattg ggctcagcag acaatcggct gctctgacgc      5100
cgccgtgttc aggctgagtg ctcagggacg ccccgtgctg tttgtcaaga ctgacctgtc      5160
aggggcactg aacgagctgc aggatgaggc agcccgcctg agctggctgg caaccacagg      5220
agtgccttgt gctgcagtcc tggacgtggt cactgaggcc ggacgagatt ggctgctgct      5280
gggagaagtg ccaggacagg acctgctgag ctcccacctg gcaccagctg agaaggtctc      5340
catcatggca gatgccatga ggagactgca tactctggac cccgccacct gccctttcga      5400
tcaccaggct aaacatcgca ttgagcgggc tcgcacacga atggaagcag gcctggtgga      5460
ccaggacgat ctggatgagg aacaccaggg actggctcct gcagagctgt ttgcaaggct      5520
gaaagccaga atgccagacg gcgaagatct ggtggtcacc catggagacg cttgcctgcc      5580
caacatcatg gtggagaatg gaagattcag tgggtttatt gattgtggcc gactgggagt      5640
cgccgacagg taccaggata tcgccctggc tacaagagac attgcagagg aactgtgcgg      5700
ggaatgggcc gatcggttcc tggtgctgta tggcattgct gctcccgaca gtcagaggat      5760 tgcttttttac aggctgctgg acgagttctt ttgaatctag acgcgcccgc gtacaagggc      5820
gaattccagc acactggcgg ccgttactag tggatccgag ctcggtacat cgataagctt      5880
agatcgagca aagaggaag agagagaccc tcactgctgg ggagtccctg ccacactcag      5940
tcccccacca cactgaatct cccctcctca cagttgccat gtagacccct tgaagagggg      6000
aggggcctag ggagccgcac cttgtcatgt accatcaata aagtaccctg tgctcaacca      6060
gttacttgtc ctgtcttatt ctagggtctg ggcagaggg gagggaagct gggcttgtgt      6120
caaggtgaga cattcttgct ggggagggac ctggtatgtt ctcctcagac tgagggtagg      6180
gcctccaaac agccttgctt gcttcgagaa ccatttgctt cccgctcaga cgtcttgagt      6240
gctacaggaa gctggcacca ctacttcaga gaacaaggcc ttttcctctc ctcgctccag      6300
tcctaggcta tctgctgttg gccaaacatg aagaagcta ttctgtgggc agccccaggg      6360
aggctgacag gtggaggaag tcagggctcg cactgggctc tgacgctgac tggttagtgg      6420
agctcagcct ggagctgagc tgcagcgggc aattccagct tggcctccgc agctgtgagg      6480
tcttgagcac gtgctctatt gctttctgtg ccctcgtgtc ttatctgagg acatcgtggc      6540
cagcccctaa ggtcttcaag caggattcat ctaggtaaac caagtaccta aaaccatgcc      6600
caaggcggta aggactatat aatgtttaaa aatcggtaaa aatgcccacc tcgcatagtt      6660
ttgaggaaga tgaactgaga tgtgtcaggg tgacttattt ccatcatcgt ccttagggga      6720
acttgggtag gggcaaggcg tgtagctggg acctaggtcc agacccctgg ctctgccact      6780
gaacggctca gttgctttgg gcagttactc ccgggcctca cttttgcacgt gtgcttacct      6840 agtggagaca aaagtacata cctcggtaga gcgcgcacgc ctgtaaccc agcactttgg      6900 gaggccaagg tgggtgtatc acctgaggtc aggagtttga ccagcctg gccaacatgg      6960 tgaaactccg tctctactaa aattacaaaa atcagccagg cttcatggca catgcctata      7020
gtcccagcta caggcatgct gaagcaggag aatcgcttgc accccggagg cagaggctgc      7080
agtgagctga gaccacacca ctgcactcca gcctaggcaa cagagtatga gactccatct      7140
```

```
caaaaaaaaa aaaagtacct acctcagagt tcaaactagt gaatattagg aagtgcttga      7200
gacagtgaca ccaaagtgca caataaatac tcgccagttt cattattatt aaagaatcca      7260
tttgaatgtc agctcaacac agcctcctat accgaggcat tgtgaaccgc atctccccag      7320
cttctccagg cttttccaag aatcaggcac actgtagcct gttggtctca gtgtatgaca      7380
gacacggagg aagcacatct ttagctgata cttaaacaga gaccctgagc gcacatacac      7440
ccgcgcacac atgcatggag cttcaccttc tctgtcattc tgcagtgacc aggagagcaa      7500
gagctcccac ctcccttcaa aacactgtgc ccatcccggg cactaaggcc tctttaaagc      7560
acggcacctc cacgagggag ggccacagcc acatacactc cacctggcag gtggacagcg      7620
tgagcacgtg gaccatagca gggacaaggt gccccggcca gccccaacgc cctctgccgc      7680
tgacagggac agaagccctc tccagctgcg tgtgctgcag aggccatgcg tagcctccag      7740
ctgcattcta ttccactcca gtgcctgggc cagttagcac cagtgtggaa gacagtgagc      7800
tggctccgga caacagggat ggaggaaagg tcccacattc acattcctga tacgtggaca      7860
aggtgagggg ccgcaatcgc tctggcagca ttttaaagat ggggaagtag cagacaccca      7920
cgcgtgaagg caggagagcc ccaactgtgg tggaaatggc cccagaatgg tagggccaag      7980
cctagctcca gacaccccag agccctggag aagccaagac tgaggagaa agcctgaggg      8040
aggagcgccc cagtccccag ggaccggcct ggtgcagagc tgcagctgat gttcccctct      8100
gtgcagcccc accctctgcc tcgctgagct ccctgctgcg agggcctcgg gtgcaagggg      8160
gaggcaggtc tctatctcat ggagctgtca gatgagacat cgcgatcgga gtcctcagcc      8220
tcgcttggcg gcggcggcgg gtcgctaagc gggaccgcag tgaaagcagg agactttcta      8280
gaaaaaaaca ccagttgtca accttggggc aggcaggaat cctgaagacg gacggcactc      8340
ctcctcctgc tgcctcaccc tctggcagcc cgtgagaagt accggaagcg agggcggggc      8400
cgcgggatgg cgagggagcg gcagggactg aactctctcc aaacccaccc tgacagggaa      8460
atgggccccg cctgtgtctt gggaactcag aggctgaggt caggcatgat ggctcacgcc      8520
tgtaattcca gcactttggg aggcagaggc gggtggatca cgacgtcagg agttcaaggc      8580
aagcctggcc aacatggtga acccccatct ctactaaaaa tgcaaaaatt agccaggtgt      8640
ggtggcgggc gccttggagg ctgaggcaag ataatcactt gaacctggga ggcggaggtt      8700
gtagtgagcc aaaaaaaaaa aaaaagaaa tagctgaagt cacagtagga gagaagctgc      8760
tgagcctcca gcaccctgac tctagggcct tggctttatg tctatctgca gtattttgt       8820
gatttttaaa aattcacttt cttgttgcgg tgtaacttac acagggtcaa atgcacaaat      8880
catggccctg actttagata aaaatctgcc cccacaaccc ttctgttcct tgccagtttt      8940
taaactgcct ctaaccaggg gaaccaccag agctggtggc cttgggaggt ttcagccctc      9000
ccgtcatgaa tggacatagc tcatccaact gccaaggag agagctgtgg gtctgggcca      9060
gccccaccag gtaactccca aagggcagcc cacagcaag atgtgaccca gtcattgcct       9120
gagggtctct ggggctgtgt tccaacccttt ctccccgctg tgtcccctg gaaggcccca      9180
tgcccagggg aggcgcctac cggtctccag actgggtgat gagccggcgg caggtctcca      9240
tctgcacgtc caggccgcgc ttcatgctgc acatctccat gtactcgtgc aggtgccggt      9300
tcatgtcgtt cttggccgtg ccaactccca gctgtggtgg ggcaggcagg ccatcgggg       9360
ttaacaggtg gcgttcacag cgcctctgtt gccccgcca ggaggccaac acgccaagag       9420
cagtggctgg gccgggggcc caggcagcca ttactgaagg ctcagatttt aaaataaacc      9480
agaccaaggc agaaggcagc gaatacacca ttgtttcctc tgcttttcct ggaaatcttt      9540
```

| | | | | |
|---|---|---|---|---|
| gcctatggag | gaatgcaaag | gtactgctgc | aggctgtgtt | cttttaagac tgataagagt | 9600 |
| ggtgaggaaa | gtcagtgtgg | gcgggatgga | gcagatccac | aggctcccag ggccacacag | 9660 |
| gttcctatgg | ggcccggctc | acccctcatc | ccctgtactg | cgctggtcct gggctgtccc | 9720 |
| ctcactgcac | tgtgagctcc | cgtaagggtt | agcgacaggt | tttcctcatc ctggcagacc | 9780 |
| cagacctcga | agggaattaa | ctctctctgt | gacccgtggc | atacaagcct ggctaactgc | 9840 |
| tgaaaggggc | ccaatcctct | taccattctc | tccttatcac | tttatttct cacctaaaag | 9900 |
| ccattttcag | acactaaaag | gaagactccc | atattggagg | tgccattgat tctgagacct | 9960 |
| gtcctgattt | cagaaatgtc | acacgtggaa | aacacggggc | tcagaatcaa agaaatccgg | 10020 |
| tctccctccc | cgggcccatt | ctgcagccca | cactctgagg | caggcggaga ggcagggccc | 10080 |
| aggcagcaca | aactcagtgc | cagggacagt | cgattaatta | gcgatcgca ggccgcccgc | 10140 |
| ggtggagctc | caattcgccc | tatagtgagt | cgtattacgc | gcgctcactg gccgtcgttt | 10200 |
| tacaacgtcg | tgactgggaa | aaccctggcg | ttacccaact | taatcgcctt gcagcacatc | 10260 |
| cccctttcgc | cagctggcgt | aatagcgaag | aggcccgcac | cgatcgccct tcccaacagt | 10320 |
| tgcgcagcct | gaatggcgaa | tggaaattgt | aagcgttaat | attttgttaa aattcgcgtt | 10380 |
| aaattttgt | taaatcagct | cattttttaa | ccaataggcc | gaaatcggca aaatcccta | 10440 |
| taaatcaaa | gaatagaccg | agatagggt | gagtgttgtt | ccagtttgga caagagtcc | 10500 |
| actattaaag | aacgtggact | ccaacgtcaa | agggcgaaaa | accgtctatc agggcgatgg | 10560 |
| cccactacgt | gaaccatcac | cctaatcaag | tttttgggg | tcgaggtgcc gtaaagcact | 10620 |
| aaatcggaac | cctaaaggga | gcccccgatt | tagagcttga | cggggaaagc cggcgaacgt | 10680 |
| ggcgagaaag | gaagggaaga | aagcgaaagg | agcgggcgct | agggcgctgg caagtgtagc | 10740 |
| ggtcacgctg | cgcgtaacca | ccacacccgc | cgcgcttaat | gcgccgctac agggcgcgtc | 10800 |
| ag | | | | | 10802 |

<210> SEQ ID NO 7
<211> LENGTH: 12541
<212> TYPE: DNA
<213> ORGANISM: Artificial Sequence
<220> FEATURE:
<223> OTHER INFORMATION: vector GT-MYC:ER

<400> SEQUENCE: 7

| | | | | |
|---|---|---|---|---|
| gattcattaa | tgcagctggc | acgacaggtt | tcccgactgg | aaagcgggca gtgagcgcaa | 60 |
| cgcaattaat | gtgagttagc | tcactcatta | ggcaccccag | gctttacact ttatgcttcc | 120 |
| ggctcgtatg | ttgtgtggaa | ttgtgagcgg | ataacaattt | cacacaggaa acagctatga | 180 |
| ccatgattac | gccaagctcg | aaattaaccc | tcactaaagg | gaacaaaagc tggtacgtta | 240 |
| attaaggaag | gtgaaggtcg | gagtcaacgg | gtgagttcgc | gggtggctgg ggggccctgg | 300 |
| gctgcgaccg | ccccgaacc | gcgtctacga | gccttgcggg | ctccgggtct ttgcagtcgt | 360 |
| atggggcag | ggtagctgtt | ccccgcaagg | agagctcaag | gtcagcgctc ggacctggcg | 420 |
| gagccccgca | cccaggctgt | ggcgccctgt | gcagctccgc | ccttgcggcg ccatctgccc | 480 |
| ggagcctcct | tccccctagtc | cccagaaaca | ggaggtccct | actcccgccc gagatcccga | 540 |
| cccggacccc | taggtggggg | acgctttctt | tcctttcgcg | ctctgcgggg tcacgtgtcg | 600 |
| cagaggagcc | cctcccccac | ggcctccggc | accgcaggcc | ccgggatgct agtgcgcagc | 660 |
| gggtgcatcc | ctgtccggat | gctgcgcctg | cggtagagcg | gccgccatgt tgcaaccggg | 720 |
| aaggaaatga | atgggcagcc | gttaggaaag | cctgccggtg | actaaccctg cgctcctgcc | 780 |

```
tcgatgggtg gagtcgcgtg tggcggggaa gtcaggtgga gcgaggctag ctggcccgat    840
ttctcctccg ggtgatgctt ttcctagatt attctctggt aaatcaaaga agtgggttta    900
tggaggtcct cttgtgtccc ctccccgcag aggtgtggtg gctgtggcat ggtgccaagc    960
cgggagaagc tgagtcatgg gtagttggaa aaggacattt ccaccgcaaa atggcccctc   1020
tggtggtggc cccttcctgc agcgccggct cacctcacgg ccccgccctt ccctgccag    1080 cctagcgttg acccgacccc aaaggccagg ctgtaaatgt caccgggagg attgggtgtc   1140
tgggcgcctc ggggaacctg cccttctccc cattccgtct tccggaaacc agatctccca   1200
ccgcaccctg gtctgaggtt aaatatagct gctgaccttt ctgtagctgg ggcctgggc   1260 tggggctctc tcccatccct tctccccaca cacatgcact tacctgtgct cccactcctg   1320
atttctggaa aagagctagg aaggacaggc aacttggcaa atcaaagccc tgggactagg   1380
gggttaaaat acagcttccc ctcttcccac ccgcccagt ctctgtccct tttgtaggag    1440
ggacttagag aaggggtggg cttgccctgt ccagttaatt tctgaccttt actcctgccc   1500
tttgagtttg atgatgctga gtgtacaagc gttttctccc taaagggtgc agctgagcta   1560
ggcagcagca agcattcctg gggtggcata gtggggtggt gaataccatg tacaaagctt   1620
gtgcccagac tgtgggtggc agtgcccac atggccgctt ctcctggaag ggcttcgtat    1680
gactgggggt gttgggcagc cctggagcct tcagttgcag ccatgcctta agccaggcca   1740
gcctggcagg gaagctcaag ggagataaaa ttcaacctct tgggccctcc tgggggtaag   1800
gagatgctgc attcgccctc ttaatgggga ggtggcctag ggctgctcac atattctgga   1860
ggagcctccc ctcctcatgc cttcttgcct cttgtctctt agatttggtc gtattgggcg   1920
cctggtcacc agggctgctt ttaactctgg taaagtggat attgttgcca tcaatgaccc   1980
cttcattgac ctcaactaca tggtgagtgc tacatggtga gccccaaagc tggtgtggga   2040
ggagccacct ggctgatggg cagccccttc atacccctcac gtattccccc aggtttacat   2100
gttccaatat gattccaccc atggcaaatt ccatggcacc gtcaaggctg agaacgggaa   2160
gcttgtcatc aatggaaatc ccatcaccat cttccaggag tgagtggaag acagaatgga   2220
agaaatgtgc tttggggagg caactaggat ggtgtgctc ccttgggtat atggtaacct    2280
tgtgtccctc aatatggtcc tgtccccatc tccccccac cccataggc gagatccctc     2340 caaaatcaag tggggcgatg ctggcgctga gtacgtcgtg gagtccactg gcgtcttcac   2400
caccatggag aaggctgggg tgagtgcagg agggcccgcg ggaggggaag ctgactcagc   2460
cctgcaaagg caggacccgg gttcataact gtctgcttct ctgctgtagg ctcatttgca   2520 gggggggagcc aaaagggtca tcatctctgc ccctctgct gatgccccca tgttcgtcat    2580
gggtgtgaac catgagaagt atgacaacag cctcaagatc atcaggtgag gaaggcaggg   2640
cccgtggaga agcggccagc ctggcaccct atggacacgc tcccctgact tgcgcccgc    2700 tccctctttc tttgcagcaa tgcctcctgc accaccaact gcttagcacc cctgccaag   2760 gtcatccatg acaactttgg tatcgtggaa ggactcatgg tatgagagct ggggaatggg   2820
actgaggctc ccacctttct catccaagac tggctcctcc ctgccggggc tgcgtgcaac   2880
cctggggttg ggggttctgg ggactggctt tccataatt tcctttcaag gtggggaggg    2940
aggtagaggg gtgatgtggg gagtacgctg cagggcctca ctcctttgc agaccacagt    3000 ccatgccatc actgccaccc agaagactgt ggatggcccc tccggaaaac tgtggcgtga   3060
tggccgcggg gctctccaga acatcatccc tgcctctact ggcgctgcca aggctgtggg   3120
caaggtcatc cctgagctga acgggaagct cactggcatg gccttccgtg tccccactgc   3180
```

```
caacgtgtca gtggtggacc tgacctgccg tctagaaaaa cctgccaaat atgatgacat    3240
caagaaggtg gtgaagcagg cgtcggaggg ccccctcaag ggcatcctgg gctacactga    3300
gcaccaggtg gtctcctctg acttcaacag cgacacccac tcctccacct ttgacgctgg    3360
ggctggcatt gccctcaacg accactttgt caagctcatt tcctggtatg tggctggggc    3420
cagagactgg ctcttaaaaa gtgcagggtc tggcgccctc tggtggctgg ctcagaaaaa    3480
gggccctgac aactcttttc atcttctagg tatgacaacg aatttggcta cagcaacagg    3540
gtggtggacc tcatggccca catggcctcc aaggagggaa tggcgcgtgg cggcgggtcc    3600
ggaggagagg gcagaggaag tcttctaaca tgcggtgacg tggaggagaa tcctggcccg    3660
gcgcgtcgcg tctcgaccac catgcccctc aacgttagct tcaccaacag gaactatgac    3720
ctcgactacg actcggtgca gccgtatttc tactgcgacg aggaggagaa cttctaccag    3780
cagcagcagc agagcgagct gcagcccccg gcgcccagcg aggatatctg gaagaaattc    3840
gagctgctgc ccaccccgcc cctgtcccct agccgccgct ccgggctctg ctcgccctcc    3900
tacgttgcgg tcacacccct tctcccttcgg ggagacaacg acggcggtgg cgggagcttc    3960
tccacggccg accagctgga gatggtgacc gagctgctgg gaggagacat ggtgaaccag    4020
agtttcatct gcgacccgga cgacgagacc ttcatcaaaa acatcatcat ccaggactgt    4080
atgtggagcg gcttctcggc cgccgccaag ctcgtctcag agaagctggc ctcctaccag    4140
gctgcgcgca agacagcgg cagcccgaac cccgccgcg ccacagcgt ctgctccacc    4200 tccagcttgt acctgcagga tctgagcgcc gccgcctcag agtgcatcga cccctcggtg    4260
gtcttcccct accctctcaa cgacagcagc tcgcccaagt cctgcgcctc gcaagactcc    4320
agcgccttct ctccgtcctc ggattctctg ctctcctcga cggagtcctc cccgcagggc    4380
agccccgagc cctggtgct ccatgaggag acaccgccca ccaccagcag cgactctgag    4440
gaggaacaag aagatgagga agaaatcgat gttgtttctg tggaaaagag gcaggctcct    4500
ggcaaaaggt cagagtctgg atcaccttct gctggaggcc acagcaaacc tcctcacagc    4560
ccactggtcc tcaagaggtg ccacgtctcc acacatcagc acaactacgc agcgcctccc    4620
tccactcgga aggactatcc tgctgccaag agggtcaagt ggacagtgt cagagtcctg    4680 agacagatca gcaacaaccg aaaatgcacc agccccaggt cctcggacac cgaggagaat    4740
gtcaagaggc gaacacacaa cgtcttggag cgccagagga ggaacgagct aaaacgagc    4800 tatttttgccc tgcgtgacca gatcccggag ttggaaaaca atgaaaaggc ccccaaggta    4860
gttatcctta aaaaagccac agcatacatc ctgtccgtcc aagcagagga gcaaaagctc    4920
atttctgaag aggacttgtt gcggaaacga cgagaacagt tgaaacacaa acttgaacag    4980
ctacgggatc cacgaaatga aatgggtgct tcaggagaca tgagggctgc caacctttgg    5040
ccaagccctc ttgtgattaa gcacactaag aagaatagcc ctgccttgtc cttgacagct    5100
gaccagatgg tcagtgcctt gttggatgct gaaccgccca tgatctattc tgaatatgat    5160
ccttctagac cctttcagtga agcctcaatg atgggcttat tgaccaacct agcagatagg    5220
gagctggttc atatgatcaa ctgggcaaag agagtgccag ctttgggga cttgaatctc    5280 catgatcagg tccaccttct cgagtgtgcc tggctggaga ttctgatgat tggtctcgtc    5340
tggcgctcca tggaacaccc ggggaagctc ctgtttgctc ctaacttgct cctggacagg    5400
aatcaaggta aatgtgtgga aggcatggtg gagatctttg acatgttgct tgctacgtca    5460
agtcggttcc gcatgatgaa cctgcagggt gaagagtttg tgtgcctcaa atccatcatt    5520
ttgcttaatt ccggagtgta cacgtttctg tccagcacct tgaagtctct ggaagagaag    5580
```

```
gaccacatcc accgtgtcct ggacaagatc acagacactt tgatccacct gatggccaaa    5640
gctggcctga ctctgcagca gcagcatcgc cgcctagctc agctccttct cattctttcc    5700
catatccggc atatgagtaa caaacgcatg gagcatctct acaacatgaa atgcaaaaac    5760
gtggtacccc tctatgacct gctcctggag atgttggatg cccaccgcct tcatgcccca    5820
gccagtcgca tgggagtgcc cccagaggag cccagccaga cccagctggc caccaccagc    5880
tccacttcag cacattcctt acaaacctac tacatacccc cggaagcaga gggcttcccc    5940
aacacgatct gagagctagg tcgacggatc cgcccctctc cctccccccc ccctaacgtt    6000
actggccgaa gccgcttgga ataaggccgg tgtgcgtttg tctatatgtt attttccacc    6060
atattgccgt cttttggcaa tgtgagggcc cggaaacctg gccctgtctt cttgacgagc    6120
attcctaggg gtcttttccc ctcgccaaa ggaatgcaag gtctgttgaa tgtcgtgaag     6180
gaagcagttc ctctggaagc ttcttgaaga caaacaacgt ctgtagcgac cctttgcagg    6240
cagcggaacc ccccacctgg cgacaggtgc ctctgcggcc aaaagccacg tgtataagat    6300
acacctgcaa aggcggcaca acccagtgc cacgttgtga gttggatagt tgtggaaaga    6360
gtcaaatggc tctcctcaag cgtattcaac aaggggctga aggatgccca gaaggtaccc    6420
cattgtatgg gatctgatct ggggcctcgg tacacatgct ttacatgtgt ttagtcgagg    6480
ttaaaaaaac gtctaggccc cccgaaccac ggggacgtgg ttttcctttg aaaacacga    6540
tgataatatg ccacaacca tggcgcgtat gaaaaagccc gagctgactg ccacctctgt    6600
cgagaagttc ctgattgaaa agtttgattc cgtgagtgac ctgatgcagc tgagcgaggg    6660
cgaggaatcc cggccttct cttttgacgt gggcggaagg ggctacgtgc tgagagtcaa    6720
ctcttgcgcc gacggattct ataaggatcg ctacgtgtat cgacactttg ctagtgccgc    6780
tctgcccatc cctgaggtgc tggacattgg cgagttcagc gaatccctga catactgtat    6840
ctccaggaga gcccagggag tgactctgca ggatctgcct gagaccgaac tgcctgccgt    6900
gctgcagcct gtggctgaag ctatggacgc tatcgcagcc gctgatctgt cacagactag    6960
cggggttcggc ccatttggcc cccagggaat tgggcagtac accacatgga gagactttat    7020
ctgcgcaatt gccgatcccc acgtgtatca ttggcagaca gtcatggacg ataccgtgag    7080
cgccagtgtc gctcaggcac tggacgagct gatgctgtgg gcagaggatt gtcctgaagt    7140
gaggcacctg gtccatgctg acttcgggag caacaatgtg ctgaccgata cggcagaat    7200
cacagccgtc attgactgga gtgaggctat gtttggcgat tcacagtacg aagtggctaa    7260
tatcttcttt tggcgaccct ggctggcatg catggagcag cagacccgct atttcgagcg    7320
gcgccatcct gaactggcag gtctccaag actgcgggcc tacatgctgc ggattggcct    7380
ggaccagctg tatcagagcc tggtggatgg aaatttgac gatgcagcat gggcacaggg    7440
gcggtgcgac gctatcgtgc gcagcggagc aggaactgtg ggaagaaccc agattgcccg    7500
aaggtccgct gcagtgtgga cagatgggt cgtggaggtg ctggcagata gcggaaatag    7560
gagaccaagt acaagaccac gggcaaaaga gtaatctaga cgcgtatcga taagcttaga    7620
tcgagcacaa aggaagaga gagaccctca ctgctgggga gtccctgcca cactcagtcc    7680
cccaccacac tgaatctccc ctcctcacag ttgccatgta gacccccttga agaggggagg   7740
ggcctaggga gccgcacctt gtcatgtacc atcaataaag taccctgtgc tcaaccagtt   7800
acttgtcctg tcttattcta gggtctgggg cagaggggag ggaagctggg cttgtgtcaa   7860
ggtgagacat tcttgctggg gagggacctg gtatgttctc ctcagactga gggtagggcc   7920
tccaaacagc cttgcttgct tcgagaacca tttgcttccc gctcagacgt cttgagtgct   7980
```

```
acaggaagct ggcaccacta cttcagagaa caaggccttt tcctctcctc gctccagtcc    8040
taggctatct gctgttggcc aaacatggaa gaagctattc tgtgggcagc cccagggagg    8100
ctgacaggtg gaggaagtca gggctcgcac tgggctctga cgctgactgg ttagtggagc    8160
tcagcctgga gctgagctgc agcgggcaat tccagcttgg cctccgcagc tgtgaggtct    8220
tgagcacgtg ctctattgct ttctgtgccc tcgtgtctta tctgaggaca tcgtggccag    8280
cccctaaggt cttcaagcag gattcatcta ggtaaaccaa gtacctaaaa ccatgcccaa    8340
ggcggtaagg actatataat gtttaaaaat cggtaaaaat gcccacctcg catagttttg    8400
aggaagatga actgagatgt gtcagggtga cttatttcca tcatcgtcct taggggaact    8460
tgggtagggg caaggcgtgt agctgggacc taggtccaga cccctggctc tgccactgaa    8520
cggctcagtt gctttgggca gttactcccg ggcctcactt tgcacgtgtg cttacctagt    8580
ggagacaaaa gtacatacct cggtagagcg cgcacgcctg taaccccagc actttgggag    8640
gccaaggtgg gtgtatcacc tgaggtcagg agtttgagac cagcctggcc aacatggtga    8700
aactccgtct ctactaaaat tacaaaaatc agccaggctt catggcacat gcctatagtc    8760
ccagctacag gcatgctgaa gcaggagaat cgcttgcacc ccggaggcag aggctgcagt    8820
gagctgagac cacaccactg cactccagcc taggcaacag agtatgagac tccatctcaa    8880
aaaaaaaaaa agtacctacc tcagagttca aactagtgaa tattaggaag tgcttgagac    8940
agtgacacca aagtgcacaa taaatactcg ccagtttcat tattattaaa gaatccattt    9000
gaatgtcagc tcaacacagc tcctataccc gaggcattgt gaaccgcatc tccccagctt    9060
ctccaggctt ttccaagaat cagggacact gtagcctgtt ggtctcagtg tatgacagac    9120
acggaggaag cacatctttta gctgatactt aaacagagac cctgagcgca catacacccg    9180
cgcacacatg catggagctt caccttctct gtcattctgc agtgaccagg agagcaagag    9240
ctcccacctc ccttcaaaac actgtgccca tcccgggcac taaggcctct ttaaagcacg    9300
gcacctccac gagggagggc cacagccaca tacactccac ctggcaggtg gacagcgtga    9360
gcacgtggac catagcaggg acaaggtgcc ccggccagcc caacgccct ctgccgctga    9420
cagggacaga agccctctcc agctgcgtgt gctgcagagg ccatgcgtag cctccagctg    9480
cattctattc cactccagtg cctgggccag ttagcaccag tgtggaagac agtgagctgg    9540
ctccggacaa cagggatgga ggaaaggtcc cacattcaca ttcctgatac gtggacaagg    9600
tgaggggccg caatcgctct ggcagcattt taaagatggg gaagtagcag acacccacgc    9660
gtgaaggcag gagagcccca actgtggtgg aaatggcccc agaatggtag ggccaagcct    9720
agctccagac accccagagc cctggagaag ccaagactga gggagaaagc ctgagggagg    9780
agcgccccag tccccaggga ccggcctggt gcagagctgc agctgatgtt cccctctgtg    9840
cagcccacc ctctgcctcg ctgagctccc tgctgcgagg gcctcgggtg caaggggag    9900
gcaggtctct atctcatgga gctgtcagat gagacatcgc gatcggagtc ctcagcctcg    9960
cttggcggcg gcggcgggtc gctaagcggg accgcagtga aagcaggaga ctttctagaa    10020
aaaaacacca gttgtcaacc ttggggcagg caggaatcct gaagacggac ggcactcctc    10080
ctcctgctgc ctcaccctct ggcagcccgt gagaagtacc ggaagcgagg gcggggccgc    10140
gggatggcga gggagcggca gggactgaac tctctccaaa cccaccctga cagggaaatg    10200
ggcccccgcct gtgtcttggg aactcagagg ctgaggtcag gcatgatggc tcacgcctgt    10260
aattccagca ctttgggagg cagaggcggg tggatcacga cgtcaggagt tcaaggcaag    10320
cctggccaac atggtgaaac cccatctcta ctaaaaatgc aaaaattagc caggtgtggt    10380
```

```
ggcgggcgcc ttggaggctg aggcaagata atcacttgaa cctgggaggc ggaggttgta    10440
gtgagccaaa aaaaaaaaaa aagaaatag ctgaagtcac agtaggagag aagctgctga     10500
gcctccagca ccctgactct agggccttgg ctttatgtct atctgcagta tttttgtgat    10560
ttttaaaaat tcactttctt gttgcggtgt aacttacaca gggtcaaatg cacaaatcat    10620
ggccctgact ttagataaaa atctgccccc acaacccttc tgttccttgc cagttttaa     10680 actgcctcta accaggggaa ccaccagagc tggtggcctt gggaggtttc agccctcccg    10740
tcatgaatgg acatagctca tccaactgcc aagggagaga gctgtgggtc tgggccagcc    10800
ccaccaggta actcccaaag ggcagcccca cagcaagatg tgacccagtc attgcctgag    10860
ggtctctggg gctgtgttcc aacctttctc cccgctgtgt cccctggaa ggccccatgc     10920 ccaggggagg cgcctaccgg tctccagact gggtgatgag ccggcggcag gtctccatct    10980
gcacgtccag gccgcgcttc atgctgcaca tctccatgta ctcgtgcagg tgccggttca    11040
tgtcgttctt ggccgtggcc aactccagct gtggtgggc aggcagggcc atcggggtta    11100
acaggtggcg ttcacagcgc ctctgttgcc cccgccagga ggccaacacg ccaagagcag    11160
tggctgggcc ggggggcccag gcagccatta ctgaaggctc agattttaaa ataaaccaga   11220
ccaaggcaga aggcagcgaa tacaccattg tttcctctgc ttttcctgga aatctttgcc    11280
tatggaggaa tgcaaaggta ctgctgcagg ctgtgttctt ttaagactga taagagtggt    11340
gaggaaagtc agtgtgggcg ggatggagca gatccacagg ctcccagggc cacacaggtt    11400
cctatggggc ccggctcacc cctcatcccc tgtactgcgc tggtcctggg ctgtcccctc    11460
actgcactgt gagctcccgt aagggttagc gacaggtttt cctcatcctg gcagacccag    11520
acctcgaagg gaattaactc tctctgtgac ccgtggcata caagcctggc taactgctga    11580
aaggggccca atcctcttac cattctctcc ttatcacttt attttctcac ctaaaagcca    11640
ttttcagaca ctaaaaggaa gactcccata ttggaggtgc cattgattct gagacctgtc    11700
ctgatttcag aaatgtcaca cgtggaaaac acggggctca gaatcaaaga aatccggtct    11760
ccctccccgg gccattctg cagcccacac tctgaggcag gcggagaggc agggcccagg     11820
cagcacaaac tcagtgccag ggacagtcga ttaattaagc gatcgcaggc cgccaccgcg    11880
gtggagctcc aattcgccct atagtgagtc gtattacgcg cgctcactgg ccgtcgtttt    11940
acaacgtcgt gactgggaaa accctggcgt tacccaactt aatcgccttg cagcacatcc    12000 cccttcgcc agctggcgta atagcgaaga ggcccgcacc gatcgccctt cccaacagtt     12060
gcgcagcctg aatggcgaat ggaaattgta agcgttaata ttttgttaaa attcgcgtta    12120
aatttttgtt aaatcagctc attttttaac caataggccg aaatcggcaa atcccttat     12180 aaatcaaaag aatagaccga gatagggttg agtgttgttc cagtttggaa caagagtcca    12240
ctattaaaga acgtggactc caacgtcaaa gggcgaaaaa ccgtctatca gggcgatggc    12300
ccactacgtg aaccatcacc ctaatcaagt tttttggggt cgaggtgccg taaagcacta    12360
aatcggaacc ctaaagggag cccccgattt agagcttgac ggggaaagcc ggcgaacgtg    12420
gcgagaaagg aagggaagaa agcgaaagga gcgggcgcta gggcgctggc aagtgtagcg    12480
gtcacgctgc gcgtaaccac cacacccgcc gcgcttaatg cgccgctaca gggcgcgtca    12540
g                                                                   12541
```

<210> SEQ ID NO 8
<211> LENGTH: 12636
<212> TYPE: DNA
<213> ORGANISM: Artificial Sequence
<220> FEATURE:
<223> OTHER INFORMATION: vector GT-iCherry

<400> SEQUENCE: 8

| | | | | | |
|---|---|---|---|---|---|
| gattcattaa | tgcagctggc | acgacaggtt | tcccgactgg | aaagcgggca | gtgagcgcaa | 60 |
| cgcaattaat | gtgagttagc | tcactcatta | ggcaccccag | gctttacact | ttatgcttcc | 120 |
| ggctcgtatg | ttgtgtggaa | ttgtgagcgg | ataacaattt | cacacaggaa | acagctatga | 180 |
| ccatgattac | gccaagctcg | aaattaaccc | tcactaaagg | gaacaaaagc | tggtacgtta | 240 |
| attaaaggga | aggtgaaggt | cggagtcaac | gggtgagttc | gcggtggct | gggggggccct | 300 |
| gggctgcgac | cgccccgaa | ccgcgtctac | gagccttgcg | ggctccgggt | ctttgcagtc | 360 |
| gtatggggc | agggtagctg | ttccccgcaa | ggagagctca | aggtcagcgc | tcggacctgg | 420 |
| cggagccccg | cacccaggct | gtggcgccct | gtgcagctcc | gcccttgcgg | cgccatctgc | 480 |
| ccggagcctc | cttcccctag | tccccagaaa | caggaggtcc | ctactcccgc | ccgagatccc | 540 |
| gacccggacc | cctaggtggg | ggacgctttc | tttcctttcg | cgctctgcgg | ggtcacgtgt | 600 |
| cgcagaggag | cccctccccc | acggcctccg | gcaccgcagg | cccgggatg | ctagtgcgca | 660 |
| gcgggtgcat | ccctgtccgg | atgctgcgcc | tgcggtagag | cggccgccat | gttgcaaccg | 720 |
| ggaaggaaat | gaatgggcag | ccgttaggaa | agcctgccgg | tgactaaccc | tgcgctcctg | 780 |
| cctcgatggg | tggagtcgcg | tgtggcgggg | aagtcaggtg | gagcgaggct | agctggcccg | 840 |
| atttctcctc | cgggtgatgc | ttttcctaga | ttattctctg | gtaaatcaaa | gaagtgggtt | 900 |
| tatggaggtc | ctcttgtgtc | ccctcccgc | agaggtgtgg | tggctgtggc | atggtgccaa | 960 |
| gccgggagaa | gctgagtcat | gggtagttgg | aaaaggacat | tccaccgca | aaatggcccc | 1020 |
| tctggtggtg | gcccttcct | gcagcgccgg | ctcacctcac | ggccccgccc | ttccctgcc | 1080 |
| agcctagcgt | tgacccgacc | ccaaaggcca | ggctgtaaat | gtcaccggga | ggattgggtg | 1140 |
| tctgggcgcc | tcggggaacc | tgcccttctc | cccattccgt | cttccggaaa | ccagatctcc | 1200 |
| caccgcaccc | tggtctgagg | ttaaatatag | ctgctgacct | ttctgtagct | ggggggcctgg | 1260 |
| gctgggctc | tctcccatcc | cttctcccca | cacacatgca | cttacctgtg | ctcccactcc | 1320 |
| tgatttctgg | aaaagagcta | ggaaggacag | gcaacttggc | aaatcaaagc | cctgggacta | 1380 |
| gggggttaaa | atacagcttc | ccctcttccc | acccgcccca | gtctctgtcc | cttttgtagg | 1440 |
| agggacttag | agaagggtg | ggcttgccct | gtccagttaa | tttctgacct | ttactcctgc | 1500 |
| cctttgagtt | tgatgatgct | gagtgtacaa | gcgttttctc | cctaaagggt | gcagctgagc | 1560 |
| taggcagcag | caagcattcc | tggggtggca | tagtggggtg | gtgaatacca | tgtacaaagc | 1620 |
| ttgtgcccag | actgtgggtg | gcagtgcccc | acatggccgc | ttctcctgga | agggcttcgt | 1680 |
| atgactgggg | gtgttgggca | gccctggagc | cttcagttgc | agccatgcct | taagccaggc | 1740 |
| cagcctggca | gggaagctca | agggagataa | aattcaacct | cttgggccct | cctgggggta | 1800 |
| aggagatgct | gcattcgccc | tcttaatggg | gaggtggcct | agggctgctc | acatattctg | 1860 |
| gaggagcctc | ccctcctcat | gccttcttgc | ctcttgtctc | ttagatttgg | tcgtattggg | 1920 |
| cgcctggtca | ccagggctgc | ttttaactct | ggtaaagtgg | atattgttgc | catcaatgac | 1980 |
| cccttcattg | acctcaacta | catggtgagt | gctacatggt | gagccccaaa | gctggtgtgg | 2040 |
| gaggagccac | ctggctgatg | gcagcccct | tcatacccct | acgtattccc | ccaggtttac | 2100 |
| atgttccaat | atgattccac | ccatggcaaa | ttcatggca | ccgtcaaggc | tgagaacggg | 2160 |
| aagcttgtca | tcaatggaaa | tcccatcacc | atcttccagg | agtgagtgga | agacagaatg | 2220 |

```
gaagaaatgt gctttgggga ggcaactagg atggtgtggc tcccttgggt atatggtaac    2280
cttgtgtccc tcaatatggt cctgtcccca tctccccccc acccccatag gcgagatccc    2340
tccaaaatca agtggggcga tgctggcgct gagtacgtcg tggagtccac tggcgtcttc    2400
accaccatgg agaaggctgg ggtgagtgca ggagggcccg cgggagggga agctgactca    2460
gccctgcaaa ggcaggaccc gggttcataa ctgtctgctt ctctgctgta ggctcatttg    2520
cagggggag ccaaaaggt catcatctct gccccctctg ctgatgcccc catgttcgtc     2580
atgggtgtga accatgagaa gtatgacaac agcctcaaga tcatcaggtg aggaaggcag    2640
ggcccgtgga gaagcggcca gcctggcacc ctatggacac gctccctga cttgcgcccc     2700
gctccctctt tctttgcagc aatgcctcct gcaccaccaa ctgcttagca ccctggcca     2760
aggtcatcca tgacaacttt ggtatcgtgg aaggactcat ggtatgagag ctggggaatg    2820
ggactgaggc tcccacctt ctcatccaag actggctcct ccctgccggg gctgcgtgca     2880
accctggggt tgggggttct ggggactggc tttcccataa tttcctttca aggtggggag    2940
ggaggtagag gggtgatgtg gggagtacgc tgcagggcct cactccttt gcagaccaca     3000
gtccatgcca tcactgccac ccagaagact gtggatggcc cctccgggaa actgtggcgt    3060
gatgccgcg gggctctcca gaacatcatc cctgcctcta ctggcgctgc caaggctgtg     3120
ggcaaggtca tccctgagct gaacgggaag ctcactggca tggccttccg tgtccccact    3180
gccaacgtgt cagtggtgga cctgacctgc cgtctagaaa aacctgccaa atatgatgac    3240
atcaagaagg tggtgaagca ggcgtcggag ggccccctca agggcatcct gggctacact    3300
gagcaccagg tggtctcctc tgacttcaac agcgacaccc actcctccac ctttgacgct    3360
ggggctggca ttgcccctcaa cgaccacttt gtcaagctca tttcctggta tgtggctggg    3420
gccagagact ggctcttaaa aagtgcaggg tctggcgccc tctggtggct ggctcagaaa    3480
aagggccctg acaactcttt tcatcttcta ggtatgacaa cgaatttggc tacagcaaca    3540
gggtggtgga cctcatggcc cacatggcct ccaaggaggg aatggcgcgt ggcggcgggt    3600
ccggaggaga gggcagagga agtcttctaa catgcggtga cgtggaggag aatcctggcc    3660
cggcgcgccc catgccaaag agacccagac cctctagatt agataaaagt aaagtgatta    3720
acagcgcatt agagctgctt aatgaggtcg gaatcgaagg tttaacaacc cgtaaactcg    3780
cccagaagct tggtgtagag cagcctacac tgtattggca tgtaaaaaat aagcgggctt    3840
tgctcgacgc cttagccatt gagatgttag ataggcacca tactcacttt tgccctttaa    3900
aaggggaaag ctggcaagat tttttacgca ataacgctaa aagttttaga tgtgctttac    3960
taagtcatcg caatggagca aaagtacatt cagatacacg gcctacagaa aaacagtatg    4020
aaactctcga aaatcaatta gccttttat gccaacaagg ttttcacta gagaacgcgt      4080
tatatgcact cagcgctgtg gggcatttta ctttaggttg cgtattggaa gatcaagagc    4140
atcaagtcgc taagaagaa agggaaacac ctactactga tagtatgccg ccattattac     4200
gacaagctat cgaattattt gatcaccaag gtgcagagca gccttctta ttcggccttg     4260
aattgatcat atgcggatta gaaaaacaac ttaaatgtga agtgggtcc gcgtacagcc     4320
gcgcgcgtac gaaaaacaat tacgggtcta ccatcgaggg cctgctcgat ctcccggacg    4380
acgacgcccc cgaagaggcg gggctggcgg ctccgcgcct gtcctttctc cccgcgggac    4440
acacgcgcag actgtcgacg gcccccccga ccgatgtcag cctgggggac gagctccact    4500
tagacgcgcga ggacgtggcg atggcgcatg ccgacgcgct agacgatttc gatctggaca    4560
tgttggggga cggggattcc ccgggtccgg gatttacccc ccacgactcc gccccctacg    4620
```

```
gcgctctgga tatggccgac ttcgagtttg agcagatgtt taccgatgcc cttggaattg    4680
acgagtacgg tgggtagggg atccgcccct ctccctcccc cccccctaac gttactggcc    4740
gaagccgctt ggaataaggc cggtgtgcgt ttgtctatat gttattttcc accatattgc    4800
cgtcttttgg caatgtgagg gcccggaaac ctggccctgt cttcttgacg agcattccta    4860
ggggtctttc ccctctcgcc aaaggaatgc aaggtctgtt gaatgtcgtg aaggaagcag    4920
ttcctctgga agcttcttga agacaaacaa cgtctgtagc gacccttttgc aggcagcgga    4980 accccccacc tggcgacagg tgcctctgcg gccaaaagcc acgtgtataa gatacacctg    5040
caaaggcggc acaaccccag tgccacgttg tgagttggat agttgtggaa agagtcaaat    5100
ggctctcctc aagcgtattc aacaaggggc tgaaggatgc ccagaaggta ccccattgta    5160
tgggatctga tctggggcct cggtacacat gctttacatg tgtttagtcg aggttaaaaa    5220
aacgtctagg cccccccgaac cacggggacg tggttttcct ttgaaaaaca cgatgataat    5280
atggccacaa ccatggcgcg tatggctcgg ggcattgaac aggatgggct gcacgccggg    5340
tcacctgctg cttgggtcga aagactgttt gggtatgatt gggctcagca gacaatcggc    5400
tgctctgacg ccgccgtgtt caggctgagt gctcagggac gccccgtgct gtttgtcaag    5460
actgacctgt caggggcact gaacgagctg caggatgagg cagcccgcct gagctggctg    5520
gcaaccacag gagtgccttg tgctgcagtc ctggacgtgg tcactgaggc cggacgagat    5580
tggctgctgc tgggagaagt gccaggacag gacctgctga gctcccacct ggcaccagct    5640
gagaaggtct ccatcatggc agatgccatg aggagactgc atactctgga ccccgccacc    5700 tgcccttttcg atcaccaggc taaacatcgc attgagcggg ctcgcacacg aatggaagca    5760
ggcctggtgg accaggacga tctggatgag gaacaccagg gactggctcc tgcagagctg    5820
tttgcaaggc tgaaagccag aatgccagac ggcgaagatc tggtggtcac ccatggagac    5880
gcttgcctgc ccaacatcat ggtggagaat ggaagattca gtgggtttat tgattgtggc    5940
cgactgggag tcgccgacag gtaccaggat atcgccctgg ctacaagaga cattgcagag    6000
gaactgtgcg gggaatgggc cgatcggttc ctggtgctgt atggcattgc tgctcccgac    6060
agtcagagga ttgctttttta caggctgctg gacgagttcc tttgaatcta gacgcgtatc    6120
gaaccagaca tgataagata cattgatgag tttggacaaa ccacaactag aatgcagtga    6180
aaaaaatgct ttatttgtga aatttgtgat gctattgctt tatttgtaac cattataagc    6240
tgcaataaac aagttaacaa caacaattgc attcatttta tgtttcaggt tcaggggggag    6300 gtgtgggagg ttttttaaag caagtaaaac ctctacaaat gtggtatggc tgattatgat    6360
cctgcaagcc tcgtcgtcct ggccggacca cgctatctgt gcaaggtccc cggccccgga    6420
cgcgcgctcc atgagcagag cgcccgccgc cgaggcgaag actcgggcgg cgccctgccc    6480
gtcccaccag gtcaacaggc ggtaaccggc ctcttcatcg ggaatgcgcg cgaccttcag    6540
catcgccggc atgtccccct ggcggacggg aagtatccag ctcgaccaag cttggcgaga    6600
ttttcaggag ctaaggaagc ttcgtcttca ctcgagttta ctccctatca gtgatagaga    6660
acgtatgtcg agtttactcc ctatcagtga tagagaacga tgtcgagttt actccctatc    6720
agtgatagag aacgtatgtc gagtttactc cctatcagtg atagagaacg tatgtcgagt    6780
ttactcccta tcagtgatag agaacgtatg tcgagtttat ccctatcagt gatagagaac    6840
gtatgtcgag tttactccct atcagtgata gagaacgtat gtcgaggtag gcgtgtacgg    6900
tgggaggcct atataagcag agctcgttta gtgaaccgtc agatcgcctg gaaatcgatg    6960
ccaccatggt gagcaagggc gaggaggata acatggccat catcaaggag ttcatgcgct    7020
```

```
tcaaggtgca catggagggc tccgtgaacg gccacgagtt cgagatcgag ggcgagggcg      7080
agggccgccc ctacgagggc acccagaccc caagctgaa ggtgaccaag ggtggccccc      7140
tgcccttcgc ctgggacatc ctgtcccctc agttcatgta cggctccaag gcctacgtga      7200
agcaccccgc cgacatcccc gactacttga agctgtcctt ccccgagggc ttcaagtggg      7260
agcgcgtgat gaacttcgag gacggcggcg tggtgaccgt gacccaggac tcctccctgc      7320
aggacggcga gttcatctac aaggtgaagc tgcgcggcac caacttcccc tccgacggcc      7380
ccgtaatgca gaagaagacc atgggctggg aggcctcctc cgagcggatg taccccgagg      7440
acggcgccct gaagggcgag atcaagcaga ggctgaagct gaaggacggc ggccactacg      7500
acgctgaggt caagaccacc tacaaggcca agaagcccgt gcagctgccc ggcgcctaca      7560
acgtcaacat caagttggac atcacctccc acaacgagga ctacaccatc gtggaacagt      7620
acgaacgcgc cgagggccgc cactccaccg gcggcatgga cgagctgtac aagtctagat      7680
cataatcagc cggatccatcg atggatccaa gcttagatcg agcacaagag gaagagagag      7740
accctcactg ctggggagtc cctgccacac tcagtccccc accacactga atctcccctc      7800
ctcacagttg ccatgtagac cccttgaaga ggggaggggc ctaggagcc gcaccttgtc      7860 atgtaccatc aataaagtac cctgtgctca accagttact tgtcctgtct tattctaggg      7920
tctggggcag aggggaggga agctgggctt gtgtcaaggt gagacattct tgctggggag      7980
ggacctggta tgttctcctc agactgaggg tagggcctcc aaacagcctt gcttgcttcg      8040
agaaccattt gcttcccgct cagacgtctt gagtgctaca ggaagctggc accactactt      8100
cagagaacaa ggccttttcc tctcctcgct ccagtcctag gctatctgct gttggccaaa      8160
catggaagaa gctattctgt gggcagcccc agggaggctg acaggtggag gaagtcaggg      8220
ctcgcactgg gctctgacgc tgactggtta gtggagctca gcctggagct gagctgcagc      8280
gggcaattcc agcttggcct ccgcagctgt gaggtcttga gcacgtgctc tattgctttc      8340
tgtgccctcg tgtcttatct gaggacatcg tggccagccc ctaaggtctt caagcaggat      8400
tcatctaggt aaaccaagta cctaaaacca tgcccaaggc ggtaaggact atataatgtt      8460
taaaaatcgg taaaaatgcc cacctcgcat agttttgagg aagatgaact gagatgtgtc      8520
agggtgactt atttccatca tcgtccttag ggaacttgg gtaggggcaa ggcgtgtagc      8580
tgggacctag gtccagaccc ctggctctgc cactgaacgg ctcagttgct ttgggcagtt      8640
actcccgggc ctcactttgc acgtgtgctt acctagtgga gacaaaagta catacctcgg      8700
tagagcgcgc acgcctgtaa ccccagcact ttgggaggcc aaggtgggtg tatcacctga      8760
ggtcaggagt ttgagaccag cctggccaac atggtgaaac tccgtctcta ctaaaattac      8820
aaaaatcagc caggcttcat ggcacatgcc tatagtccca gctacaggca tgctgaagca      8880
ggagaatcgc ttgcaccccg gaggcagagg ctgcagtgag ctgagaccac accactgcac      8940
tccagcctag gcaacagagt atgagactcc atctcaaaaa aaaaaaagt acctacctca      9000 gagttcaaac tagtgaatat taggaagtgc ttgagacagt gacaccaaag tgcacaataa      9060
atactcgcca gtttcattat tattaaagaa tccatttgaa tgtcagctca acacagcctc      9120
ctataccgag gcattgtgaa ccgcatctcc ccagcttctc caggcttttc caagaatcag      9180
ggacactgta gcctgttggt ctcagtgtat gacagacacg gaggaagcac atctttagct      9240
gatacttaaa cagagaccct gagcgcacat acccgcgc acacatgcat ggagcttcac      9300
cttctctgtc attctgcagt gaccaggaga gcaagagctc ccacctcctt tcaaaacact      9360
gtgcccatcc cgggcactaa ggcctctttta aagcacggca cctccacgag ggagggccac      9420
```

```
agccacatac actccacctg gcaggtggac agcgtgagca cgtggaccat agcagggaca    9480
aggtgccccg gccagcccca acgccctctg ccgctgacag ggacagaagc cctctccagc    9540
tgcgtgtgct gcagaggcca tgcgtagcct ccagctgcat tctattccac tccagtgcct    9600
gggccagtta gcaccagtgt ggaagacagt gagctggctc cggacaacag ggatggagga    9660
aaggtcccac attcacattc ctgatacgtg gacaaggtga ggggccgcaa tcgctctggc    9720
agcattttaa agatggggaa gtagcagaca cccacgcgtg aaggcaggag agccccaact    9780
gtggtggaaa tggccccaga atggtagggc caagcctagc tccagacacc ccagagccct    9840
ggagaagcca agactgaggg agaaagcctg agggaggagc gccccagtcc caggggaccg    9900
gcctggtgca gagctgcagc tgatgttccc ctctgtgcag ccccacccta tgcctcgctg    9960
agctccctgc tgcgagggcc tcgggtgcaa ggggagggca ggtctctatc tcatggagct   10020
gtcagatgag acatcgcgat cggagtcctc agcctcgctt ggcggcggcg gcgggtcgct   10080
aagcgggacc gcagtgaaag caggagactt tctagaaaaa aacaccagtt gtcaaccttg   10140
gggcaggcag gaatcctgaa gacggacggc actcctcctc ctgctgcctc accctctggc   10200
agcccgtgag aagtaccgga agcgagggcg gggccgcggg atggcgaggg agcggcaggg   10260
actgaactct ctccaaaccc accctgacag ggaaatgggc cccgcctgtg tcttgggaac   10320
tcagaggctg aggtcaggca tgatggctca cgcctgtaat cccagcactt gggaggcag   10380 aggcgggtgg atcacgacgt caggagttca aggcaagcct ggccaacatg gtgaaacccc   10440
atctctacta aaaatgcaaa aattagccag gtgtggtggc gggcgccttg gaggctgagg   10500
caagataatc acttgaacct gggaggcgga ggttgtagtg agccaaaaaa aaaaaaaaa   10560 gaaatagctg aagtcacagt aggagagaag ctgctgagcc tccagcaccc tgactctagg   10620
gccttggctt tatgtctatc tgcagtattt ttgtgatttt taaaaattca ctttcttgtt   10680
gcggtgtaac ttacacaggg tcaaatgcac aaatcatggc cctgactta gataaaaatc   10740 tgcccccaca acccttctgt tccttgccag ttttaaact gcctctaacc aggggaacca   10800
ccagagctgg tggccttggg aggtttcagc cctcccgtca tgaatggaca tagctcatcc   10860
aactgccaag ggagagagct gtgggtctgg gccagcccca ccaggtaact cccaaagggc   10920
agccccacag caagatgtga cccagtcatt gcctgagggt ctctgggct gtgttccaac   10980 ctttctcccc gctgtgtccc cctggaaggc cccatgccca ggggaggcgc ctaccggtct   11040
ccagactggg tgatgagccg gcggcaggtc tccatctgca cgtccaggcc gcgcttcatg   11100
ctgcacatct ccatgtactc gtgcaggtgc cggttcatgt cgttcttggc cgtgccaac   11160 tccagctgtg gtggggcagg cagggccatc ggggttaaca ggtggcgttc acagcgcctc   11220
tgttgccccc gccaggaggc caacacgcca agagcagtgg ctgggccggg gcccaggca   11280 gccattactg aaggctcaga ttttaaaata aaccagacca aggcagaagg cagcgaatac   11340
accattgttt cctctgcttt tcctggaaat ctttgcctat ggaggaatgc aaaggtactg   11400
ctgcaggctg tgttctttta agactgataa gagtggtgag gaaagtcagt gtgggcggga   11460
tggagcagat ccacaggctc ccagggccac acaggttcct atggggcccg gctcacccct   11520
catcccctgt actgcgctgg tcctgggctg tccctcact gcactgtgag ctcccgtaag   11580
ggttagcgac aggttttcct catcctggca gacccagacc tcgaagggaa ttaactctct   11640
ctgtgacccg tggcatacaa gcctggctaa ctgctgaaag gggcccaatc ctcttaccat   11700
tctctcctta tcactttatt ttctcaccta aaagccattt tcagacacta aaaggaagac   11760
tcccatattg gaggtgccat tgattctgag acctgtcctg atttcagaaa tgtcacacgt   11820
```

| | | | | |
|---|---|---|---|---|
| ggaaaacacg | gggctcagaa | tcaaagaaat | ccggtctccc | tccccgggcc cattctgcag | 11880 |
| cccacactct | gaggcaggcg | gagaggcagg | gcccaggcag | cacaaactca gtgccaggga | 11940 |
| cagtcgatta | attaagcgat | cgcaggccgc | ccgcggtgga | gctccaattc gccctatagt | 12000 |
| gagtcgtatt | acgcgcgctc | actggccgtc | gttttacaac | gtcgtgactg ggaaaaccct | 12060 |
| ggcgttaccc | aacttaatcg | ccttgcagca | catcccccctt | tcgccagctg gcgtaatagc | 12120 |
| gaagaggccc | gcaccgatcg | cccttcccaa | cagttgcgca | gcctgaatgg cgaatggaaa | 12180 |
| ttgtaagcgt | taatattttg | ttaaaattcg | cgttaaattt | ttgttaaatc agctcatttt | 12240 |
| ttaaccaata | ggccgaaatc | ggcaaaatcc | cttataaatc | aaagaatag accgagatag | 12300 |
| ggttgagtgt | tgttccagtt | tggaacaaga | gtccactatt | aaagaacgtg gactccaacg | 12360 |
| tcaaagggcg | aaaaaccgtc | tatcagggcg | atggcccact | acgtgaacca tcacctaat | 12420 |
| caagtttttt | ggggtcgagg | tgccgtaaag | cactaaatcg | gaaccctaaa gggagccccc | 12480 |
| gatttagagc | ttgacgggga | aagccggcga | acgtggcgag | aaaggaaggg aagaaagcga | 12540 |
| aaggagcggg | cgctagggcg | ctggcaagtg | tagcggtcac | gctgcgcgta accaccacac | 12600 |
| ccgccgcgct | taatgcgccg | ctacagggcg | cgtcag | | 12636 |

<210> SEQ ID NO 9
<211> LENGTH: 3418
<212> TYPE: DNA
<213> ORGANISM: Artificial Sequence
<220> FEATURE:
<223> OTHER INFORMATION: 5' nucleic acid and an operably linked translation interruption-reinitiation signal

<400> SEQUENCE: 9

| | | | | |
|---|---|---|---|---|
| gggaaggtga | aggtcggagt | caacgggtga | gttcgcgggt | ggctgggggg ccctgggctg | 60 |
| cgaccgcccc | cgaaccgcgt | ctacgagcct | tgcgggctcc | gggtctttgc agtcgtatgg | 120 |
| gggcagggta | gctgttcccc | gcaaggagag | ctcaaggtca | gcgctcggac ctggcggagc | 180 |
| cccgcaccca | ggctgtggcg | ccctgtgcag | ctccgccctt | gcggcgccat ctgcccggag | 240 |
| cctccttccc | ctagtcccca | gaaacaggag | gtccctactc | ccgcccgaga tcccgacccg | 300 |
| gaccccctagg | tggggggacgc | tttctttcct | ttcgcgctct | gcggggtcac gtgtcgcaga | 360 |
| ggagcccctc | cccacggcc | tccggcaccg | caggccccgg | gatgctagtg cgcagcgggt | 420 |
| gcatccctgt | ccggatgctg | cgcctgcggt | agagcggccg | ccatgttgca accgggaagg | 480 |
| aaatgaatgg | gcagccgtta | ggaaagcctg | ccggtgacta | accctgcgct cctgcctcga | 540 |
| tgggtggagt | cgcgtgtggc | ggggaagtca | ggtggagcga | ggctagctgg cccgatttct | 600 |
| cctccgggtg | atgcttttcc | tagattattc | tctggtaaat | caaagaagtg ggtttatgga | 660 |
| ggtcctcttg | tgtcccctcc | ccgcagaggt | gtggtggctg | tggcatggtg ccaagccggg | 720 |
| agaagctgag | tcatgggtag | ttggaaaagg | acatttccac | cgcaaaatgg cccctctggt | 780 |
| ggtggcccct | tcctgcagcg | ccggctcacc | tcacggcccc | gccctttcccc tgccagccta | 840 |
| gcgttgaccc | gaccccaaag | gccaggctgt | aaatgtcacc | gggaggattg ggtgtctggg | 900 |
| cgcctcgggg | aacctgccct | tctccccatt | ccgtcttccg | gaaaccagat ctcccaccgc | 960 |
| accctggtct | gaggttaaat | atagctgctg | acctttctgt | agctggggc ctgggctggg | 1020 |
| gctctctccc | atcccttctc | cccacacaca | tgcacttacc | tgtgctccca ctcctgattt | 1080 |

```
ctggaaaaga gctaggaagg acaggcaact tggcaaatca aagccctggg actaggggt     1140
taaaatacag cttcccctct tcccacccgc cccagtctct gtcccttttg taggagggac    1200
ttagagaagg ggtgggcttg ccctgtccag ttaatttctg acctttactc ctgcccttg     1260
agtttgatga tgctgagtgt acaagcgttt tctccctaaa gggtgcagct gagctaggca    1320
gcagcaagca ttcctggggt ggcatagtgg ggtggtgaat accatgtaca aagcttgtgc    1380
ccagactgtg ggtggcagtg ccccacatgg ccgcttctcc tggaagggct tcgtatgact    1440
gggggtgttg ggcagccctg gagccttcag ttgcagccat gccttaagcc aggccagcct    1500
ggcagggaag ctcaagggag ataaaattca acctcttggg ccctcctggg ggtaaggaga    1560
tgctgcattc gccctcttaa tggggaggtg gcctagggct gctcacatat tctggaggag    1620
cctcccctcc tcatgccttc ttgcctcttg tctcttagat ttggtcgtat gggcgcctg     1680
gtcaccaggg ctgcttttaa ctctggtaaa gtggatattg ttgccatcaa tgacccctc     1740
attgacctca actacatggt gagtgctaca tggtgagccc caaagctggt gtgggaggag    1800
ccacctggct gatgggcagc cccttcatac cctcacgtat tccccaggt ttacatgttc     1860
caatatgatt ccacccatgg caaattccat ggcaccgtca aggctgagaa cgggaagctt    1920
gtcatcaatg gaaatcccat caccatcttc caggagtgag tggaagacag aatggaagaa    1980
atgtgctttg gggaggcaac taggatggtg tggctcccct gggtatatgg taaccttgtg    2040
tccctcaata tggtcctgtc cccatctccc ccccacccc ataggcgaga tccctccaaa     2100
atcaagtggg gcgatgctgg cgctgagtac gtcgtggagt ccactggcgt cttcaccacc    2160
atggagaagg ctggggtgag tgcaggaggg cccgcgggag gggaagctga ctcagccctg    2220
caaaggcagg acccgggttc ataactgtct gcttctctgc tgtaggctca tttgcagggg    2280
ggagccaaaa gggtcatcat ctctgccccc tctgctgatg cccccatgtt cgtcatgggt    2340
gtgaaccatg agaagtatga caacagcctc aagatcatca ggtgaggaag cagggcccg     2400
tggagaagcg gccagcctgg caccctatgg acacgctccc ctgacttgcg ccccgctccc    2460
tctttctttg cagcaatgcc tcctgcacca ccaactgctt agcacccctg gccaaggtca    2520
tccatgacaa ctttggtatc gtggaaggac tcatggtatg agagctgggg aatgggactg    2580
aggctcccac ctttctcatc caagactggc tcctccctgc cggggctgcg tgcaacctg     2640
gggttggggg ttctggggac tggctttccc ataatttcct ttcaaggtgg ggagggaggt    2700
agaggggtga tgtggggagt acgctgcagg gcctcactcc ttttgcagac cacagtccat    2760
gccatcactg ccacccagaa gactgtggat ggcccctccg ggaaactgtg gcgtgatggc    2820
cgcggggctc tccagaacat catccctgcc tctactggcg ctgccaaggc tgtgggcaag    2880
gtcatccctg agctgaacgg gaagctcact ggcatggcct tccgtgtccc cactgccaac    2940
gtgtcagtgg tggacctgac ctgccgtcta gaaaaacctg ccaaatatga tgacatcaag    3000
aaggtggtga gcaggcgtc ggagggcccc ctcaagggca tcctgggcta cactgagcac    3060
caggtggtct cctctgactt caacagcgac acccactcct ccacctttga cgctggggct    3120
ggcattgccc tcaacgacca ctttgtcaag ctcattcct ggtatgtggc tggggccaga    3180
gactggctct taaaaagtgc agggtctggc gccctctggt ggctggctca gaaaagggc     3240
cctgacaact cttttcatct tctaggtatg acaacgaatt tggctacagc aacagggtgg    3300
tggacctcat ggcccacatg gcctccaagg agggaatggc gcgtgcggc gggtccggag     3360
gagagggcag aggaagtctt ctaacatgcg gtgacgtgga ggagaatcct ggcccaat      3418
```

VECTORS AND METHODS FOR TARGETED INTEGRATION IN LOCI COMPRISING CONSTITUTIVELY EXPRESSED GENES

FIELD

The present invention relates to the field of genome engineering, and particularly to vectors for targeted integration into the genome, as well as products comprising such vectors and methods of using such vectors or cells derived therefrom.

BACKGROUND

A major area of interest in genome biology is targeted integration of one or more sequences of interest into desired locations. Attempts have been made to alter genomic sequences in cultured cells by taking advantage of the natural phenomenon of homologous recombination.

If a polynucleotide has sufficient homology to the genomic region comprising the sequence to be altered, it is possible for part or all of the sequence of the polynucleotide to replace the genomic sequence by homologous recombination.

However, the frequency of homologous recombination under these circumstances is extremely low. Moreover, the frequency of insertion of the exogenous polynucleotide at genomic locations that lack sequence homology exceeds the frequency of targeted homologous recombination by several orders of magnitude.

The introduction of a double-stranded break into genomic DNA, in the region of the genome bearing homology to an exogenous polynucleotide, has been shown to stimulate homologous recombination at this site in cultured cells.

However, the question of where to introduce new genes remains problematic. For some purposes, it is commonly thought that integration should be targeted to genes that are thought to be dispensable or to extragenic regions.

Genomic safe harbours (GSHs) are intragenic or extragenic regions of the human genome that are able to accommodate the predictable expression of newly integrated DNA without adverse effects on the host cell or organism. A useful safe harbour must permit sufficient transgene expression to yield desired levels of the vector-encoded protein or non-coding RNA. A GSH also must not predispose cells to malignant transformation nor alter cellular functions.

Only three sites in the human genome have been used for targeted transgene addition to date: the adeno-associated virus site 1 (AAVS1), the chemokine (CC motif) receptor 5 (CCR5) gene locus, and the human orthologue of the mouse ROSA26 locus. At present, the information that is currently available regarding the safety features of these loci is too limited to qualify any of them as a GSH.

However, there remain needs for compositions and methods for stable targeted integration into a locus within the genome that provides constitutive expression.

SUMMARY

In a first aspect, the invention provides a vector comprising:
  a 5' nucleic acid that is homologous to a genomic sequence 5' of a genomic stop codon of a constitutively expressed gene;
  an exogenous nucleic acid;
  a 3' nucleic acid that is homologous to a genomic sequence 3' of the genomic stop codon of the constitutively expressed gene;
  a translation interruption-reinitiation signal operably linked to the 5' nucleic acid and the exogenous nucleic acid,
wherein the translation interruption-reinitiation signal is capable of replacing the genomic stop codon of the constitutively expressed gene.

In one embodiment of the vector of the first aspect, the constitutively expressed gene comprises GAPDH, ACTB, HSP90, B2M, HPRT1, RPLP1, GUSB, LDHA, NONO, PGK1, PPIH, RPLP0, or TFRC.

In a second aspect, the invention provides a cell comprising the vector of the first aspect.

In a third aspect, the invention provides a non-human animal comprising the vector of the first aspect, or the cell of the second aspect.

In a fourth aspect, the invention provides a method for expressing an exogenous nucleic acid in a cell, the method comprising cleaving genomic DNA comprising a constitutively expressed gene in the cell to produce a double stranded break in the genomic DNA, incorporating into the cell the vector of the first aspect, and replacing the constitutively expressed gene's stop codon with the translation interruption-reinitiation signal.

In a fifth aspect, the invention provides a cell when obtained by the method of the fourth aspect.

In a sixth aspect, the invention provides a non-human animal comprising the cell of the fifth aspect.

In a seventh aspect, the invention provides a method for identifying a cell in a population of cells or a tissue, the method comprising cleaving in a cell genomic DNA comprising a constitutively expressed gene to produce a double stranded break in the genomic DNA, incorporating into the cell the vector of the first aspect, replacing the constitutively expressed gene's stop codon with the translation interruption-reinitiation signal, and detecting expression of the exogenous nucleic acid in the cell.

It is commonly thought that constitutively expressed genes (sometimes referred to as housekeeping genes) may be attractive as potential universal GSHs because of their ubiquitous expression, but this very property argues against dispensability and therefore their capacity as GSHs.

The present invention overcomes this prejudice and demonstrates that a constitutively expressed gene is a valuable locus for expression of an exogenous nucleic acid.

BRIEF DESCRIPTION OF THE DRAWINGS

Embodiments of the invention will now be described by way of example only with reference to the accompanying drawings in which:

FIG. 3 is a schematic of hematopoietic (mesodermal) differentiation according to Example 4. Key time points are indicated: Day 0 marks the beginning of the suspension EB stage. At day 4, a media change occurs including the key blood cell growth factors indicated. At day 7, EBs are plated down with additional growth factors to allow adherent cells to expand. Growth factors are shown in the top row with their respective concentrations shown underneath in ng/ml (except for Epo, in U/ml). StemDiff APEL was used as the base medium for all stages.

FIG. 7 provides fluorescent photomicrographs demonstrating the origin of cystic colonies in MCM colony forming assay according to Example 5. A. A typical 'mixed colony', with corresponding bright field, GFP and mCherry micrographs on the left. B. Field view of colonies showing the proximity of differently coloured colonies and a mixed colony. Corresponding bright field, GFP and mCherry micrographs are below. Mixed colonies were in general much larger than single coloured colonies. All scale bars 500 μm.

FIG. 8 provides a column graph, flow cytometry plot, and tabulated data of the analysis of colony composition in H9 GT-GFP/GT-mCherry MCM cultures according to Example 5. A. Column graph of raw scoring data. 'Trace green' colonies are grouped with the red colonies and outlined in green. 'Trace red' colonies are grouped with the green colonies and outlined in red. B. Flow cytometry data for day 18 MCM colonies with percentages of GFPP$^{pos}$ and mCherry$^{pos}$ populations indicated. C. Table of colony scoring data as percentage of total red and total green cells.

FIG. 9 shows the structure of the GT-iCherry vector according to Example 6. This embodiment of the vector is based on the same vector used in the GT-GFP and GT-mCherry lines. This vector includes an rTA that codes for a transcriptional activator protein required for expression of the transgene located 3' of the TetO (Tet operator) promoter. In the presence of doxycycline (Dox), the rTA protein binds to and activates transcription from TetO. Hence, expression of the reporter Gene is inducible. In this set of experiments, the reporter gene used in the inducible variant is mCherry. I indicates an IRES, and S indicates the position of the selectable marker (in this case neomycin).

FIG. 13 provides a schematic of the experimental protocol and photomicrographs related to the effects of 4OHT on the morphology of differentiated cells derived from GT-MYC: ER hESCs according to Example 8. A. Schematic of the differentiation protocol. Concentrations of growth factors used are shown in ng/ml. Base medium is indicated on the bottom row of each stage. B. Bright field images of differentiated day 12 GT-MYC: ER cells in the presence or absence of 4OHT. Scale bar 100 μm; applies for all images.

FIG. 14 provides a schematic of the experimental protocol and photomicrographs related to the GT-MYC:ER colony forming assay according to Example 9. A. Schematic of the differentiation protocol used to generate hematopoietic and endothelial precursor cells. Concentrations of growth factors used are shown in ng/ml, except for EPO—shown in U/ml. Base medium is indicated on the bottom row of each stage. B-F. Bright field images displaying examples of each category used in day 21 scoring of MCM colonies. B. Red arrow indicates a typical erythroid colony, while the black arrow indicates a cystic colony. C. Developing cystic colony. D. Myeloid colony. E-F. Two types of 'adherent sheet' colonies. All scale bars 100 μm.

FIG. 17 provides a nucleic acid sequence of a translation interruption-reinitiation signal (SEQ ID NO: 1).

FIG. 18 provides a nucleic acid sequence of a 5' nucleic acid (SEQ ID NO: 2).

FIG. 19 provides a nucleic acid sequence of a 3' nucleic acid (SEQ ID NO: 3).

FIG. 20 provides a nucleic acid sequence of an internal ribosomal entry site (SEQ ID NO: 4).

FIG. 21 provides a nucleic acid sequence of the vector GT-GFP (SEQ ID NO: 5).

FIG. 22 provides a nucleic acid sequence of the vector GT-mCherry (SEQ ID NO: 6).

FIG. 23 provides a nucleic acid sequence of the vector GT-MYC:ER (SEQ ID NO: 7).

FIG. 24 provides a nucleic acid sequence of the vector GT-iCherry (SEQ ID NO: 8).

FIG. 25 provides a nucleic acid sequence comprising a 5' nucleic acid and an operably linked translation interruption-reinitiation signal (SEQ ID NO: 9).

DETAILED DESCRIPTION

Vector

Figure 1:
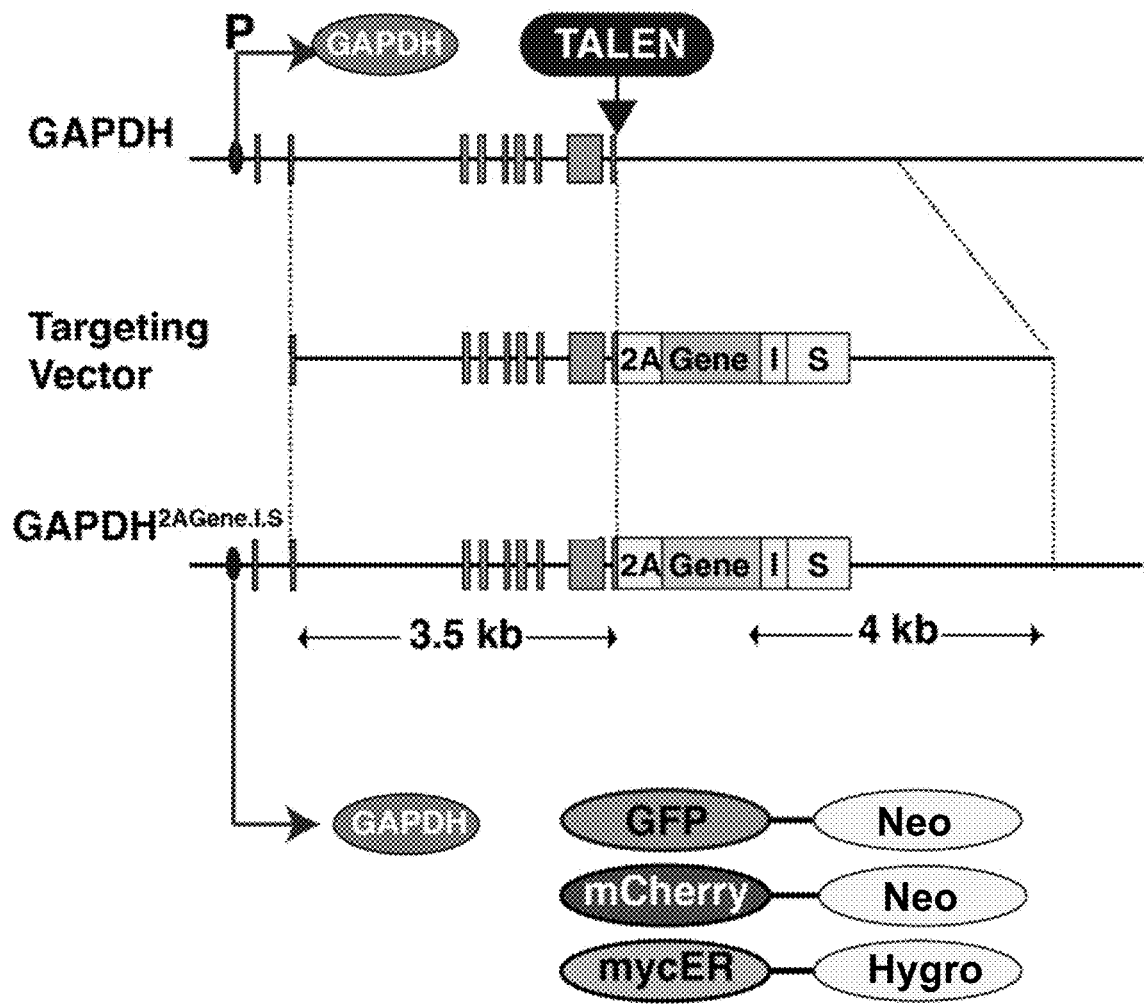
FIG. 1 is a schematic showing the structure of the GAPDH locus (top line) with exons indicated in grey, the vector (middle line), and the modified GAPDH locus following gene targeting (bottom line). The GAPDH promoter is indicated with a 'P'. The position within the locus cut by the TALENs is also indicated. This embodiment of the vector comprises a 3.5 kb homology arm, a T2A (2A) segment that replaces the stop codon of endogenous GAPDH. Amino acids of the T2A segment provide a link that joins the carboxyl end of the GAPDH protein, to the amino terminus of protein encoded by the downstream endogenous nucleic acid (Gene). The T2A sequence within the mRNA results in a translational skip enabling Gene to be expressed from the same RNA, but as a separate protein (that is, not as a fusion protein). This means that the modified locus produces GAPDH protein extended by 21 amino acids of the T2A peptide as well as the protein encoded by the downstream Gene. Genes expressed from this T2A sequence are indicated (GFP, mCherry, MYC:ER). Following the gene of interest in this embodiment is an Internal Ribosomal Entry Site (designated I) that re-recruits ribosomes to continue translation, once they have dissociated from the mRNA after completing translation of the upstream Gene. This allows for the translation of S, a selectable marker encoding antibiotic-resistance fused to the protein encoded by Gene. Genes specifying neomycin (Neo) and hygromycin (Hygro) resistance are indicated. 3' of the selectable marker is the 3' homology arm which, together with the 5' homology arm, mediates homologous recombination into GAPDH.

The present invention provides a vector comprising one or more exogenous nucleic acids for expressing one or more products of an exogenous nucleic acid (i.e. a protein or a RNA molecule) that has been integrated into a constitutively expressed gene in a cell.

Constitutively expressed genes are generally thought to be essential for cell viability. Therefore, although expressed in most cells, constitutively expressed genes also are generally considered unsuitable for genetic targeting owing to the possibility of unintentional adverse consequences of targeted integration.

Contrary to this prejudice, the present invention shows that constitutively expressed genes may be modified to enable constitutive expression of an exogenous nucleic acid, while maintaining endogenous expression of the constitutively expressed gene.

The invention is achieved by replacing the genomic stop codon of the constitutively expressed gene with an in-frame translation interruption-reinitiation signal that operably links the constitutively expressed gene with the exogenous nucleic acid.

Importantly, the product of the exogenous nucleic acid is expressed as a separate protein to the product of the constitutively expressed gene; i.e. the product is not a fusion protein.

Accordingly, any exogenous nucleic acid may be introduced into the constitutively expressed gene as described herein, provided that the exogenous nucleic acid operably linked to the translation interruption-reinitiation signal encodes a protein. Exogenous nucleic acids can range in length from 10 to 5,000 nucleotides (or any integral value of nucleotides between) or longer.

Exemplary exogenous nucleic acids include, but are not limited to, any polypeptide coding sequence (e.g., cDNAs), promoter or other regulatory sequences, RNA molecule (e.g., small hairpin RNAs (shRNA), inhibitory RNAs (RNAi), microRNAs (miRNA), etc.), epitope tags, marker genes, cleavage enzyme recognition sites, various types of expression constructs, internal ribosome entry sites, and/or polyadenylation signals. The exogenous nucleic acid is introduced into the cell such that it is integrated into the genome of the cell in a constitutively expressed gene. Expression of the integrated sequence is then ensured by transcription driven by the endogenous promoter of the constitutively expressed gene. Such sequences can be readily obtained using standard molecular biological techniques (cloning, synthesis, etc.) and/or are commercially available.

In certain embodiments, the exogenous nucleic acid comprises a promoterless sequence encoding an antibody, an antigen, an enzyme, a growth factor, a receptor (cell surface or nuclear), a hormone, a lymphokine, a cytokine, a reporter, a functional fragment of any of the above, or a combination of any of the above.

In other embodiments, a "tandem" cassette is integrated into the constitutively expressed gene in this manner, the first component of the cassette comprising a promoterless sequence as described above, followed by a transcription termination sequence, and a second sequence, encoding an autonomous expression cassette.

In certain embodiments, the exogenous nucleic acids can comprise a marker gene allowing identification, tracking and selection of cells that have undergone targeted integration.

Marker genes include, but are not limited to, sequences encoding proteins that mediate antibiotic resistance (e.g., neomycin resistance (Neo), G418 resistance (Neo), puromycin resistance, hygromycin resistance (Hygro)), sequences encoding coloured or fluorescent or luminescent proteins (e.g., mCherry, green fluorescent protein, enhanced green fluorescent protein, red fluorescent protein, luciferase), cell surface antigens (e.g., ΔNGFR), and proteins, including fusion proteins, that mediate enhanced cell growth and/or gene amplification (e.g., MYC, KRAS, dihydrofolate reductase). Epitope tags include, for example, one or more copies of FLAG, His, myc, Tap, HA or any detectable amino acid sequence.

In some embodiments, the marker gene comprises a sequence encoding GFP or mCherry.

Additional marker genes include sequences that encode coloured or fluorescent proteins such as: blue/UV proteins, e.g. TagBFP, mTagBFP2, Azurite, EBFP2, mKalamal, Sirius, Sapphire, T-Sapphire; cyan proteins, e.g. ECFP, Cerulean, SCFP3A, mTurquoise, mTurquoise2, monomeric Midoriishi-Cyan, TagCFP, mTFP1; green proteins, e.g. EGFP, Emerald, Superfolder GFP, Monomeric Azami Green, TagGFP2, mUKG, mWasabi, Clover, mNeonGreen; yellow proteins, e.g. EYFP, Citrine, Venus, SYFP2, TagYFP; orange proteins, e.g. Monomeric Kusabira-Orange, mKOκ, mKO2, mOrange, mOrange2; red proteins, e.g. mRaspberry, mStrawberry, mTangerine, tdTomato, TagRFP, TagRFP-T, mApple, mRuby, mRuby2; far-red proteins, e.g. mPlum, HcRed-Tandem, mKate2, mNeptune, NirFP; near-IR proteins, e.g. TagRFP657, IFP1.4, iRFP; long stokes shift proteins, e.g. mKeima Red, LSS-mKate1, LSS-mKate2, mBeRFP; photoactivatible proteins, e.g. PA-GFP, PAmCherry1, PATagRFP; photoconvertible proteins, e.g. Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange; and photoswitchable proteins, e.g. Dronpa.

The vector may also encode one or more cleavage proteins.

The vector comprising the exogenous nucleic acid can be introduced into the cell prior to, concurrently with, or subsequent to, expression of a cleavage protein. The vector comprising the exogenous nucleic acid comprises sufficient homology to the genomic sequence of the constitutively expressed gene to support homologous recombination. About 20, 25, 30, 35, 40, 45, 50, 55, 60, 65, 70, 75, 80, 85, 90, 95, 100, 150, 200, 250, 300, 350, 400, 450, 500, 600, 700, 750, 800, 900, or 1,000 bases, or 1.5, 2.0, 2.5, 3.0, 3.5, 4.0, 4.5, 5.0, 5.5, 6.0, 6.5, 7.0, 7.5, 8.0, 8.5, 9.0, 9.5 or 10 kb or more of sequence homology (or any integral value between 10 and 10,000 nucleotides, or more) will support homologous recombination.

Generally, the homologous region(s) of a vector comprising an exogenous nucleic acid will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the vector comprising the exogenous nucleic acid. Preferably, the sequence identity will be sufficiently high to maintain endogenous expression and activity of the constitutively expressed gene and its product. Accordingly, sequence identity in coding regions of the constitutively expressed gene may be 95%, 96%, 97%, 98%, 99% or 100%. When calculating sequence identity, the genomic stop codon of the constitutively expressed gene may be excluded.

The vector may comprise a non-homologous sequence flanked by two regions of homology in turn flanking the one or more exogenous nucleic acids. The vector may comprise additional sequences such as, for example, replication origins, promoters and genes encoding antibiotic resistance.

The vector may comprise several, discontinuous regions of homology to genomic sequence. For example, regions of homology can flank two or more regions comprising the exogenous nucleic acid.

It will be readily apparent that the homologous region is not necessarily identical to the genomic sequence that it replaces. For example, the sequence of the vector comprising the exogenous nucleic acid can comprise one or more single base changes, insertions, deletions, inversions or rearrangements with respect to the genomic sequence, so long as sufficient homology with the genomic sequence is present to allow homologous recombination and to maintain endogenous expression and activity of the constitutively expressed gene and its product.

The vector comprising the exogenous nucleic acid can be DNA or RNA, single-stranded or double-stranded and can be introduced into a cell in linear or circular form. If introduced in linear form, the ends of the exogenous nucleic acid can be protected (e.g., from exonucleolytic degradation) by methods known to those of skill in the art. Moreover, vector comprising the exogenous nucleic acids can be introduced as naked nucleic acid, as nucleic acid complexed with an agent such as a liposome or poloxamer, or can be delivered by viruses (e.g., adenovirus, AAV, herpesvirus, retrovirus, lentivirus).

Vectors can be prokaryotic vectors, e.g., plasmids, or shuttle vectors, insect vectors, or eukaryotic vectors. In certain embodiments, the vector is a plasmid. In other embodiments, the vector is a linear DNA molecule.

Targeted integration of exogenous nucleic acids, as disclosed herein, can be used to generate cells and cell lines for protein expression.

The vector may be chemically synthesised. Alternatively, the vector may be produced using standard recombinant engineering techniques. Such recombinant engineering techniques may use bacterial artificial chromosomes (BACs) spanning the constitutively expressed gene locus together with insertion of the translation interruption-reinitiation signal and the exogenous nucleic acid.

Constitutively Expressed Genes

The constitutively expressed gene may comprise GAPDH (glyceraldehyde-6-phosphate dehydrogenase), ACTB (actin, beta), HSP90AB1 (heat shock protein HSP 90-beta), B2M (beta-2-microglobulin), HPRT1 (hypoxanthine phosphoribosyltransferase 1), RPLP1 (ribosomal protein, large, P1), GUSB (glucuronidase, beta), LDHA (lactate dehydrogenase A), NONO (non-POU domain containing, octamer-binding), PGK1 (phosphoglycerate kinase 1), PPIH (peptidylprolyl isomerase H), RPLP0 (ribosomal protein, large, P0), or TFRC (transferrin receptor).

Other constitutively expressed genes will be known to the person skilled in the art.

Targeted Integration into GAPDH

GAPDH is a key enzyme involved in glycolysis, the process by which glucose is metabolised to produce energy in the form of ATP, fundamental to the viability and function of cells within multicellular organisms. The GAPDH gene is widely recognised as being expressed at relatively high levels in most cell types. It has been shown to be expressed in embryonic stem cells and the great majority of adult tissue types, with little variation in expression levels relative to the age of the tissue or gender of origin. For this reason, GAPDH mRNA levels are often used as a reference to normalise or standardize the expression of genes of interest when conducting gene expression analyses. GAPDH lies on human chromosome 12 and mouse chromosome 6.

For targeted integration into GAPDH, one or more binding domains may be engineered to bind a target site at or near the predetermined cleavage site, and a cleavage protein comprising the engineered binding domain and a cleavage domain is introduced into or expressed in a cell. Upon binding of the cleavage protein to the target site, the DNA is cleaved, preferably via a double stranded break, near the target site by the cleavage domain.

The presence of a double-stranded break in genomic DNA facilitates integration of exogenous nucleic acids via homologous recombination. Thus, the vector comprising the exogenous nucleic acids to be inserted into GAPDH will include one or more regions of homology with GAPDH to facilitate homologous recombination.

GAPDH delivered ubiquitous and consistent expression of transgenes and other genetic elements (see examples). Disclosed herein is a targeting vector that inserted exogenous nucleic acid into the 3' UTR of the GAPDH locus. Because GAPDH is critical to cell viability, it was important that the impact of the modification on the expression or function of GAPDH was minimized. As such, the GAPDH targeting vector inserted exogenous nucleic acids into the GAPDH locus while maintaining GAPDH protein expression from the modified GAPDH allele.

In order to achieve this outcome, TALENs were used to cut the endogenous GAPDH locus at the point immediately 3' of the GAPDH stop codon. This double stranded break is repaired by using the GAPDH targeting vector disclosed herein. The utility of the vector is enhanced by the vector "trapping" the GAPDH promoter, and replacing the GAPDH genomic stop codon with the translation interruption-reinitiation signal.

Translation Interruption-Reinitiation Signal

The translation interruption-reinitiation signal may be a 2A or 2A-like peptide sequence that separates different protein coding sequences in a single ORF transcription unit of Picornaviridae. The 2A peptide sequences from different members of the picornavirus family share a highly conserved motif of only 18 amino acids. Most 2A peptides are 18-22 amino acids. The 2A peptide is responsible for a ribosomal-skip mechanism Linking the constitutively expressed gene and the exogenous nucleic acid with 2A peptide or 2A-like peptide results in cellular expression of multiple, discrete proteins in essentially equimolar quantities derived from a single open reading frame.

Examples of 2A peptide that may be encoded by the vector include porcine teschovirus-1 2A (P2A), Thoseaasigna virus 2A (T2A), equine rhinitis A virus (E2A), and foot-and-mouth disease virus (FMDV) (F2A).

The 2A signal may encode a peptide of 15, 16, 17, 18, 19, 20, 21, 22, 23, 24, 25, 26, 27, 28, 29, or 30 amino acids, for example.

Cells

The target cell can be a mammalian cell, for example, a human cell or a mouse cell. The cell may be a pluripotent stem cell (PSC), an embryonic stem cell, an induced pluripotent stem cell, or a cell differentiated from a pluripotent stem cell, an embryonic stem cell, or an induced pluripotent stem cell.

Embryonic stem cells include H9 human embryonic stem cells and MEL1 human embryonic stem cells.

Furthermore, the cell may be arrested in the G2 phase of the cell cycle.

When using genetic modification to study the function of a specific gene, it is desirable that the consequences of the modification are manifested in the cell types in which that gene is normally expressed. This can be achieved by either targeting the modification to a gene that is known to be expressed in a cell type specific fashion, or by taking advantage of a locus that is active in all or most cell types. The advantage of the latter is that analysis of gene function in a specific cell type simply requires that this cell type can be identified in a mixed culture of differentiated cells. Often, this identification is based on cell surface marker expression, enabling the cell of interest to be isolated by flow cytometry. Furthermore, by using a constitutively expressed locus as a platform for expression, analysis probing the function of the transgene is not restricted to any particular lineage. Accordingly, disclosed herein is a method of identifying a cell, the method comprising detecting expression of the exogenous nucleic acid.

In one embodiment, identifying may comprise cell imaging. In another embodiment, identifying may comprise cell sorting, enzymatic assay, ligand binding, or receptor binding, for example.

Also disclosed is a method of drug screening, the method comprising contacting a cell expressing a gene product from the exogenous nucleic acid integrated into the constitutively expressed gene with a candidate drug and detecting an effect of the candidate drug on the cell.

Cell Cycle

Increases in efficiency of targeted recombination may be achieved by blocking the cells in the G2 phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in G2 phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cis-platin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the cyclin and/or CDK cell-cycle kinases, for example, by introducing a cDNA encoding the inhibitory protein into the cell or by using RNAi methods.

Double Stranded Cleavage

Integration of the exogenous nucleic acid into the constitutively expressed gene is assisted by targeted double-strand cleavage of the genomic constitutively expressed gene.

Various methods and compositions for targeted cleavage of genomic DNA have been described. Such targeted cleavage events can be used, for example, to induce targeted mutagenesis, induce targeted deletions of cellular DNA sequences, and as disclosed herein, facilitate targeted recombination at a predetermined chromosomal locus.

Several methodologies to induce site-specific double stranded breaks in the targeted site are now available, including transcription activator-like effector (TALE) nucleases (TALENs), meganucleases, zinc-finger nucleases, and clustered regularly interspaced short palindromic repeats (CRISPRs).

Definitions

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, a "vector" is a nucleic acid used as a vehicle to carry foreign genetic material, i.e. the exogenous nucleic acid, into another cell, where it can be expressed. According to the invention, expression of the exogenous nucleic is driven by the promoter of the constitutively expressed gene to with the exogenous nucleic acid is operably linked. The four major types of vectors are plasmids, viral vectors, cosmids, and artificial chromosomes.

As used herein, the terms "nucleic acid" and "polynucleotide" are used interchangeably and refer to a deoxyribonucleotide or ribonucleotide polymer, in linear or circular conformation, and in either single-stranded or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

As used herein, the terms "5'" and "3'" define the directionality or end-to-end chemical orientation of a single strand of nucleic acid. 5' designates the end of the DNA or RNA strand that has the fifth carbon in the sugar-ring of the deoxyribose or ribose at its terminus. 3' designates the end of the DNA or RNA strand that has the hydroxyl group of the third carbon in the sugar-ring of the deoxyribose or ribose at its terminus. A 5' phosphate group and a 3'-hydroxyl permits ligation of two nucleotides, i.e. the covalent binding of a 5'-phosphate of one nucleotide to the 3'-hydroxyl group of another nucleotide to form a phosphodiester bond. Removal of the 5'-phosphate prevents ligation.

An "exogenous" nucleic acid is a nucleic acid derived from a source other than the cell into which it is to be recombined. The exogenous nucleic acid can be introduced into a cell by one or more genetic, biochemical or other methods. Nevertheless, the exogenous nucleic acid may be substantially similar or identical to an endogenous gene, but the exogenous nucleic acid has altered spatial or temporal expression relative to the endogenous gene owing to integration of the nucleic acid in the constitutively expressed gene.

As used herein, the term "product of an exogenous nucleic acid" includes both polynucleotide and polypeptide products, for example, transcription products (polynucleotides such as RNA) and translation products (polypeptides).

As used herein, the term "endogenous" refers to a moiety that is normally present in a cell. For present purposes, "endogenous" refers to the cellular state prior to homologous recombination using the vector of the invention.

As used herein, the terms "homology" and "homologous" refers to nucleic acids (or proteins) that are similar or identical over a given region of their sequences. Homology is often defined in terms of percent sequence identity. In the present context, homology or percent sequence identity allows binding the vector and genomic DNA in turn allowing recombination.

Techniques for determining nucleic acid and protein sequence identity are known in the art. Typically, such techniques include determining the nucleotide sequence of the cDNA or mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or protein sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981).

"Recombination" refers to a process of exchange of genetic information between two polynucleotides. For the purposes of this disclosure, "homologous recombination" refers to the specialized form of such exchange that takes place, for example, during repair of double-stranded breaks in cells.

A "gene," for the purposes of the present disclosure, includes a DNA region encoding a gene product, as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, the terms "genomic" and "genome" refer to the endogenous genetic material of an organism generally comprised in chromosomes. The genome includes both the coding (genes) and the non-coding sequences. It follows that a "genomic stop codon" is the endogenous, chromosomal stop codon, and a "genomic sequence" is the endogenous, chromosomal DNA sequence.

"Expression" refers to the conversion of genetic information into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, "constitutively expressed" refers to continuous or consistent expression. Preferably, a "constitutively expressed" gene is also ubiquitously expressed throughout differentiation and in all cell types and tissue types, for example.

As used herein, the term "translation interruption-reinitiation signal" refers to a nucleic acid sequence that encodes a peptide responsible for a ribosomal-skip mechanism. Although one ORF exists, and one mRNA is transcribed from the ORF, during translation, the ribosomal skip mechanism results in cellular expression of multiple, discrete proteins in essentially equimolar quantities expression of which is driven by the same promoter.

The term "operably linked" is used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operably linked to a coding sequence if the transcriptional regulatory sequence controls the level of transcription of the coding sequence in response to the presence or absence of one or more transcriptional regulatory factors. A transcriptional regulatory sequence is generally operably linked in cis with a coding sequence, but need not be directly adjacent to it. For example, an enhancer is a transcriptional regulatory sequence that is operatively linked to a coding sequence, even though they are not contiguous.

As used herein, the term "is capable of replacing" is used with reference to the translation interruption-reinitiation signal and the stop codon and indicates sufficiency for such replacement under the appropriate conditions. The term is not limiting and is not to be construed as requiring replacement, merely the capacity and propensity for replacement.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). A binding protein can have more than one type of binding activity.

A "binding domain" is a domain within a larger binding protein that binds DNA in a sequence-specific manner.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, cleavage polypeptides are used for targeted double-stranded DNA cleavage. The terms "double stranded break", "DSB", and "double stranded cleavage" are interchangeable and refer to cutting or breaking both the sense and anti-sense strand of a chromosome.

A "cleavage domain" comprises one or more polypeptide sequences which possesses catalytic activity for DNA cleavage. A cleavage domain can be comprised in a single polypeptide chain or cleavage activity can result from the association of two (or more) polypeptides.

A "cleavage half-domain" is a polypeptide sequence which, in conjunction with a second polypeptide (either identical or different), forms a complex having cleavage activity (preferably double-strand cleavage activity).

A cleavage protein may comprise a cleavage domain or cleavage half-domains.

A "target site" or "target sequence" is a nucleic acid sequence that defines a portion of a nucleic acid to which a binding protein will bind, provided sufficient conditions for binding exist.

To "target" or "targeted" refers to a desired or intended event at a designated location. For example, a desired or intended binding, cleavage or integration event at a specific genomic location.

As used herein, "GT-" refers to an embodiment of the vector that is dependent on the vector "trapping" the GAPDH promoter, also referred to as "GapTrap-".

Cleavage

TALENs

A TALEN is an artificial endonucleases generated by fusing a TALE DNA-binding domain to the catalytic domain of an endonuclease that introduces double-strand breaks. The DNA-binding domains are comprised of almost identical TALE repeats, which are units of approximately 34 amino acids. The TALE repeats differ by two highly variable amino acids, and this establishes the base-recognition specificity of the DNA binding domain. TALENs can be engineered to target user-specified DNA sequences within complex genomes. Pairs of TALENs work together to make a double stranded break in the DNA. The functional domain of the TALEN may be a modified version of the FokI restriction endonuclease.

Meganucleases

Meganucleases are naturally occurring, sequence-specific endonucleases with recognition sequences so large that they do not occur, or occur only rarely, in the genome of interest (>12 bp).

CRISPRs

CRISPRs are DNA loci comprising short repetitions of base sequences. Each repetition is followed by short segments of "spacer DNA" from previous exposures to a virus. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system may be used for gene editing. By delivering the Cas9 protein and appropriate guide RNAs into a cell, the organism's genome can be cut at any desired location. Free software is available to design RNA to target any desired gene.

Zinc-Finger Nucleases

Zinc-finger nucleases are a class of synthetic proteins generated by fusing a zinc-finger DNA-binding domain to the cleavage domain or cleavage half-domain of a restriction endonuclease, for example a cleavage half-domain may be from a Type IIS restriction endonuclease such as FokI or StsI. The DNA-binding domain can be engineered to induce double-stranded breaks in desired DNA sequences.

Cleavage may be targeted to the constitutively expressed gene through the use of cleavage proteins comprising a zinc finger DNA binding domain, which is engineered to bind a sequence within the constitutively expressed gene, and a cleavage domain or a cleavage half-domain. Such cleavage stimulates integration of exogenous polynucleotide sequences at or near the cleavage site.

A zinc finger binding domain can comprise one or more zinc fingers (e.g., 2, 3, 4, 5, 6, 7, 8, 9 or more zinc fingers), and can be engineered to bind to any sequence within the constitutively expressed gene.

Target Sites

Selection of a sequence in the constitutively expressed gene for binding by a zinc finger domain (a target site) can be accomplished, for example, according to the methods disclosed in U.S. Pat. No. 6,453,242, which also discloses methods for designing zinc finger proteins to bind to a selected sequence.

Target sites for zinc finger domains are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. A target site generally but not necessarily has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

One or more subsites, in a target site for a zinc finger binding domain, can be separated from each other by 1, 2, 3, 4, 5 or more nucleotides. In certain embodiments in which cleavage depends on the binding of two cleavage domain/cleavage half-domains to separate target sites, the two target sites can be on opposite DNA strands. In other embodiments, both target sites are on the same DNA strand.

It will be clear to those skilled in the art that simple visual inspection of a nucleotide sequence can also be used for selection of a target site. Accordingly, any means for target site selection can be used in the methods described herein.

DNA-Binding Domains

Any DNA-binding domain can be used in the methods disclosed herein. In certain embodiments, the DNA binding domain comprises a TALEN, CRISPR, zinc finger protein, or endogenous activity of a nuclease. A zinc finger binding domain comprises one or more zinc fingers. The zinc finger binding domains described herein generally include 2, 3, 4, 5, 6 or even more zinc fingers.

Typically, a single zinc finger domain is about 30 amino acids in length.

Alternatively, the DNA-binding domain may be derived from a nuclease. The nuclease may be a meganuclease. For example, the recognition sequences of homing endonucleases and meganucleases such as I-SceI, I-CeuI, PI-PspI, PI-Sce, I-SceIV, I-CsmI, I-PanI, I-SceII, I-Ppol, I-SceIII, I-CreI, I-TevI, I-TevII and I-TevIII are known. In addition, the DNA-binding specificity of homing endonucleases and meganucleases can be engineered to bind non-natural target sites.

Cleavage Domains

The cleavage domain can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease). Non limiting examples of homing endonucleases and meganucleases include I-SceI, I-CeuI, PI-PspI, PI-Sce, I-SceIV, I-CsmI, I-PanI, I-SceII, I-Ppol, I-SceIII, I-CreI, I-TevI, I-TevII and I-TevIII. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other strand.

An exemplary Type IIS restriction enzyme, whose cleavage domain is separable from the binding domain, is Fok I. This particular enzyme is active as a dimer. A portion of the Fok I enzyme may be considered a cleavage half-domain. Thus, for targeted double-stranded cleavage and/or targeted replacement of genomic sequences using a Fok I cleavage domain, two cleavage FokO cleavage half-domains can be used to reconstitute a catalytically active cleavage domain. Alternatively, a single polypeptide molecule comprising a binding domain and two Fok I cleavage half-domains can also be used.

Another example of Type IIS restriction enzyme is StsI.

A cleavage domain or cleavage half-domain can be any portion of a protein that retains cleavage activity, or that retains the ability to multimerize (e.g., dimerize) to form a functional cleavage domain.

To enhance cleavage specificity, cleavage domains may also be modified. In certain embodiments, variants of the cleavage half-domain are employed, which variants that minimize or prevent homodimerization of the cleavage half-domains. In certain embodiments, the cleavage domain comprises an engineered cleavage half-domain that minimizes or prevents homodimerization. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Additional engineered cleavage half-domains of Fok I that form an obligate heterodimer can also be used in the methods described herein. The first cleavage half-domain includes mutations at amino acid residues at positions 490 and 538 of Fok I and the second cleavage half-domain includes mutations at amino acid residues 486 and 499.

In certain embodiments of the method, the cleavage domain comprises two cleavage half-domains, both of which are part of a single polypeptide further comprising a binding domain. Alternatively, each cleavage half domain is part of a polypeptide further comprising a binding domain. The cleavage half-domains can have the same amino acid sequence or different amino acid sequences, so long as they function to cleave the DNA.

Target sites for the cleavage domains are preferably disposed, with respect to each other, such that binding to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Cleavage Proteins

Methods for design and construction of cleavage proteins (and their encoding polynucleotides) are known to those of skill in the art. In certain embodiments, polynucleotides encoding such cleavage proteins are constructed. These polynucleotides can be inserted into a vector and the vector can be introduced into a cell.

Expression of two cleavage proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a cleavage protein comprises a single polypeptide chain comprising two cleavage half domains and a binding domain. In this case, a single cleavage protein is expressed in a cell and, without wishing to be bound by theory, is believed to cleave DNA as a result of formation of an intramolecular dimer of the cleavage half-domains.

The components of the cleavage proteins may be arranged such that the binding domain is nearest the amino terminus of the cleavage protein, and the cleavage half-domain is nearest the carboxy-terminus. Dimerization of the cleavage half-domains to form a functional nuclease is brought about by binding of the cleavage proteins to sites on opposite DNA strands, with the 5' ends of the binding sites being proximal to each other.

Alternatively, the components of the cleavage proteins may be arranged such that the cleavage half-domain is nearest the amino terminus of the cleavage protein, and the binding domain is nearest the carboxy-terminus. In these embodiments, dimerization of the cleavage half-domains to form a functional nuclease is brought about by binding of the cleavage proteins to sites on opposite DNA strands, with the 3' ends of the binding sites being proximal to each other.

In yet additional embodiments, a first cleavage protein comprises the cleavage half-domain nearest the amino terminus of the cleavage protein, and the binding domain nearest the carboxy-terminus, and a second cleavage protein is arranged such that the binding domain is nearest the amino terminus of the cleavage protein, and the cleavage half-domain is nearest the carboxy-terminus. In these embodiments, both cleavage proteins bind to the same DNA strand, with the binding site of the first cleavage protein comprising the binding domain nearest the carboxy-terminus located to the 5' side of the binding site of the second cleavage protein comprising the binding domain nearest the amino terminus.

The two cleavage proteins can bind in the region of interest in the same or opposite polarity, and their binding sites (i.e., target sites) can be separated by any number of nucleotides, e.g., from 0 to 200 nucleotides or any integral value between. In certain embodiments, the binding sites for two cleavage proteins, each comprising a binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two cleavage proteins. Double-strand cleavage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the cleavage proteins and the distance between the target sites can influence whether cleavage occurs adjacent a single nucleotide pair, or whether cleavage occurs at several sites. However, for targeted integration, cleavage within a range of nucleotides is generally sufficient, and cleavage between particular base pairs is not required.

As discussed in detail below, the cleavage protein, or its encoding polynucleotide, is introduced into a cell. Once introduced into, or expressed in, the cell, the cleavage protein binds to the target sequence in the constitutively expressed gene and cleaves within this gene.

Delivery

The nucleic acids as described herein may be introduced into a cell using any suitable method.

Expression of a cleavage protein in a cell can result from delivery of the cleavage protein to the cell or by delivery of a polynucleotide encoding the cleavage protein to a cell, wherein the polynucleotide is transcribed, and the transcript is translated, to generate the cleavage protein. Trans-splicing, polypeptide cleavage and polypeptide ligation can also be involved in expression of a protein in a cell.

The cleavage protein can be introduced as a polypeptide and/or a polynucleotide. Two polynucleotides, each comprising a sequence encoding a cleavage protein, can be introduced into a cell, and when the cleavage proteins are expressed and each binds to its target sequence, cleavage occurs at or near the target sequence. Alternatively, a single polynucleotide comprising sequences encoding one or more cleavage proteins may be introduced into a cell. Polynucleotides can be DNA, RNA or any modified forms or analogues or DNA and/or RNA.

In certain embodiments, one or more cleavage proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding sequences described herein can also be cloned into an expression vector, for administration to a plant cell, animal cell, preferably a mammalian cell or a human cell, fungal cell, bacterial cell, or protozoal cell using standard techniques.

In certain embodiments, the vector comprising the exogenous nucleic acid and/or encoding the cleavage proteins are delivered in vivo or ex vivo for gene therapy uses. Non-viral vector delivery systems for delivering polynucleotides to cells include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids in vivo or ex vivo include electroporation, lipofection, microinjection, biolistics, virosomes, liposomes, immunoliposomes, polycation or lipid:nucleic acid conjugates, naked DNA, artificial virions, viral vector systems (e.g., retroviral, lentivirus, adenoviral, adeno-associated, vaccinia and herpes simplex virus vectors and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

In certain embodiments, for example, in which transient expression of a cleavage protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials PA317/pLASN was the first therapeutic vector used in a gene therapy trial. Transduction efficiencies of 50% or greater have been observed for MFG-S packaged vectors.

Recombinant adeno-associated virus vectors (rAAV) are a promising alternative gene delivery systems based on the defective and nonpathogenic parvovirus adeno-associated virus subtypes. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (In addition, self complementary recombinant adeno-associated virus (scAAV)-dervived vectors can be used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically comprise the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which comprises a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the vector comprising the exogenous nucleic acid and or encoding the cleavage protein be delivered with a high degree of specificity to a particular tissue type. Accordingly, a viral vector can be modified to have specificity for a given cell type by expressing a ligand as a cleavage protein with a viral coat protein on the outer surface of the virus. The ligand is chosen to have affinity for a receptor known to be present on the cell type of interest. Moloney murine leukemia virus may be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a cleavage protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to comprise specific uptake sequences which favour uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a vector comprising the exogenous nucleic acid and/or a polynucleotide encoding a cleavage protein, and re-infused back into the subject organism (e.g., patient). Various cell types suitable for ex vivo transfection are well known to those of skill in the art.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells).

Vectors (e.g., retroviruses, adenoviruses, liposomes, etc.) comprising nucleic acids as described herein can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors.

Pharmaceutically acceptable carriers are determined in part by the particular composition being administered, as well as by the particular method used to administer the composition.

Accordingly, there is a wide variety of suitable formulations of pharmaceutical compositions available.

As noted above, one or more cleavage proteins can also be introduced into the cell as polypeptides. Non-limiting examples of protein delivery vehicles include, "membrane translocation polypeptides," for example peptide have amphiphilic or hydrophobic amino acid subsequences that have the ability to act as membrane-translocating carriers, toxin molecules, liposomes and liposome derivatives such as immunoliposomes (including targeted liposomes).

The vector comprising the exogenous nucleic acid, cleavage proteins, and/or expression vectors encoding cleavage proteins can be administered directly to the patient for targeted cleavage integration into the constitutively expressed gene for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like.

Pharmaceutically acceptable carriers are determined in part by the particular composition being administered, as well as by the particular method used to administer the composition. Accordingly, there is a wide variety of suitable formulations of pharmaceutical compositions available and known to the person skilled in the art.

Formulations suitable for parenteral administration, such as, for example, by intravenous, intramuscular, intradermal, and subcutaneous routes, include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Methods of Treatment

The exogenous nucleic acid may comprise a sequence encoding a polypeptide that is lacking or non-functional in a subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Accordingly, the exogenous nucleic acid may comprise a disease-causing or disorder-causing genetic variation or mutation.

Accordingly, disclosed herein is a method of preventing or treating a disease or disorder in a subject, the method comprising administering to the subject the vector comprising the exogenous nucleic acid or a cell comprising the exogenous nucleic acid.

Also disclosed is use of the vector comprising the exogenous nucleic acid or a cell comprising the exogenous nucleic acid in the manufacture of a medicament for treating a disease or disorder in a subject.

Also disclosed is the vector comprising the exogenous nucleic acid or a cell comprising the exogenous nucleic acid for use in preventing or treating a disease or disorder in a subject.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature.

All patents, patent applications and publications mentioned herein are hereby incorporated by reference, in their entireties, for all purposes.

It is to be understood that, if any prior art publication is referred to herein, such reference does not constitute an admission that the publication forms a part of the common general knowledge in the art, in Australia or any other country.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

EXAMPLES

Example 1—Vector

Embodiments of the vector as used in the following examples was produced using standard recombinant engineering techniques using a bacterial artificial chromosome (BAC) spanning the GAPDH locus together with insertion of the translation interruption-reinitiation signal and the relevant exogenous nucleic acid (FIG. 1).

Example 2—Human Embryonic Stem Cells

Tissue culture flasks were treated with 0.1% gelatin solution (in PBS) for 10 minutes at room temperature. The gelatin solution was then aspirated and replaced with the appropriate volume of MEF media. Cryovials of feeder cells were thawed in a water bath at 37° C. for 3 minutes, and the cell suspension was then transferred to a 15 ml Falcon tube containing 10 ml MEF media. A 10 µl aliquot of this solution was used to complete a cell count.

The falcon tube containing feeder cells was centrifuged for 4 minutes at 3600 rpm at 4° C. to pellet the cells. The supernatant was aspirated and cells resuspended in MEF media at a concentration of $1\times10^6$ cells per ml. The appropriate volume of cells was then added to the gelatin treated flasks, which were subsequently placed in a 37° C. incubator at 4% $O_2$.

hESCs were passaged either when they were over 90% confluent or every four days.

Cells in T75 flasks were washed with 15 ml Phosphate Buffered Saline (PBS). 2 ml TrypLE-Select was added and the flask was turned in order to ensure all cells were coated, before being incubated for 4 minutes at 37° C. The TrypLE-Select was then diluted by the addition of 8 ml PBS. Cells were dislodged by gentle tapping of flasks and by repeatedly pipetting the PBS/cell solution across the flask surface. The cell solution was transferred to a 15 ml falcon tube, a 10 µl aliquot taken to perform a cell count, and then centrifuged at 3600 rpm for 4 minutes at 4° C. to pellet the cells. The supernatant was aspirated and the cells resuspended in hESC media to give an approximate final concentration of $1\times10^6$ cells per ml. The pellet was disaggregated by repeated pipetting in the falcon tube. Finally, the appropriate volume of cells was then added to the prepared flasks with fresh feeders.

hESCs are best for differentiation studies if they are passaged fewer than 24 hours before the differentiation experiment is set up. There are two ways this can be done. In some instances, cells are passaged onto MEF medium treated plates around 1-2 hours before set up. This short term treatment selects for live cells that quickly adhere to the plastic. After around 1-2 hours, the plates are washed with PBS and live adherent cells collected, counted and subsequently used for differentiation. Alternatively, the pre-differentiation passage can be conducted the day prior to differentiation. In this case, hESC cultures at around 80% confluence are passaged onto a MEF media treated flask and incubated at 37° C. overnight.

Immediately prior to differentiation, STEMDiff APEL media was prepared with cytokines and growth factors at appropriate concentrations according to the desired differentiated fate (see Table 1). Cells were harvested, counted and pelleted, then resuspended in STEMDiff APEL media at a concentration of $1\times10^6$ cells/ml. An adequate amount of this suspension was added to the STEMDiff APEL and cytokine solution such that there would be 3 000 cells in 50 µl of media per well of a round-bottomed low attachment 96-well plate (see Table 1). Plates were centrifuged for 5 minutes at 3600 rpm in 4° C. in order to encourage aggregation and subsequent formation of embryoid bodies (EBs): three-dimensional masses of adherent, differentiating cells. Plates were then incubated at 37° C. at 4% $O_2$, 5% $CO_2$.

TABLE 1

| Growth Factors | Cardiac Cell Differentiation Final Concentration | Endothelial Cell Differentiation Final Concentration | Blood Cell Differentiation Final Concentration |
| --- | --- | --- | --- |
| BMP4 | 40 ng/ml | 20 ng/ml | 20 ng/ml |
| SCF | 40 ng/ml | 40 ng/ml | 50 ng/ml |
| VEGF | 40 ng/ml | 30 ng/ml | 50 ng/ml |

TABLE 1-continued

| Growth Factors | Cardiac Cell Differentiation Final Concentration | Endothelial Cell Differentiation Final Concentration | Blood Cell Differentiation Final Concentration |
| --- | --- | --- | --- |
| ActA | 40 ng/ml | 5 ng/ml | 2 ng/ml |
| Wnt3a | 40 ng/ml | 0.25 µl | |

StemDIFF APEL used as base of media, 5 ml/96-well plate.

Depending on the aim of the differentiation experiment, cells were either media changed on Day 3 or Day 4 using a multi-channel aspirator and multi-well pipette. Cells being pushed towards a cardiomyocyte fate were media changed without replenishing growth factors, in StemDIFF APEL media alone on Day 3 (100 µl/well). Endothelial and blood cell differentiation media changes included growth factors, outlined in Table 2. Particular care needed to be taken in order to not aspirate the newly formed EBs.

TABLE 2

| Growth Factors | Endothelial Cell Differentiation Final Concentration | Blood Cell Differentiation Final Concentration |
| --- | --- | --- |
| BMP4 | 20 ng/ml | 20 ng/ml |
| SCF | 40 ng/ml | 100 ng/ml |
| VEGF | 30 ng/ml | 50 ng/ml |
| IL3 | | 25 ng/ml |
| IL 6 | | 25 ng/ml |
| bFGF | | 10 ng/ml |
| Apelin | | 50 ng/ml |
| Epo | | 2 U/ml |

StemDIFF APEL used as base of media, 5 ml/96-well plate.
Media changed on Day 4, 100 µl per well.

In order to continue the differentiation experiment to a stage at which mature cell types would emerge. EBs were sometimes transferred to new plates that allowed them to attach and spread out. For non-hematopoiefic mesoderm differentiations. Day 7 EBs were transferred to a gelatinized 10 cm tissue culture dish. Prior to transfer, the existing media was aspirated from wells of all 96-well plates and replaced with 100 µl of BEL media. The EBsin their new media were then collected and transferred to the 10 cm tissue culture dish (approximately 100 EBs to one culture dish). These cultures could then be maintained for extended times providing medium was changed regularly: every 3-7 days depending on cell density.

In the case of blood differentiation experiments, 6-well plates were gelatinized in preparation for the transfer of ERs comprising hematopoietic precursors ('plate down'). On Day 7, EBs were transferred from 96-well plates in their existing media into the 6-well plates—approximately 20-25 EBs per well—and incubated at 37° C. overnight. On Day 8, after the EBs had attached to the plates, media was changed to APEL with specific blood growth factors (see Table 3).

TABLE 3

| Growth Factor | Final Concentration |
| --- | --- |
| BMP4 | 20 ng/ml |
| SCF | 100 ng/ml |
| VEGF | 50 ng/ml |
| IL3 | 25 ng/ml |
| IL6 | 25 ng/ml |
| TpO | 50 ng/ml |
| Flt3 | 50 ng/ml |
| G-CSF | 50 ng/ml |

TABLE 3-continued

| Growth Factor | Final Concentration |
|---|---|
| GM-CSF | 25 ng/ml |
| IGF-2 | 25 ng/ml |
| bFGF | 10 ng/ml |
| Apelin | 50 ng/ml |
| EPO | 2 U/ml |

StemDIFF APEL used as base of media, 18 mL 6-well plate.
Media changed on Day 8, 3 ml per well.

Embryoid bodies were collected from 96-well plates into a tube and allowed to settle into a pellet by gravity. The supernatant was aspirated, and the EBs were rinsed with 5 ml PBS, then pelleted in a centrifuge at 3600 rpm at 4° C. for 4 minutes. The PBS was aspirated and the pellet of EBs was resuspended in 1 ml T-Select. The tube of EBs was incubated in a waterbath at 37° C. for 7 minutes.

EBs were dissociated into single cells by passing the suspension through a 21-gauge needle attached to a 3 ml syringe up to three times. 1 ml StemDIFF APEL was added to the single cell suspension, which was then pelleted by centrifugation (3600 rpm, 4° C., 4 minutes). The supernatant was removed, and the pellet was resuspended in 1 ml StemDIFF APEL and then transferred to FACS tube filter cap using a 1 ml Gilson pipette. The filtered cell suspension was re-pelleted in a centrifuge (3600 rpm, 4° C., 2 minutes). Finally, the excess media was removed and the pellet resuspended in an appropriate volume of StemDIFF APEL (no more than 1 ml—dependent on the pellet's size) in order to perform a cell count.

APEL medium with double the amount of albucult and supplements and 2% MC was used for methylcellulose colony forming assays. This was diluted 1:1 with APEL-IMDM in a falcon tube and mixed on a roller at 4° C. for at least 30 minutes. Growth factors were added (Table 4) and the tube was mixed for a further 10 minutes on the roller. This solution is referred to as 'MC-APEL'.

Triplicate wells containing 3,000 cells per well were set up for each sample in a flat-bottomed 24-well low attachment plate. To perform the assays, 9,000 cells representing each sample were added to a 10 ml tube—along with 1.8 ml MC-APEL with growth factors, which was dispensed using an 18-gauge needle and a 3 ml syringe, 30 µl of matrigel was added to the tube at this point. The solution of cells and MC-APEL was carefully and thoroughly mixed by repeated intake and gentle expulsion with the needle and syringe, and the total solution was then distributed into each well of the 24 well plate (500 µl well). Where possible, the MC cultures were placed in the inner wells of the plate, and the outer wells were filled with 1 ml sterile water to provide humidity and to prevent desiccation. The plate was then incubated at 37° C. for up to 21 days.

TABLE 4

| Component | Final Concentration |
|---|---|
| SCF | 100 ng/ml |
| VEGF | 50 ng/ml |
| IL-3 | 25 ng/ml |
| IL-6 | 25 ng/ml |
| bFGF | 10 ng/ml |
| BMP4 | 20 ng/ml |
| Apelin | 50 ng/ml |
| EPO | 2 U/ml |
| Matrigel | 30 µl/ml |

Cells were analysed by flow cytometry throughout the course of differentiation: either at the embryonic stem cell stage, the EB stage or at the stage at which they had formed mature cells. Prior to disaggregation using T-Select, cells were washed once with PBS. In the case of undifferentiated hESCs, cells were harvested by adding an appropriate volume of T-Select such that all cells were coated. Samples were then incubated at 37° C. (see Table 5). In the case of EBs and mature tissue, cells were incubated in T-Select for the times shown in Table 5, prior to disaggregation with a 23 G needle attached to 5 ml syringe. The resultant single cell suspension was washed with PBS and subsequently pelleted by centrifugation (4 min, 3600 rpm, 4° C.).

Cells were resuspended in 1 ml of FACS wash and then pelletted once more. The supernatant was aspirated and samples were resuspended in 500 µl of FACS wash. To remove cell clumps, samples were filtered through the cap of a FACS tube, and centrifuged at 3600 rpm for 3 mins at 4° C. Following aspiration of the supernatant, the pellet was resuspended in FACS block such that there was enough volume to have 50 µl of cell suspension per antibody stain used.

Antibodies directed against specific cell surface receptors were added to the FACS tubes containing 50 µls of the cell suspension and then left to incubate in the dark on ice for at least 15 minutes. Following this period, samples were washed by the addition of 300 µl of FACS wash, before being pelleted by centrifugation. The supernatant was aspirated and a second FACS wash was carried out in the same manner. Two washes were necessary after staining to ensure unbound antibodies were completely removed.

Once all antibody stains were completed, each sample was resuspended in 300 µl of FACS wash with 10% Propidium Iodide (PI). PI is a small molecule that enters dead cells and binds to DNA and fluoresces when excited by an external light source. Live cells exclude PI and thus the inclusion of PI in the FACS wash solution provides a means of identifying dead cells, which can be subsequently excluded from analyses carried out using a flow cytometer.

TABLE 5

| Stage | Incubation time in T-Select |
|---|---|
| Day 0 embyronic stem cells | 4 mins |
| Day 4-6 embryoid bodies | 6 mins |
| Day 7-10 mature tissue | 10 mins |
| Day 11+ mature tissue | 15 mins |

RNA synthesis in preparation for Quantitative Polymerase Chain Reaction (Q-PCR) was carried out according to the Qiagen RNeasy Mini Kit manual. cDNA synthesis was completed using the Tetro cDNA Synthesis Kit according to the product manual.

GAPDH and Oct4 Taqman probes were ordered from Applied Biosystems (cat # Hs999999 ml and # Hs01895061 ul respectively). mCherry Taqman probe was custom designed and ordered from Applied Biosystems. Q-PCR was carried out according to standard protocols.

Statistical analysis was performed using GraphPrism and/or Excel. Specific tests used are outlined in Results.

Figure 2A:
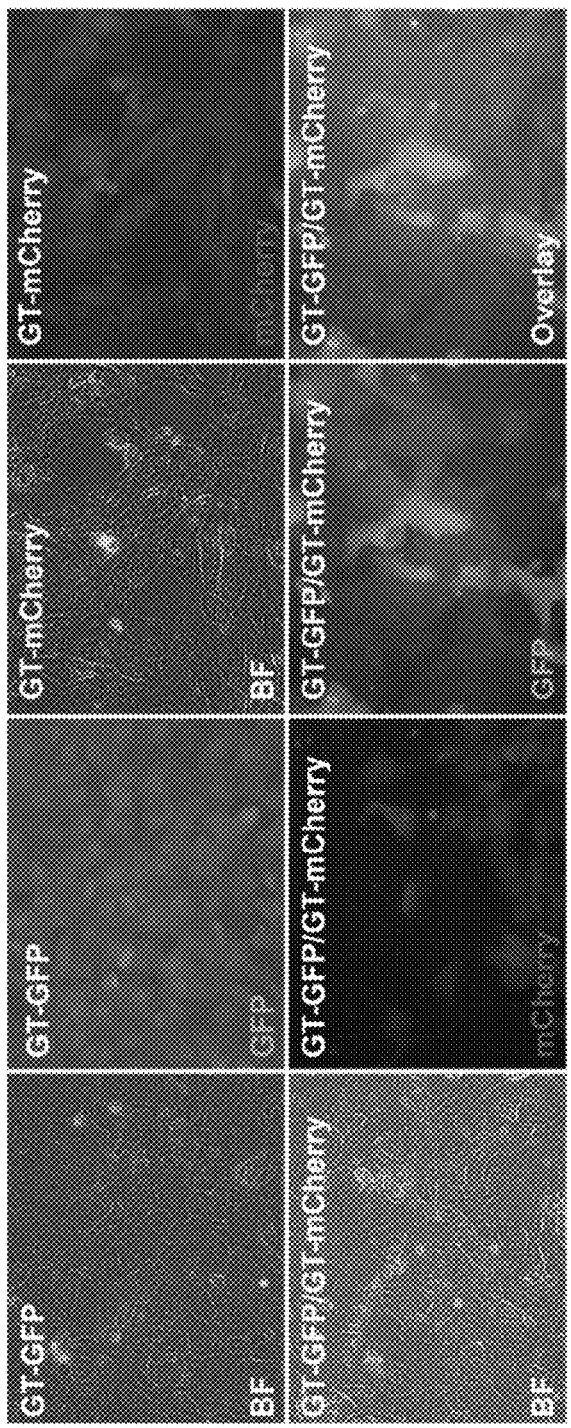
FIG. 2 provides fluorescent photomicrographs and flow cytometry plots of GT-GFP and GT-mCherry hESC co-cultures according to Example 3. A Top row of micrographs show cultures of lines cultured separately. The bottom row shows images from a co-culture well that contained equal numbers of cells from both lines. B Flow cytometry data. The first two plots show flow cytometry data for GT-GFP and GT-mCherry d0 hESCs when cultured separately. The plot showing co-culture data shows two distinct populations.

Example 3—Cell Autonomous Retention of Fluorescent Proteins in Co-Cultures of GT-GFP and GT-mCherry hESCs It is possible that mCherry$^{neg}$ cells could acquire mCherry fluorescence from mCherry$^{pos}$ cells grown in co-culture. If true, the utility of ubiquitously tagging cells with mCherry could be compromised. To test this, an equal number of GT-GFP and GT-mCherry hESCs were cultured in 6-well plates together in feeder-free conditions for 2 weeks. FIG. 2 shows a set of fluorescent microscopy images depicting the co-cultures following one week of co-culture.

Figure 2B:
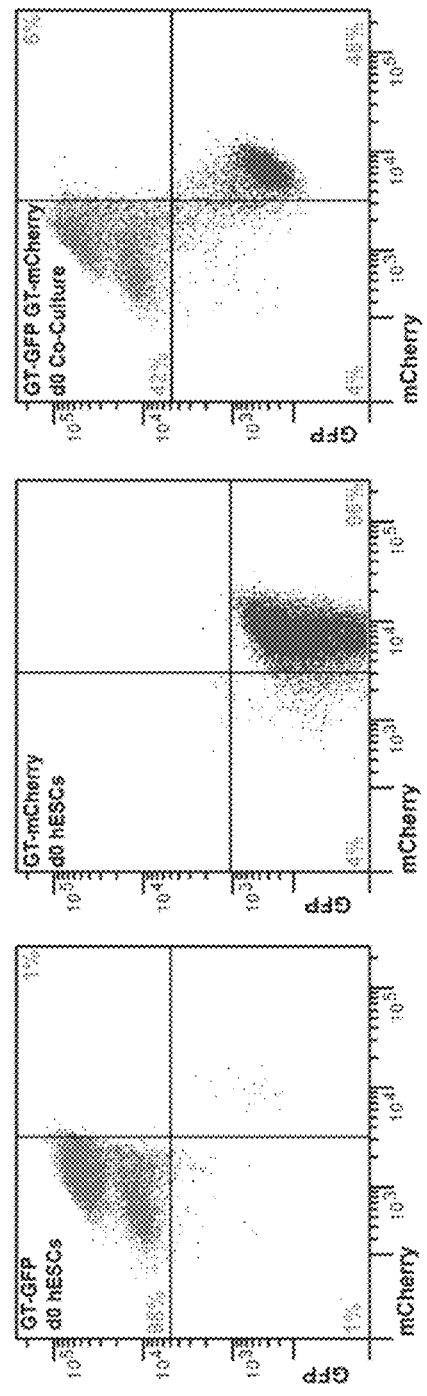

Examination of the mixed cultures showed they consisted of cell clusters comprising only a single cell type as well as clusters comprising both cell types intermingled. Following a further week, and an additional passage, the mixed cultures were analysed by flow cytometry (FIG. 2B). This analysis showed that mixed cultures comprised two distinct populations, suggesting that there was no exchange of GFP or mCherry between cells and that the function of the transgene remained restricted to the specific cell in which it was expressed.

Example 4—Vector Functionality Throughout Differentiation

We hypothesised that genes inserted from the GAPDH locus would continue to be expressed during the course of differentiation. In order to test this, GT-GFP hESCs were differentiated towards the hematopoietic lineage according to the schematic shown in FIG. 3.

Flow cytometry analysis and fluorescent microscopy was conducted at day 0 (i.e., undifferentiated hESCs), at day 4 of embryoid body formation, and at day 14, a time at which differentiated cells had started to express markers of hematopoietic cells. These markers included the blood progenitor/endothelial marker CD34, the myeloid blood marker CD45, the endothelial marker CD31, the mature erythroid marker glycophorin-A and leukocyte-endothelial cell adhesion molecule VCAM-1.

Figure 4:
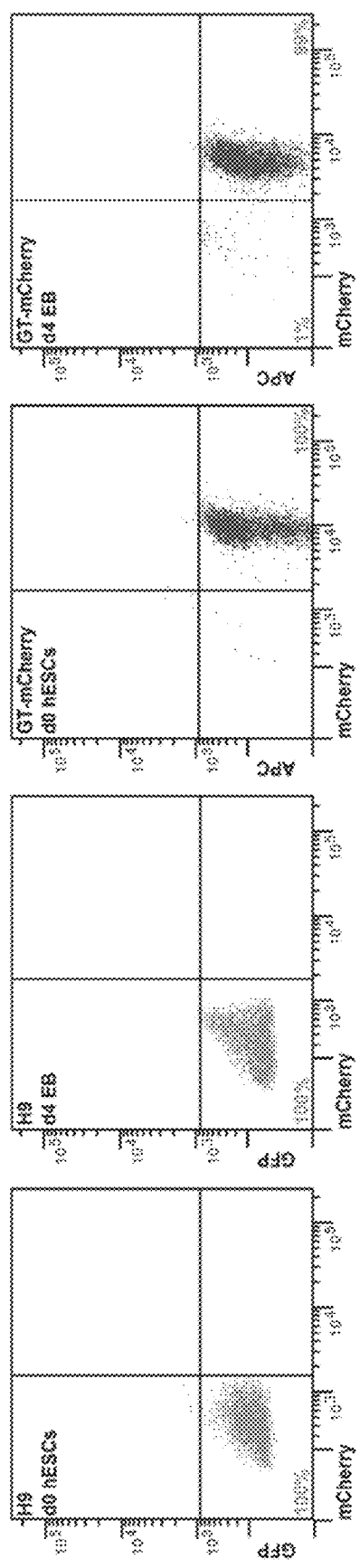
FIG. 4 provides flow cytometry plots for H9 and GT-mCherry lines according to Example 4. H9 cells were double negative for GFP and mCherry at all stages of differentiation. GT-mCherry cells expressed mCherry at high levels at both hESC and EB stages of differentiation.
Figure 5A:
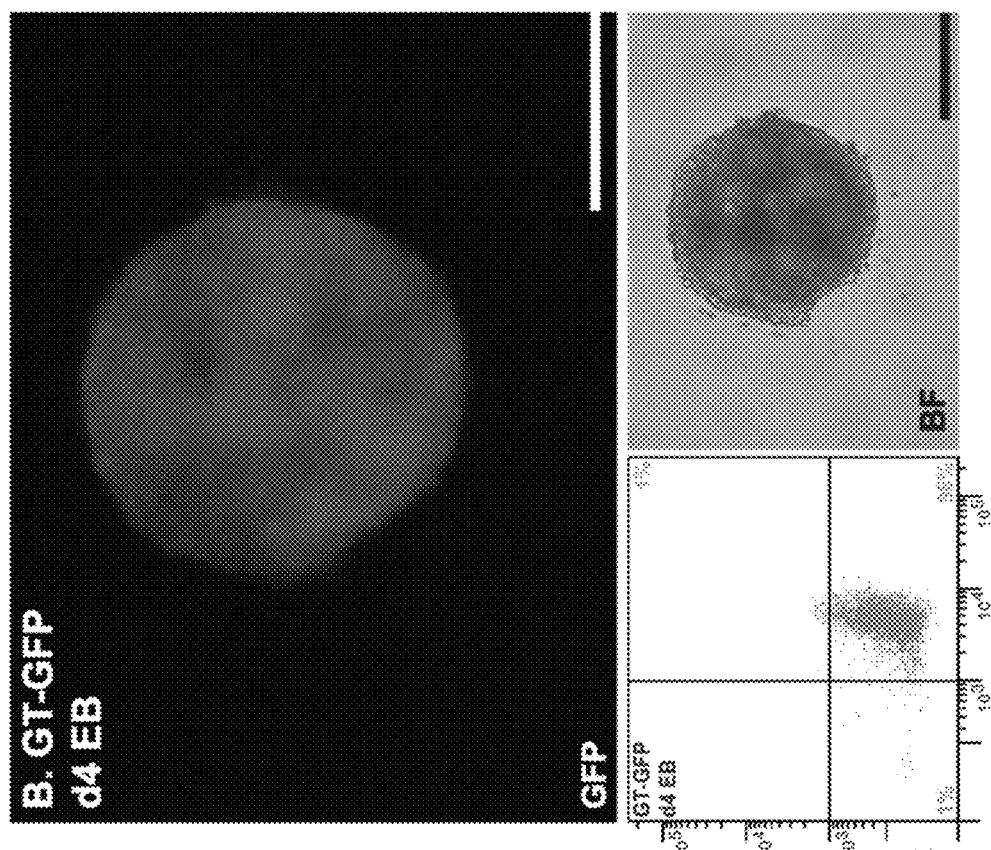
FIG. 5 provides fluorescent photomicrographs and flow cytometry plots of hematopoeitic differentiation of the GT-GFP line according to Example 4. A. GT-GFP hESCs in culture with corresponding flow cytometry data and bright field image below. B. Day 4 embryoid body of the GT-GFP line and flow cytometry data and bright field image below. C-D. Fluorescent micrographs of day 14 differentiated GT-GFP tissue with corresponding bright field images below each, as well as related flow cytometry data, showing expression of endothelial and blood cell markers indicated. GLY refers to glycophorin-A. All scale bars 200 μm.
Figure 5B:
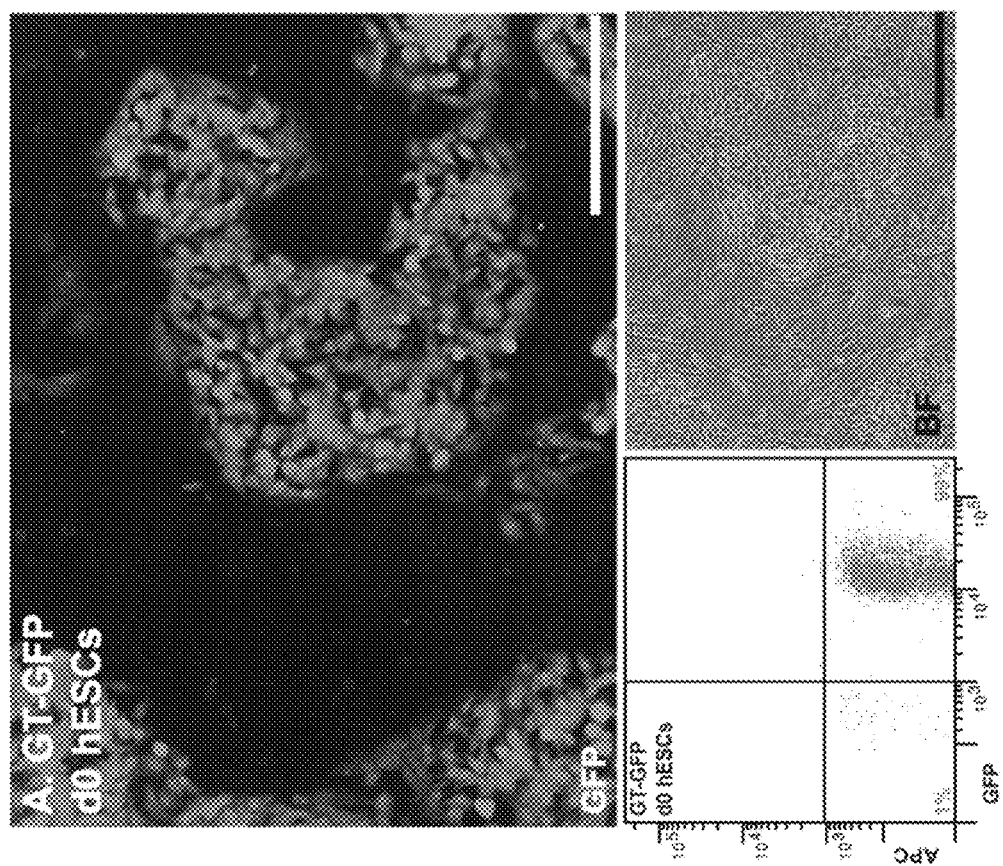
Figure 5E:
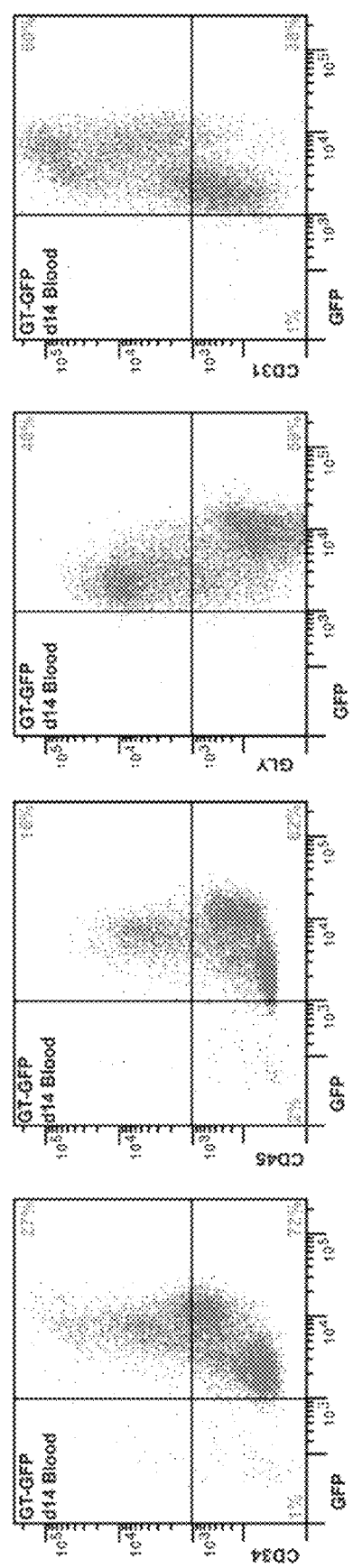

As shown in FIG. 4, at each experimental stage examined, a high proportion of cells retained expression of the GFP reporter gene (greater than 95%). In addition, for each time point, the intensity of expression was relatively uniform across the population of expressing cells: the mean average fluorescence intensity across the three timepoints was consistently above 4,000 arbitrary units. These results were supported by fluorescent microscopy observations (see FIG. 5).

Inspection of day 14 cultures showed the development of colonies with an endothelial appearance, and round blood cells, either budding off this endothelial material or suspended in the medium. Following antibody staining, flow cytometry analysis confirmed the presence of differentiated cell types, with 60% of cells expressing blood progenitor/endothelial marker CD31, 40% expressing glycophorin-A, a marker of mature erythroid cells, and 16% expressing the pan-hematopoietic marker CD45 (amongst others shown in FIG. 5). All of these populations maintained robust GFP expression.

Similar experiments were also carried out to examine the expression of mCherry in GT-mCherry hESCs. In flow cytometry and fluorescence microscopy experiments for both coloured lines (GT-GFP and GT-mCherry), parental (uncoloured) H9 hESCs were used as a negative control (FIG. 4).

These experiments show that GT-GFP and GT-mCherry expression persists at robust levels in differentiated progeny, and therefore could serve as a means of identifying or tracking cells within cultures comprising mixed populations.

Example 5—Clonal Behaviour of GT-GFP and GT-mCherry Progenitor Cells in Methylcellulose-Matrigel Cultures Colony forming assays are a method for enumerating the frequency of progenitor cells within a cell population. In this assay, colonies of cells develop from single cells suspended in a semi-solid medium, such as methylcellulose (MC). Each colony is taken to signify the presence of a single progenitor cell with colony forming ability. Although it has been previously established that colonies arising in MC cultures are clonally derived, this same issue has not been directly addressed for MC-Matrigel (MCM) cultures.

Figures 6A, 6B:
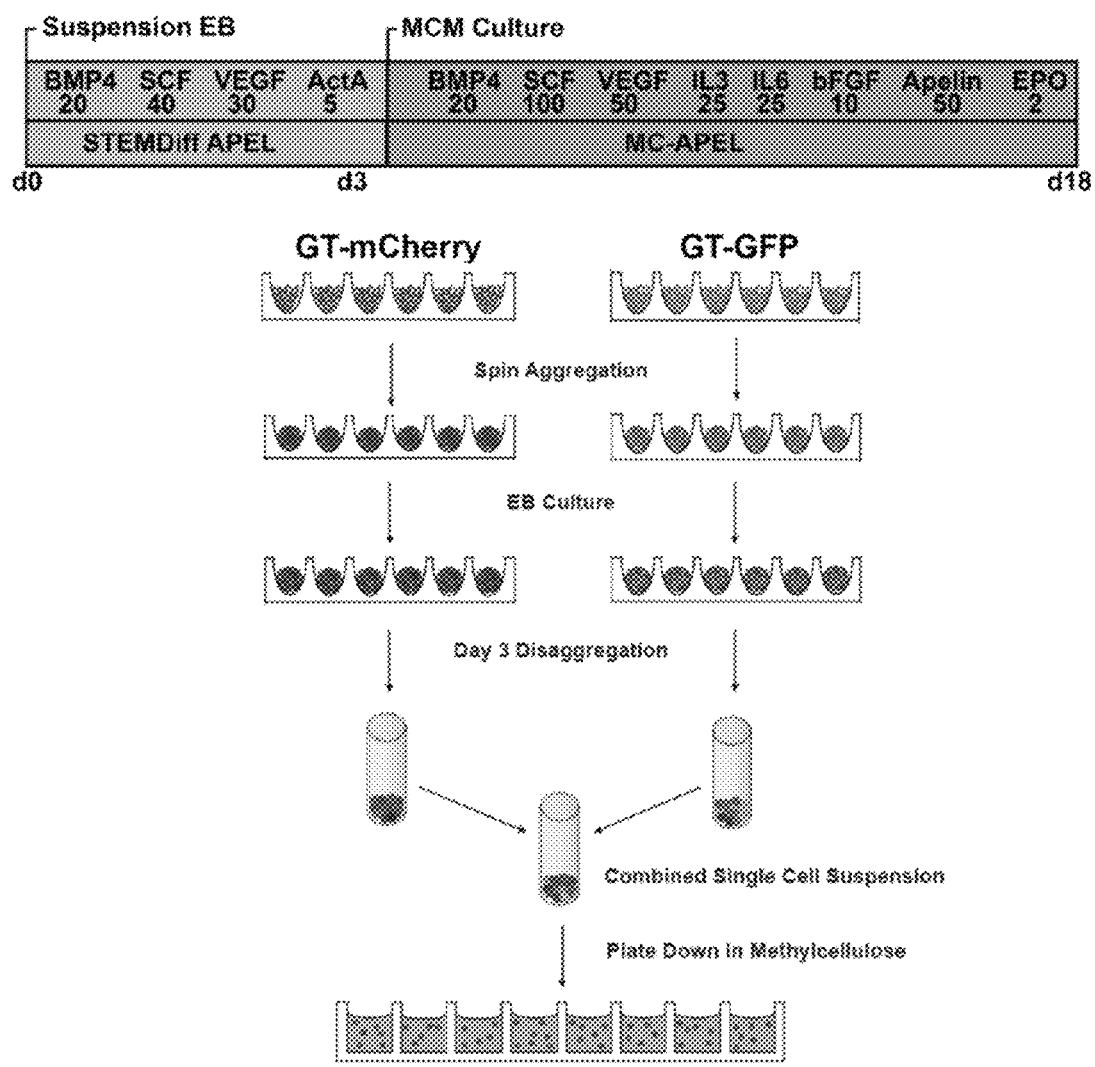
FIG. 6 is a schematic of hematopoeitic colony-forming assay using day 3 EBs. A. Schematic of differentiation protocol. Growth factors used are indicated with concentrations listed underneath. The bottom row shows base media for each stage of the experiment. B Set up of MCM cultures using day 3 EBs.

To address this question, we set up MCM cultures in which day 3 progenitors representing the GT-GFP and GT-mCherry hESC lines were seeded together. In this experiment, day 3 EBs of each line were generated under conditions designed to direct cells towards a hematopoietic mesodermal fate. Following disaggregation, the single cell suspension of differentiating cells was then distributed amongst wells of a low attachment 24 well plate (FIG. 6). Three cell densities were used—500 H9 GT-GFP cells and 500 H9 GT-mCherry cells (low density), 1500 cells of each line per well (medium density) and 2000 cells of each line (high density). This range of densities was chosen to ensure the forming colonies were sufficiently separated to enable them to be counted. An equal number of GT-Cherry and GT-GFP cells was used for each density.

Colonies were scored on day 14 and were categorised into 5 different groups; completely red (mCherry$^{pos}$), completely green (GFP$^{pos}$), mixed (comprising a substantial number of both red and green cells), trace red, or trace green (FIG. 7). Mixed colonies comprising roughly equal numbers of red and green cells may have resulted from the juxtaposition of the two cell types at the time of seeding. Trace colonies are those that were predominantly one colour, but comprised one or two cells of the opposite colour. There are a number of possible explanations of the 'trace' colonies. For example, it is possible that the trace component of the colony represented cells that have migrated to that colony from elsewhere. Another possibility is that cells that had limited proliferative potential were engulfed by the expanding colony of the opposite colour. Trace colonies could have also resulted from a completely coloured colony growing into the path of a cell of the opposite colour, enveloping it and inhibiting its own development.

Colony scoring data is displayed in FIG. 8A. Each column represents the average number of colonies taken from three technical replicates of the lowest density wells. The medium and high density wells were too overcrowded to accurately count. The most common colony type was totally green, while the second most common was the 'mixed' colony. Total red colonies were the least common, apart from trace colonies which were relatively rare.

On day 18, colonies were harvested from MCM cultures and dissociated into single cells in order to be analysed by flow cytometry. As shown in FIG. 8B, this analysis indicated that 63% of cells expressed GFP (GFP$^{pos}$), whilst 31% expressed mCherry (mCherry$^{pos}$). This correlates with the scoring data, where if 'mixed' colonies were assumed to comprise an equal number of green and red cells, the fraction of GFP$^{pos}$ and mCherry$^{pos}$ cells in cultures overall would be 66% and 33% respectively (FIG. 8C).

Example 6—Kinetics of Induction of the GT-iCherry hESC Line

An important use of the vector disclosed herein would be as a basis for the conditional over-expression of genes. The GT-iCherry vector was constructed with in mind (FIG. 9). In this embodiment of the vector, mCherry was positioned downstream of an artificial promoter that comprises binding sites for the reverse Tet activator (rTA) protein. In the presence of doxycycline, this protein, which is also expressed from the same GT vector, binds to and activates transcription of promoters comprising the correct binding sequence (shown as TetO in FIG. 9). In cells comprising a correctly integrated GT-iCherry vector, we expected that mCherry would be expressed following addition of doxycycline.

With the aim of testing the kinetics of mCherry induction expressed from the GT-iCherry vector, a time-course experiment was carried out to determine the optimal duration of treatment with doxycycline. GT-iCherry hESCs were exposed to 1 µg/ml doxycycline for either 12 h, 18 h, 24 h, 36 h, 48 h or 72 h and analysed via flow cytometry. Samples of GT-iCherry hESCs that had not been treated with the drug and a sample of H9 hESCs were used as negative controls. For flow cytometry analysis, the mCherry positive region was determined by setting quadrants on the FACS plot such that all cells in the untreated GT-iCherry samples were negative on the mCherry axis.

Figure 10A:
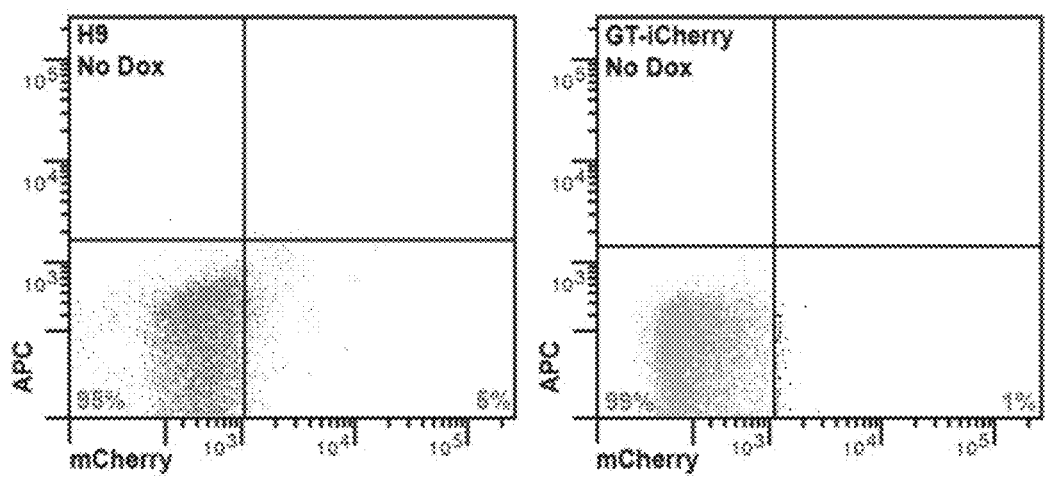
FIG. 10 provides flow cytometry plots and a line graph representing mCherry induction in doxycycline treated GT-iCherry hESCs. A. Flow cytometry analysis of negative control samples; H9 hESC and GT-iCherry hESCs before treatment with (No Dox). B. Flow cytometry analysis of GT-iCherry hESCs treated with doxycycline for the time periods indicated. Quadrants were positioned in reference to the control samples shown in A. Data is from one representative experiment of a set of 3. C. Average mCherry fluorescence intensity in doxycycline treated GT-iCherry hESCS as a function of time. The dotted red line represents the average fluorescence intensity of the constitutively red GT-mCherry hESC line (10896+/−SEM: 650, n=3). Error bars represent SEM (n=3).
Figure 10B:
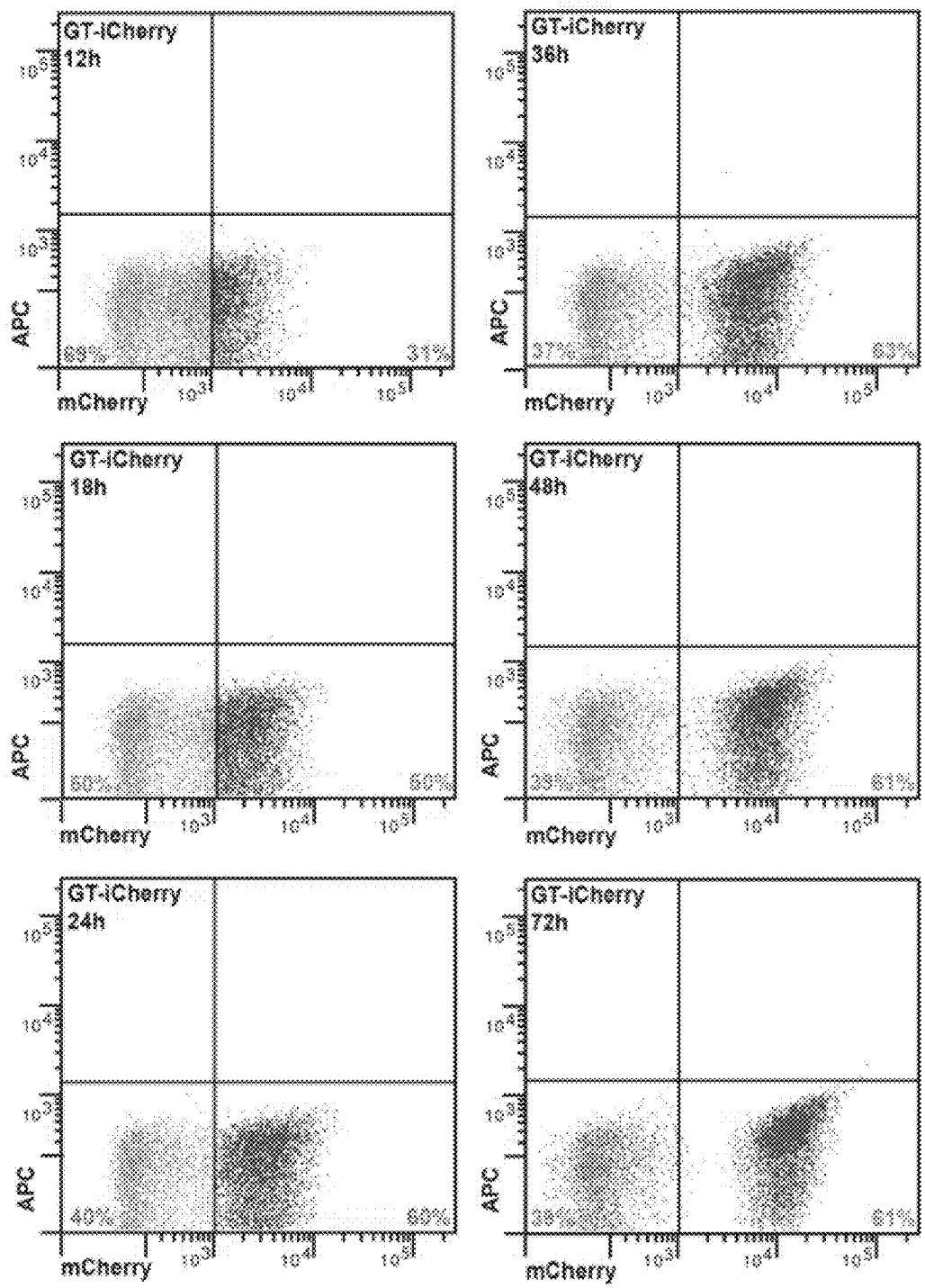

Flow cytometry results reported in FIG. 10 show that the emergence of an mCherry$^{pos}$ population can be seen as soon as 12 hours after addition of doxycycline. By 24 hours, this population is clearly distinct from cells which have failed to switch on the transgene. It is unclear why a substantial fraction of the cells remain mCherry negative although there are a number of explanations that involve the potential non-clonality of line, or the possibility of gene silencing. The positive and negative populations become more distinct after 36 hours of treatment, and by 72 hours the mCherry$^{pos}$ cells formed a distinct highly fluorescent uniform population.

Figure 10C:
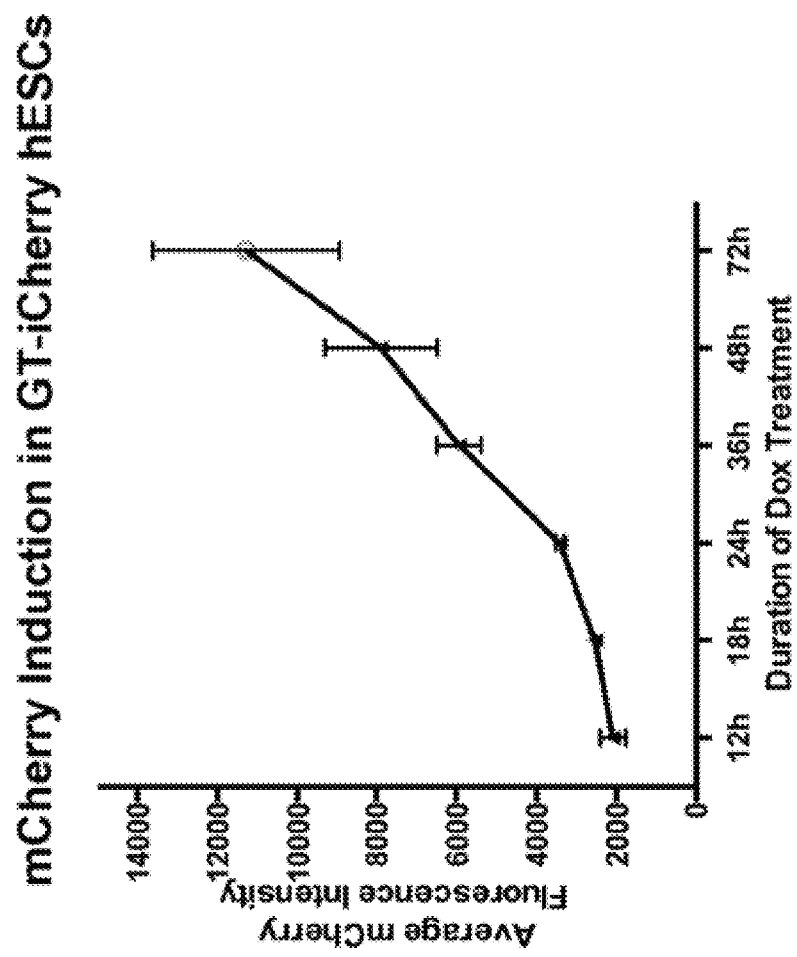

The analysis shown in FIG. 10C is based on average fluorescence intensity (n=3) of the mCherry$^{pos}$ cells and suggests that the ideal treatment time for the GT-iCherry hESCs line is between 48 hours and 72 hours. This is where the average fluorescence intensity is equal to that of GT-mCherry hESCs (n=3), which in this instance served as a positive control.

Example 7—Decay of mCherry Expression in GT-iCherry hESCs Following Cessation of Doxycycline Treatment To further define the behaviour of the GT-iCherry line, we next investigated the amount of time it took for mCherry levels to return to baseline following the removal of doxycycline. In these experiments, GT-iCherry hESCs were seeded in feeder-free 6 well plates and cultured in hESC media with doxycycline (1 µg/ml) for 3 days. Media was then changed to standard hESC media for subsequent days of the experiment. Flow cytometry was used to quantify the percentage of the mCherry$^{pos}$ cells each day following doxycycline removal. In addition, this experiment also provided information on the intensity of mCherry fluorescence in mCherry expressing cells.

Figure 11A:
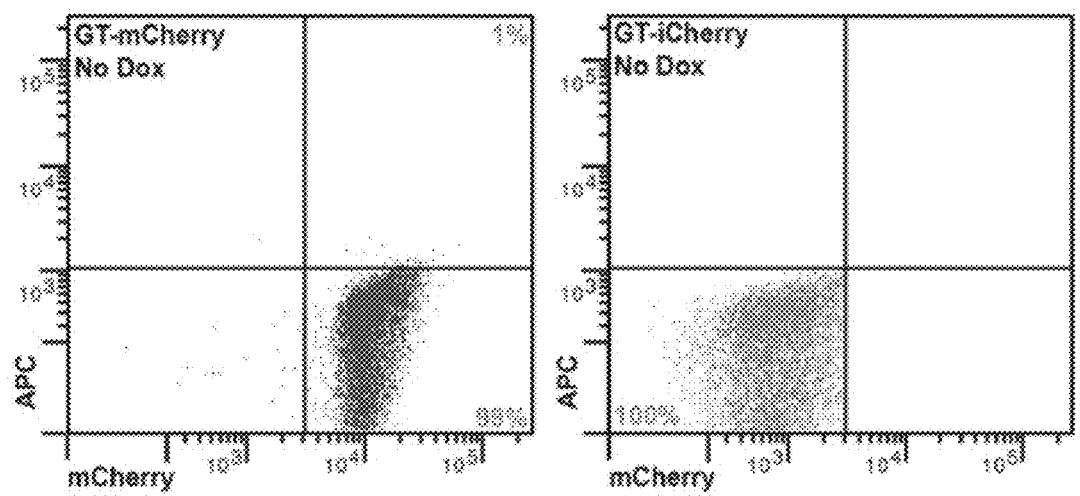
FIG. 11 provides flow cytometry plots and a line graph representing decay of mCherry expression in GT-iCherry hESCs according to Example 7. A. Flow cytometry analysis of GT-mCherry hESCs (positive control) and GT-iCherry hESCs prior to induction with doxycycline (negative control). B. Flow cytometry analysis of GT-iCherry hESCs following cessation of doxycycline treatment. The number of days since doxycycline removal is indicated. Quadrants were set in relation to positive and negative populations shown in A. Data is from one representative experiment of a set of 3. C. Fraction of mCherry$^{neg}$ cells each day following removal of doxycycline. Three sets of flow cytometry data were combined to attain the average frequency of mCherry$^{neg}$ cells per time point. Error bars represent SEM (n=3).
Figure 11B:
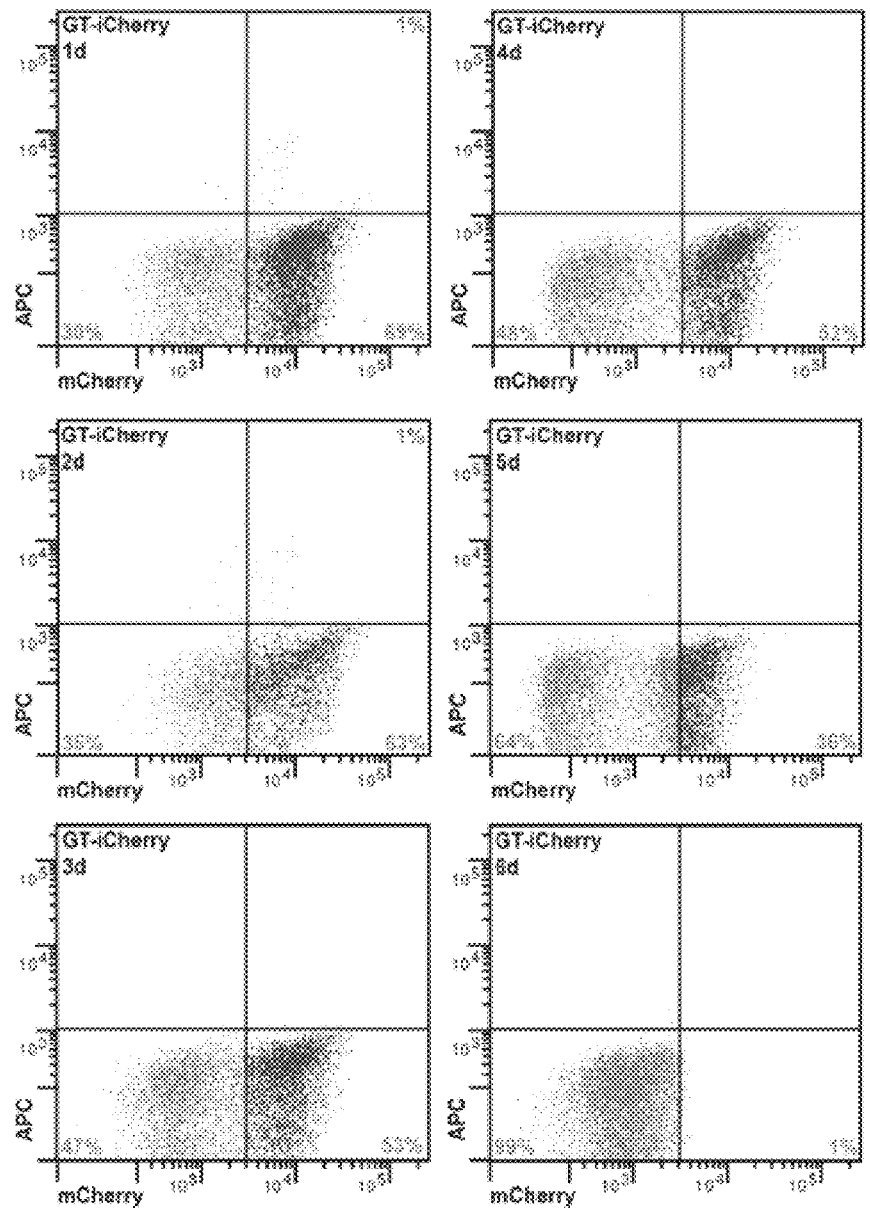
Figure 11C:
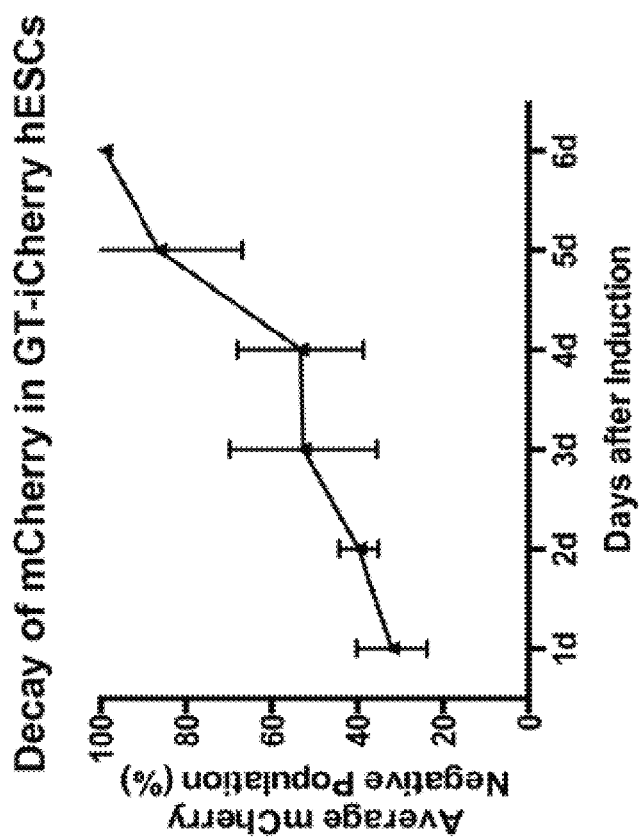

As shown in FIG. 11, the perdurance of mCherry expression in GT-iCherry hESCs that had been removed from doxycycline treatment was up to 6 days. At this point, 100% of the population had become mCherry$^{neg}$, identical to the sample of the GT-iCherry line that had not been induced (the negative control).

We examined the mechanism underlying the persistence of mCherry fluorescence in cells that no longer were being treated with doxycycline. Samples of GT-iCherry hESCs at days 2-4 after cessation of doxycycline induction were analysed by Q-PCR and compared to a sample of GT-iCherry that had not been induced with doxycycline. This compared mCherry RNA expression with protein expression.

Figure 12:
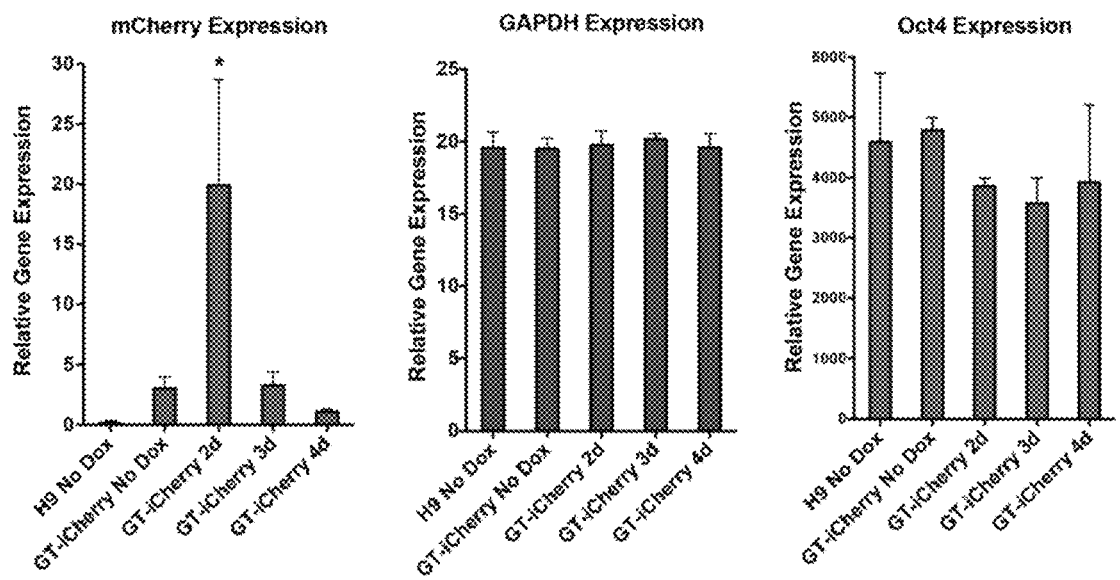
FIG. 12 provides column graphs quantifying gene expression analysis of and H9 hESCs and GT-iCherry hESCs post doxycycline treatment according to Example 7. GT-iCherry hESCs were induced for 3 days with doxycycline and harvested 2, 3 and 4 days after removal of doxycycline. A sample of GT-iCherry hESCs without induction served as a negative control. H9 hESCs were an additional negative control. Taqman Q-PCR probes used were mCherry, GAPDH and Oct4 (a pluripotent stem cell (PSC) marker). Statistical analyses included two-sample equal variance t-tests between the relative gene expression data for each sample and GT-iCherry No Dox. Asterix indicates the only data point whose P value suggested a significant difference for this test (p=0.05). Error bars represent SD (n=2).
Figure 15A:
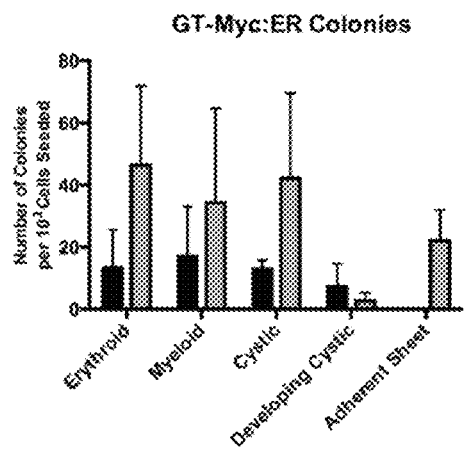
FIG. 15 provides column graphs quantifying colony scoring data for GT-MYC:ER and H9 colony forming assay according to Example 9. Graphs show the average number of day 21 colonies from 3 independent experiments. Orange columns indicate data from the treatment group (+4OHT), while black columns indicate no treatment (control). A and B. Scoring data divided into categories of colony type. C and D. Total number of colonies across all categories divided into control and +4OHT. Error bars are SEM (n=3).
Figure 15B:
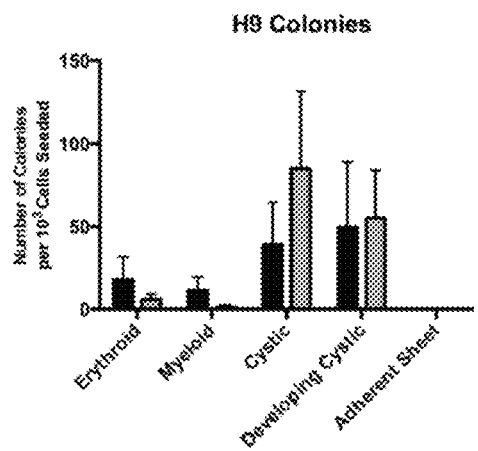
Figure 15C:
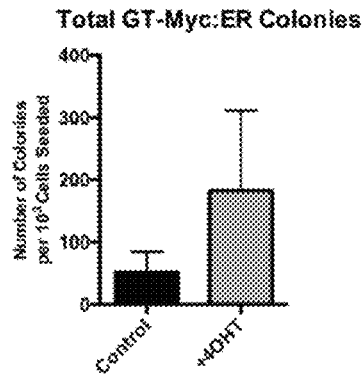
Figure 15D:
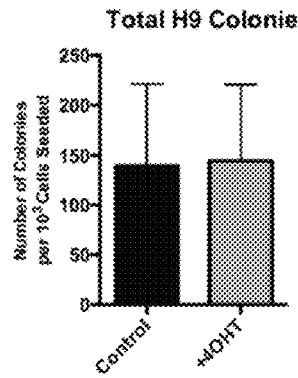

Flow cytometry results (FIG. 11) indicated that 3 days following removal doxycycline, up to 53% of cells remained mCherry$^{pos}$. In contrast, Q-PCR analysis displayed in FIG. 12 showed that mCherry RNA levels had returned to baseline levels by day 3, 3 days earlier than suggested by flow cytometry results (p>0.05). Indeed, the relative levels of mCherry mRNA in GT-iCherry hESCS at 3 and 4 days post doxycycline induction are not significantly different from that of GT-iCherry without induction (p>0.05). This result suggests that by 3 days after removal of doxycycline, the inducible vector system is not active at the genomic level and any fluorescence observed is in fact due to residual mCherry proteins in cells. GAPDH expression data confirms that this gene and by inference, its promoter, is equivalently active in all samples examined (p>0.05). Likewise, as expected, OCT4 expression shows little variance across the time frame of the experiment (p>0.05).

From the experiments on the GT-iCherry line of Examples 6 and 7, we deduced that peak of induction occurred between 48 and 72 hours after induction, and that mCherry fluorescence took another 6 days before it returned to baseline levels. However, Q-PCR analysis suggested that the slow decay of mCherry fluorescence following doxycycline removal was most likely contributed to by the persistence of mCherry protein in the absence of ongoing transcription.

Example 8—GT-MYC:ER Induction in an Endothelial Differentiation

Our earlier experiments showed that when either GFP or mCherry were expressed from the T2A sequence in the GT vector, they were produced at high levels in hESCs. This high expression level was retained as cells differentiated down a number of different mesodermal lineages, including hematopoietic cells. We also have evidence using embodiments of this vector that a high level of expression is also observed of fluorescent reporters when hESCs are differentiated toward neural and endodermal cell types. However, our experiments with the doxycycline inducible embodiment of this vector indicate that further work will be required ensure long-term vector integrity in hESCs before moving towards investigating its capacity in differentiated progeny.

Because of this, we sought to test the functionality of a second inducible embodiment of the vector, integrated into the H9 hESC line. This line comprised a MYC:ER fusion protein whose expression is linked to the GAPDH promoter via same T2A linker present in the GT-GFP and GT-mCherry vectors. MYC is an oncogene that drives proliferation, but can cause apoptosis when overexpressed in the absence of appropriate growth factor signalling. In the GT-MYC:ER line, MYC is only active in the presence of the inducing drug Tamoxifen (4OHT), which is a hormonal analogue for the estrogen receptor (ER). 4OHT binds the ER, which results in a conformational change and its release from a heat shock protein (HSP70). The liberated MYC:ER fusion protein is then free to translocate to the nucleus. Without this hormone binding event, HSP70 remains affixed to the MYC:ER fusion protein, retaining it in cytoplasm.

Previous work has characterised the activity of the MYC:ER fusion protein. It has also been shown that inappropriate activation of MYC in both fibroblasts and hESCs leads to apoptosis. Building on this, we were able to demonstrate functionality of the MYC:ER fusion protein in GT-MYC:ER hESCs by showing that the estrogen analogue 4OHT caused widespread death in hESC cultures when administered to cells grown under standard culture conditions.

In addition to its ability to induce apoptosis, the most well known function of MYC is to drive cell proliferation. In fact, MYC is commonly found to be over expressed in many human tumours and enforced expression of it can be used to generate immortal cell lines that can serve as a valuable research tool. Therefore, an important aim of this study was to test if induction of MYC with 4OHT could activate an 'immortalization' pathway via action of the MYC:ER fusion protein in differentiated cells. Furthermore, fusing the ER to other proteins may allow exogenous regulation of a variety of such proteins in differentiated material developed from hPSCs. This system has the potential to be an extremely valuable tool to, on one hand, investigate the biological function of a particular protein within mature tissue in vivo, and on the other hand, to drive development of hPSC derived differentiated products towards a desired pathway or phenotype by introducing a protein at a certain time point.

In a preliminary experiment to test this aim, an endothelial differentiation experiment was set up according to the protocol outlined in FIG. 13A. Embryoid bodies were disaggregated on day 6 into single cells and re-plated on 6-well plates coated with fibronectin dissolved in PBS at 5 µg/ml. In this monolayer culture stage, cells were supplemented only with VEGF at 30 ng/ml in AEL media, conditions that are highly selective for endothelial cell precursors. Half the wells had 4OHT added to them at a concentration of 1 µM, with media changed every 2-3 days for a further 4 weeks.

As can be seen from the micrographs in FIG. 13B, cells treated with 4OHT appear more refractive, observable by the 'glow' around their edges. This refractile morphology is consistent with the notion that these cells were either proliferating and/or displayed reduced adherence to the substrate. Reduced adherence is a frequently observed characteristic of cells undergoing neoplastic transformation and/or apoptosis. Cells without 4OHT treatment were much flatter, with long processes that were affixed firmly to the fibronectin-coated base of the well. Although a formal cell count was not performed in this preliminary experiment, it was observed that over time, +4OHT wells appeared to comprise a larger number of cells than wells that had not received 4OHT treatment.

The effect on cell morphology coupled with an apparent increased cell number observed in the cultures of GT-MYC:ER differentiated cells treated with 4OHT suggested that the inducible MYC:ER transgene was functional in differentiated cells. With these observations, we next set about to quantify the effect of MYC over-expression in the hematopoietic/endothelial differentiation system described herein.

Example 9—GT-MYC:ER Induction in a Methylcellulose-Matrigel Colony Forming Assay In order to examine the functionality of the GT-MYC:ER transgene in 4OHT treated differentiated cell types, we set up a methylcellulose-matrigel (MCM) colony forming assay with cells from day 3 EBs. FIG. 14A shows the differentiation protocol. The growth factors during the EB stage encourage the formation of mesoderm that comprises both hematopoietic and endothelial progenitors. Growth factors added to the MCM cultures stimulate hematopoietic and endothelial growth and differentiation.

Differentiated day 3 EBs representing parental H9 hESCS and the GT-MYC:ER line were disaggregated and the single cells resuspended in MCM medium (MC medium with 1.5% matrigel). The cell suspensions were distributed across individual wells of a 24 well plate, with 6 wells for the GT-MYC:ER line (3 wells with 4OHT added into the MCM medium at a concentration of 1 µM, and 3 wells without 4OHT), and 6 wells of the H9 line under the same conditions to serve as a control. Colonies were scored on day 21, and grouped into categories: erythroid, myeloid, cystic, developing cystic, or adherent sheet. Examples of these categories are shown in FIG. 14.

FIG. 15 shows results averaged from three independent experiments. The addition of 4OHT did not appear to effect the overall colony forming capacity of differentiated H9 cells (p>0.05) (FIG. 15D). As expected from earlier experiments, the MCM culture system promoted the formation of cystic colonies rather than hematopoeitic colonies. For both types of colonies, there was no statistically significant effect of 4OHT addition.

In the GT-MYC:ER cultures, the presence of 4OHT resulted in a larger number of colonies in total and in all categories except for the developing cystic colonies. Most notably, 4OHT treatment resulted in the development of adherent sheet colonies in the GT-MYC:ER cultures. This did not occur in the H9 cultures, nor in GT-MYC:ER cultures without 4OHT.

Figure 16:
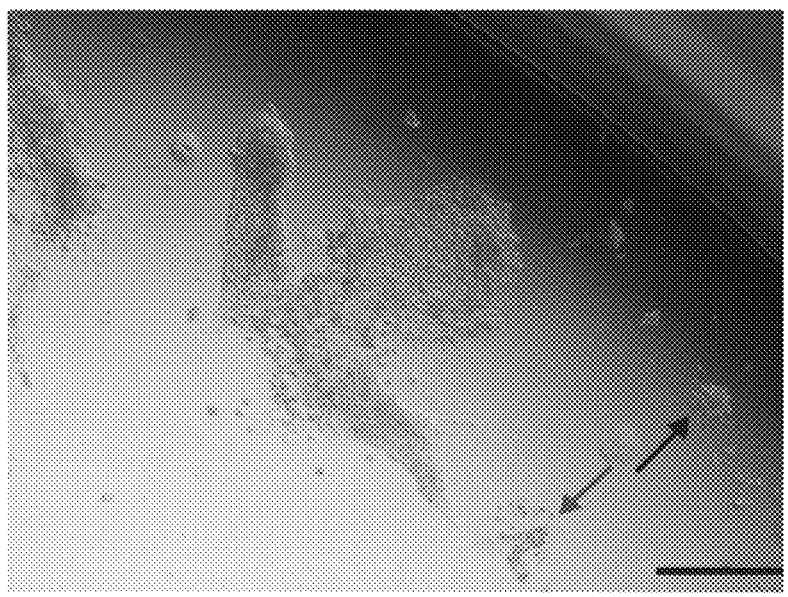
FIG. 16 provides a photomicrograph showing morphology and size of a typical adherent sheet colony according to Example 9. In the centre of the micrograph, a typical adherent sheet colony is pictured. The red arrow indicates a standard myeloid colony, and the black arrow indicates an erythroid colony. Scale bar 500 μm.

Not only were adherent sheet colonies restricted to 4OHT treated GT-MYC:ER cultures, but their size was substantially larger than any colony type seen in other culture conditions. As well as FIG. 14F that shows a typical adherent sheet colony, the size of these colonies can be seen relative to other colonies in FIG. 16.

As noted, statistical analyses suggested that the only significant difference between the treatment and control groups occurred for the adherent sheet category in the GT-MYC:ER data (two-sample, equal variance t-test; p=0.046, n=3).

Example 10—Discussion of the Examples as They Relate to GT-GFP and GT-mCherry as Constitutive Reporter Lines The aim of this study was to examine the functionality of embodiments of the vector disclosed herein throughout different stages of differentiation. In order to do this, PSCs comprising transgenes encoding GFP and mCherry were examined in their undifferentiated state and as they differentiated towards hematopoietic/endothelial cells. These studies revealed that fluorescent reporter genes expressed from a T2A sequence in the vector maintained robust fluorescence intensities and frequencies determined through flow cytometry analysis and fluorescent microscopy. We also investigated an inducible embodiment of the vector that expressed mCherry upon treatment with doxycycline. Lastly, we demonstrated utility of this vector system by showing that a MYC:ER fusion protein expressed from the vector altered hematopoietic/endothelial differentiation when cells were treated with 4OHT. Collectively, these data demonstrate that the vector is an expression system for hESC differentiation experiments.

Initial experiments with GT-GFP hESCs indicated that this line maintained robust GFP expression when cells were differentiated into hematopoietic mesoderm and endothelial-like cells. Cells comprising this vector also generated neural, cardiomyocyte and pancreatic cell types that retained high levels of reporter expression. Considering that hESCs with GT-transgenes have shown the ability to adopt cell fates that represent all three of the germ layers, this suggests that these cell lines retain their pluripotent capacity and that integration of the GT construct does not appear to effect the ability of these cells to differentiate. In our experiments performed with the GT-GFP line, the expression level of GFP remained consistently high throughout differentiation, providing strong evidence that the transgene was not subject to gene silencing effects.

One of the key uses of permanently tagging a cell with a reporter protein is to enable that cell to be identified within a mixed population. This use assumes that proteins expressed by one cell are not taken up by surrounding cells. However, under some circumstances, fluorescent proteins might be taken up by cells co-cultured with cells that were expressing a gene encoding the fluorescent protein. Although the mechanism of such transfer is unclear, we formally tested this possibility in the co-culture experiment of GT-GFP and GT-mCherry hESCs. Both microscopy images and flow cytometry data indicated that the GFPP$^{pos}$ and mCherry$^{pos}$ cell populations remained separate, with no overlap or 'double positive' cells. From this experiment, we concluded that if fluorescent protein transfer between cells does occur, it is likely to be a cell type-specific phenomenon.

Given the results showing that fluorescent protein expression was maintained during differentiation and that there was little evidence that fluorescent proteins were taken up by cells which did not express them, we used this system to test the clonality of cystic colonies arising in MCM cultures. In this experiment, day 3 progenitor cells of GT-GFP and GT-mCherry lines were cultured together in MCM for 18 days. It was found that colonies did not arise clonally, as we saw the development of a substantial number of 'mixed' colonies comprising both red and green cells. Incidentally, this experiment also showed that even after differentiating together, sometimes in mixed hematopoeitic/endothelial colonies, expression of fluorescent proteins was mutually exclusive suggesting that intercellular transfer of reporter proteins did not occur.

Example 11—Discussion of the Examples as They Relate to Analysis of mCherry Expression in GT-iCherry hESCs The usefulness of the vector disclosed herein would be increased if it could be engineered to enable inducible expression of a gene of interest. In this context, we examined the expression of mCherry in a version of the vector that was designed to deliver doxycycline inducible expression of genes of interest. Initial induction experiments with the GT-iCherry line showed that the optimal doxycycline treatment time for maximum induction of the mCherry reporter was 48 h-72 h.

Example 12—Discussion of the Examples as They Relate to GT-MYC:ER Induction in Mesodermal Differentiations Our preliminary experiment with GT-MYC:ER hESCs showed that when treated with 4OHT, cells derived from an endothelial differentiation protocol adopted a morphology resembling that reported of other cell types over expressing MYC. With this result, we undertook colony forming assay experiments in MCM to observe effects of induction of MYC during hematopoietic/endothelial differentiation. This assay was chosen because it provided an opportunity to observe effects on cell proliferation (colony size), progenitor frequency (colony number), and differentiation (colony type).

There were two clear results from this analysis. First, 4OHT treated GT-MYC:ER MCM cultures comprised a greater number of colonies than untreated cultures. This same effect was not observed in H9 control cultures. This result suggests that the GT-MYC:ER cultures treated with 4OHT had a higher chance of survival and/or proliferative potential, presumably due to activation of MYC. Second, 4OHT treatment of GT-MYC:ER MCM cultures promoted the appearance of a unique adherent sheet cell type, that not only was restricted to 4OHT GT-MYC:ER treated samples in number, but was also observed to be the largest and most dominant colony type. It can be postulated that this adherent sheet colony is in fact endothelial material, due to some similarities in cell morphology to known endothelial cell types, and that the growth factor combinations in the MCM could support growth of endothelium. This suggests that ectopic MYC expression at this stage of differentiation can activate unique cell fate pathways that are not normally present without this induction. Additionally, it is possible that MYC over-expression alters the cell cycle such that proliferation is increased, resulting in the expansive adherent sheet colonies.

Example 13

Figure 26A:
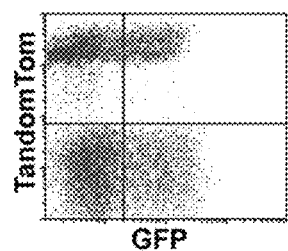
FIG. 26 provides a flow cytometry plot, immunofluorescent photomicrographs and photomicrographs of histological sections. A. Flow cytometry analysis showing robust and uniform expression of Tandem-Tomato fluorescent protein in cells differentiated towards cardiomyocytes, as evidenced by GFP expression of the cardiac specific NKX2-5 locus. B. Immunofluorescence analysis of tyrosine hydroxylase (TH) expressing neurons derived from GT-mCherry PSCs. C. Histological sections of teratomas derived from GT-LacZ PSCs. Tissues were stained with X-gal prior to sectioning to reveal areas of LacZ expression. This analysis demonstrates retention of transgene expression for extended periods in vivo in a number of different cell types, as indicated.
Figure 26B:
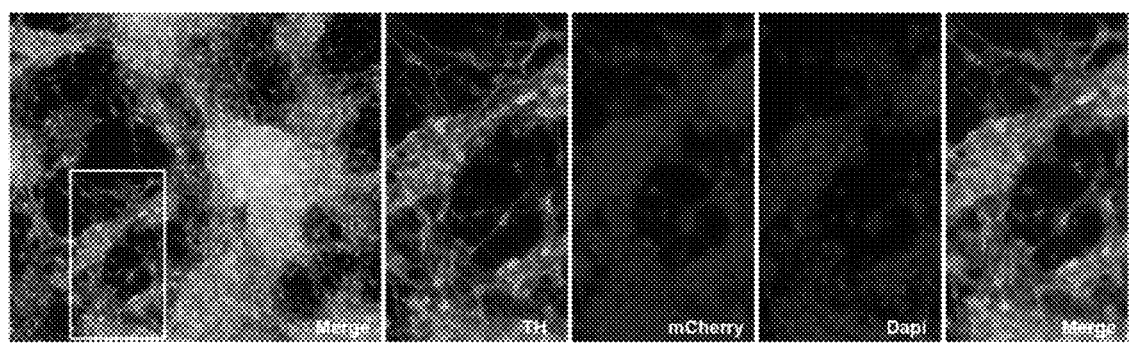
Figure 26C:
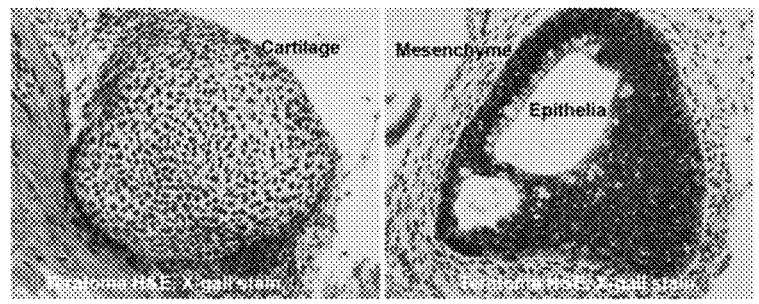

This example relates to the results provided in FIG. 26.

A. Parental NKX2-SGFP/w hESCs (Elliott D.A., et al. (2011) *Nature Methods*, 8: 1037) or NKX2-SGFP/w hESCs modified to contain the GT-Tandem Tomato expression vector were differentiated by treating cells with Activin A and the GSK-3 inhibitor CHIR-99021. At day 3 media was changed to RPMI-B27 containing the WNT antagonist IWP-2. From d7 onwards cells were maintained in RPMI/B27. At differentiation day 7, cells were harvested for flow cytometry analysis as described previously (Elliott et al, 2011).

B. Neural differentiation were performed using a modification of the dual smad inhibition method originally described by Chambers et al, 2009 (Chambers, S.M., et al. (2009) *Nature Biotechnology*, 27: 275). Once neuronal outgrowths were evident within cultures, cells were fixed and labeled with antibodies directed at Tyrosine Hydroxylase (TH) or mCherry. Nuclei were visualized by staining cells with DAPI. All images were taken on a Zeiss Axio Observer.Z1.

C. Teratomas were produced by injecting ~$10^6$ cells subcutaneously into the scapular of NOD/SCID-IL2Rgamma null mice. After approximately 3 months, when a palpable mass could be detected, animals were killed by cervical dislocation, the teratoma mass excised, cut into 1 mm×1 mm pieces and fixed in 4% PFA. After fixation, the teratoma pieces were stained with X-gal, re-fixed and then processed for histology. Histological sections were counter-stained with Haematoxylin and Eosin to reveal cellular substructures. Images were captures on a Zeiss axiovert microscope.

This data in this example shows that the GapTrap vector system maintains expression of a variety of transgenes in a range of differentiated cell types, both in vitro and following transplantation into immunocompromised mice.

The invention claimed is:

1. A vector for targeted integration of one or more exogenous nucleic acids into a constitutively expressed gene, the vector comprising:
   a 5' nucleic acid that is homologous to a genomic sequence 5' of a genomic stop codon of the constitutively expressed gene;
   an exogenous nucleic acid;
   a 3' nucleic acid that is homologous to a genomic sequence 3' of the genomic stop codon of the constitutively expressed gene; and
   a translation interruption-reinitiation signal operably linked to the 5' nucleic acid and the exogenous nucleic acid,
   wherein the constitutively expressed gene comprises GAPDH and the translation interruption-reinitiation signal is capable of replacing the stop codon of the constitutively expressed gene.

2. The vector of claim 1, wherein the translation interruption-reinitiation signal encodes a 2A peptide.

3. The vector of claim 2, wherein the translation interruption-reinitiation signal comprises SEQ ID NO: 1.

4. The vector of claim 1, wherein the 5' nucleic acid comprises about 25 to 100 bases, about 200 to 1000 bases, about 1 kb to 5 kb, or about 3.5 kb.

5. The vector of claim 4, wherein the 5' nucleic acid comprises SEQ ID NO: 2.

6. The vector of claim 1, wherein the 3' nucleic acid comprises about 25 to 100 bases, about 200 to 1000 bases, about 1 kb to 5 kb, or about 4 kb.

7. The vector of claim 6, wherein the 3' nucleic acid comprises SEQ ID NO: 3.

8. The vector of claim 1, further comprising an internal ribosomal entry site and a second exogenous nucleic acid, wherein the internal ribosomal entry site is operably linked to the exogenous nucleic acid and the second exogenous nucleic acid.

9. The vector of claim 8, wherein the internal ribosomal entry site comprises SEQ ID NO: 4.

10. The vector of claim 8, wherein the exogenous nucleic acid or the second exogenous nucleic acid encodes a marker protein or is a suicide gene.

11. The vector of claim 8, wherein the exogenous nucleic acid or the second exogenous nucleic acid comprises an inducible promoter.

12. The vector of claim 1, comprising SEQ ID NO: 9.

13. The vector of claim 8, comprising any one of SEQ ID NOs: 5, 6, 7 or 8.

14. An isolated cell comprising the vector of claim 1.

15. The isolated cell of claim 14 comprising a pluripotent stem cell, an embryonic stem cell, an induced pluripotent stem cell, or a cell differentiated from a pluripotent stem cell, an embryonic stem cell, or an induced pluripotent stem cell.

16. A method for expressing an exogenous nucleic acid in a cell, the method comprising cleaving in the cell genomic sequence comprising a constitutively expressed gene to produce a double stranded break in the genomic sequence, incorporating into the cell the vector of claim 1, and replacing the stop codon of the constitutively expressed gene with the translation interruption-reinitiation signal.

17. The vector of claim 10, wherein the marker protein is a fluorescent protein or an antibiotic resistance protein.

18. The vector of claim 10, wherein the suicide gene encodes thymidine kinase.

* * * * *